(12) United States Patent
Nilsson et al.

(10) Patent No.: US 8,506,964 B2
(45) Date of Patent: Aug. 13, 2013

(54) FUSION PROTEINS AND RELATED COMPOSITIONS, METHODS AND SYSTEMS FOR TREATMENT AND/OR PREVENTION OF ATHEROSCLEROSIS

(75) Inventors: Jan Nilsson, Genarp (SE); Goran K. Hansson, Stockholm (SE); Jan Holmgren, Vastra Frolunda (SE)

(73) Assignee: CardioVax, LLC, Torrance, CA (US)

( * ) Notice: Subject to any disclaimer, the term of this patent is extended or adjusted under 35 U.S.C. 154(b) by 20 days.

(21) Appl. No.: 13/021,635

(22) Filed: Feb. 4, 2011

(65) Prior Publication Data

US 2011/0300172 A1 Dec. 8, 2011

Related U.S. Application Data

(60) Provisional application No. 61/302,051, filed on Feb. 5, 2010.

(51) Int. Cl.
*A61K 39/00* (2006.01)
*C12P 21/00* (2006.01)
*C07K 19/00* (2006.01)
*C07K 1/107* (2006.01)

(52) U.S. Cl.
USPC ........ 424/192.1; 530/359; 435/69.3; 435/375

(58) Field of Classification Search
USPC ..................... 424/192.1; 530/359; 435/69.3, 435/375
See application file for complete search history.

(56) References Cited

U.S. PATENT DOCUMENTS

| | | | |
|---|---|---|---|
| 4,970,144 | A | 11/1990 | Fareed et al. |
| 5,408,038 | A | 4/1995 | Smith et al. |
| 5,972,890 | A | 10/1999 | Lees et al. |
| 7,527,795 | B2 | 5/2009 | Nilsson et al. |
| 7,528,225 | B2 | 5/2009 | Nilsson et al. |
| 7,537,758 | B2 | 5/2009 | Nilsson et al. |
| 7,544,360 | B2 | 6/2009 | Nilsson et al. |
| 7,558,611 | B2 | 7/2009 | Arnold et al. |
| 7,704,499 | B2 | 4/2010 | Nilsson et al. |
| 7,785,589 | B2 | 8/2010 | Nilsson et al. |
| 8,025,876 | B2 | 9/2011 | Nilsson et al. |
| 8,029,786 | B2 | 10/2011 | Nilsson et al. |
| 8,034,336 | B2 | 10/2011 | Nilsson et al. |
| RE43,581 | E | 8/2012 | Nilsson et al. |
| 2003/0105003 | A1 | 6/2003 | Nilsson et al. |
| 2004/0002111 | A1 | 1/2004 | Hansson et al. |
| 2006/0233817 | A1 | 10/2006 | Hansson |
| 2008/0070265 | A1 | 3/2008 | Hansson |
| 2009/0092618 | A1 | 4/2009 | Hansson |
| 2009/0117137 | A1 | 5/2009 | Nilsson et al. |
| 2009/0226475 | A1 | 9/2009 | Nilsson et al. |
| 2010/0183706 | A1 | 7/2010 | Nilsson et al. |
| 2011/0300172 | A1 | 12/2011 | Nilsson et al. |

FOREIGN PATENT DOCUMENTS

| | | |
|---|---|---|
| EP | 1676602 | 7/2006 |
| WO | 97/43331 | 11/1997 |
| WO | 98/42751 | 10/1998 |
| WO | 99/46598 | 3/1999 |
| WO | 01/64008 | 9/2001 |
| WO | 01/68119 | 9/2001 |
| WO | 02/080954 | 10/2002 |
| WO | 2004/000884 | 12/2003 |
| WO | 2012/065133 | 5/2012 |
| WO | 2012/065135 | 5/2012 |

OTHER PUBLICATIONS

Zhao et al. ,Circulation 120, S1018 (Nov. 2009).*
Zhao et al. ,Circulation 114: II, p. 287 (Oct. 2006).*
Caligiuri, G., et al., "Interleukin-10 deficiency increases atherosclerosis, thrombosis, and Low-density Lipoproteins in apolipoprotein E knockout mice." Molecular Medicine 2003, 10-17.
Caligiuri, G., et al., Protective immunity against atherosclerosis carried by B cells of hypercholesterolemic mice. The Journal of Clinical Investigation, 2002, 109: 745-753.
Ameli, S., et al., "Effect of immunization with homologous LDL and oxidized LDL on early atherosclerosis in hypercholesterolemic rabbits." Arteriosclerosis, Thrombosis and Vascular Biology 1996, 16: 1074-1079.
Anonymous, "APB_HUMAN." Oct. 1, 2000, pp. 1-7 XP 55019488, retrieved from the internet URL: http:// www.Uniprot.org/uniprot/P04114.txt?version=23.
Klingenberg et al. "Intranasal immunization with apolipoprotein B-100 fusion protein induces antigen-specific regulatory T cells and reduces atherosclerosis." Arteriosclerosis Thrombosis and Vascular Biology 30:, 2010.
Brown et al., "A vaccine against atherosclerosis." Drug Discovery Today. 7(11):588-590, 2002.
Chen, S., et al., "Apolipoprotein B-48 is the product of a messenger RNA with organ-specific in frame stop codon." Science 1987, 238: 363-366.
Chyu, K., et al., "Immunization using Apo B-100 related epitope reduces atherosclerosis and plaque inflammation in hypercholesterolemic apo E (-/-) mice." Biochemical and Biophysical Research Communications 2005, 338: 1982-1989.
Fredrickson et al., "Treatment with apo B peptide vaccine inhitbits atherosclerosis in human apo B-100 transgenic mice without inducing an increase in peptide-specific antibodies." J. Internal Med. 264: 563-570, 2008.
Fredrickson, G., et al., "Atheroprotective immunization with MDA-modified apo B-100 peptide sequence is associated with activation of Th2 specific antibody expression." Autoimmunity 2005, 38: 171-179.
Fredrickson, G., et al., "Autoantibody against the amino acid sequence 661-680 in apo B-100 is associated with decreased carotid stenosis and cardiovascular events." Atherosclerosis, 2007, 194: e188-e192. 194.
Fredrickson, G., et al., "Identification of immune responses against aldehyde-modified peptide sequences in ApoB associated with cardiovascular disease." Arterioscler. Thomb. Vasc. Biol. 2003, 23: 872-878.
Fredrickson, G., et al., "Inhibition of atherosclerosis in Apo-E-null mice by immunization with Apo-B-100 peptide sequences." Arterioscler. Thomb. Vasc. Biol. 2003: 23: 879-884.

(Continued)

*Primary Examiner* — Chih-Min Kam
(74) *Attorney, Agent, or Firm* — K&L Gates LLP; Louis C. Cullman; Michelle Glasky Bergman

(57) ABSTRACT

A fusion protein comprising an antigenic fragment of apoB-100 and a suitable carrier and related compositions methods and systems.

13 Claims, 18 Drawing Sheets

(56) References Cited

OTHER PUBLICATIONS

Fredrickson, Gunilla Nordin et al., "Inhibition of atherosclerosis in apo E null mice by immunization with native and MDA-modified apo B peptide sequences." Journal of the American College of Cardiology, Elsevier, New York, NY, US, vol. 39, No. 5; Supplement A; p. 240A; Mar. 2002.
Fredrikson et al. "Association Between IgM Against an Aldehyde-Modified Peptide in Apolipoprotein B-100 and Progression of Carotid Disease." Stroke, May 2007, 38: 1495-1500.
Fredrikson et al., "Associations between autoantibodies against apolipoprotein B-100 peptides and vascular complications in patients with type 2 diabetes." Diabetologia (2009), 52: 1426-1433.
Freigang, S., et al., "Immunization of LDL receptor-deficient mice with homologous malondialdehyde-modified and native LDL reduces progression of atherosclerosis by mechanisms other than induction of high titers of anitbodies to oxidative neoepitopes." Arterioscler. Thomb. Vasc. Bio., 1998, 18: 1972-1982.
George, J. et al., "Hyperimmunization of apo-E-deficient mice homologous malondialdehyde low-denisity lipoprotein suppresses early atherogenesis." Arteriosclerosis, 138:147-152, 1998.
George, J., et al., "Induction of early atherosclerosis in LDL-receptor deficient mice immuized with beta-glycoprotein I." American Heart Association 1998, 1108-1115.
Halvoet, P. et al., "Oxidized LDL and malondialdehyde-modified LDL in patients with acute coronary syndromes and stable coronary artery disease." Circulation 1998, 98: 1487-1494.
Hansson et al. "Vaccination against atherosclerosis? Induction of atheroprotective immunity." Semin. Immunopathol. (2009).
Pedersen et al. "The proinflammatory effect or uraemia overrules the anti-atherogenic potentiation of immunization with oxidized LDL in apoE-/-mice" Nephrology Dialysis Transplantation 25:2486-2491, 2010.
Hansson, K., "Inflammation, atherosclerosis, and coronary artery disease." The New England Journal of Medicine 2005, 352: 1685-1695.
Law, S.W., Proceedings National Academy of Sciences 83 (21), 8142-6, 1986.
Nilsson, J. et al., "Autoimmunity in atherosclerosis: a protective response losing control." Journal of Internal Medicine 2008, 263: 464-478.
Nilsson, J. et al., "Immunization with homologous oxidized low density lipoprotein reduces neointimal formation after balloon injury in hypercholesterolemic rabbits." Journal of American College of Cardiology 1997, 30: 1886-1891.
Nilsson, J. et al., "Immunomodulation of atherosclerosis." Arteriosclerosis, Thrombosis, and Vascular Biology 2005, 25 : 18-28.
Palinski, W. et al., "Antisera and Monoclonal Antibodies Specific for Epitopes Generated during Oxidative Modification of Low Density Lipoprotein." Arteriosclerosis, 10:325-335, 1990.
Palinski, W. et al., "Immunization of low density lipoprotein (LDL) receptor-deficient rabbits with homologous malondialdehyde-modified LDL reduces atherogenesis", PNAS USA, 92:821-825, Jan. 1995.
Sjogren et al. "High plasma concentrations of autoantibodies against native peptide 210 of apoB-100 are related to less coronary atherosclerosis and lower risk of myocardial infarction." European Heart Journal (2008) 29, 2218-2226.
Stemme et al., "T lymphocytes from human atherosclerotic plagues recognize oxidized low density lipoprotein." pp. 3893-3897, PNAS, vol. 92, Apr. 1995 (USA).
Yang et al. "Sequence, structure, receptor-binding domains and internal repeats of human apolipoprotein B-100." Nature, vol. 23, Oct. 1986, pp. 738-742.
Zhao et al. Circulation 114: 11, p. 287 (Oct. 2006).
Zhao et al., "Athero-protective effects of immunization with apoB-100 related peptide vaccine in apoE-/-mice is associated with enhanced CD8 Regulatory T Cell Response." Circulation, 2009; 120: S1018.
Zhou, X. et al., "LDL immunization induces T-cell-dependent antibody formation and protection against atherosclerosis." Arteriosclerosis, Thrombosis and Vascular Biology, 2001, 21: 108-114.
Chen et al., Primary sequence mapping of human apolipoprotein B-100 epitopes. Eur J Biochem 175: 111-118, 1988.

* cited by examiner

```
                        SEQUENCE LISTING

<160> NUMBER OF SEQ ID NOS: 305

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Glu Glu Glu Met Leu Glu Asn Val Ser Leu Val Cys Pro Lys Asp Ala
1               5                   10                  15

Thr Arg Phe Lys
            20

<210> SEQ ID NO 2
<211> LENGTH: 20
<212> TYPE: PRT
<213> ORGANISM: Artificial Sequence
<220> FEATURE:
<223> OTHER INFORMATION: Synthetic peptide

<400> SEQUENCE: 2

Ala Thr Arg Phe Lys His Leu Arg Lys Tyr Thr Tyr Asn Tyr Glu Ala
1               5                   10                  15

Glu Ser Ser Ser
            20

<210> SEQ ID NO 3
<211> LENGTH: 20
<212> TYPE: PRT
<213> ORGANISM: Artificial Sequence
<220> FEATURE:
<223> OTHER INFORMATION: Synthetic peptide

<400> SEQUENCE: 3

Ala Glu Ser Ser Ser Gly Val Pro Gly Thr Ala Asp Ser Arg Ser Ala
1               5                   10                  15

Thr Arg Ile Asn
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic peptide

<400> SEQUENCE: 4

Ala Thr Arg Ile Asn Cys Lys Val Glu Leu Glu Val Pro Gln Leu Cys
1               5                   10                  15
```

```
Ser Phe Ile Leu
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide

<400> SEQUENCE: 5

Cys Ser Phe Ile Leu Lys Thr Ser Gln Cys Thr Leu Lys Glu Val Tyr
1               5                   10                  15

Gly Phe Asn Pro
            20

<210> SEQ ID NO 6
<211> LENGTH: 20
<212> TYPE: PRT
<213> ORGANISM: Artificial Sequence
<220> FEATURE:
<223> OTHER INFORMATION: Synthetic peptide

<400> SEQUENCE: 6

Tyr Gly Phe Asn Pro Glu Gly Lys Ala Leu Leu Lys Lys Thr Lys Asn
1               5                   10                  15

Ser Glu Glu Phe
            20

<210> SEQ ID NO 7
<211> LENGTH: 20
<212> TYPE: PRT
<213> ORGANISM: Artificial Sequence
<220> FEATURE:
<223> OTHER INFORMATION: Synthetic peptide

<400> SEQUENCE: 7

Asn Ser Glu Glu Phe Ala Ala Ala Met Ser Arg Tyr Glu Leu Lys Leu
1               5                   10                  15

Ala Ile Pro Glu
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic peptide

<400> SEQUENCE: 8

Leu Ala Ile Pro Glu Gly Lys Gln Val Phe Leu Tyr Pro Glu Lys Asp
1               5                   10                  15

Glu Pro Thr Tyr
            20

<210> SEQ ID NO 9
<211> LENGTH: 20
<212> TYPE: PRT
<213> ORGANISM: Artificial Sequence
<220> FEATURE:
<223> OTHER INFORMATION: Synthetic peptide

<400> SEQUENCE: 9

Asp Glu Pro Thr Tyr Ile Leu Asn Ile Lys Arg Gly Ile Ile Ser Ala
1               5                   10                  15
```

```
Leu Leu Val Pro
            20

<210> SEQ ID NO 10
<211> LENGTH: 20
<212> TYPE: PRT
<213> ORGANISM: Artificial Sequence
<220> FEATURE:
<223> OTHER INFORMATION: Synthetic peptide

<400> SEQUENCE: 10

Ala Leu Leu Val Pro Pro Glu Thr Glu Glu Ala Lys Gln Val Leu Phe
1               5                   10                  15

Leu Asp Thr Val
            20

<210> SEQ ID NO 11
<211> LENGTH: 20
<212> TYPE: PRT
<213> ORGANISM: Artificial Sequence
<220> FEATURE:
<223> OTHER INFORMATION: Synthetic peptide

<400> SEQUENCE: 11

Phe Leu Asp Thr Val Tyr Gly Asn Cys Ser Thr His Phe Thr Val Lys
1               5                   10                  15

Thr Arg Lys Gly
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic peptide

<400> SEQUENCE: 12

Lys Thr Arg Lys Gly Asn Val Ala Thr Glu Ile Ser Thr Glu Arg Asp
1               5                   10                  15

Leu Gly Gln Cys
            20

<210> SEQ ID NO 13
<211> LENGTH: 20
<212> TYPE: PRT
<213> ORGANISM: Artificial Sequence
<220> FEATURE:
<223> OTHER INFORMATION: Synthetic peptide

<400> SEQUENCE: 13

Asp Leu Gly Gln Cys Asp Arg Phe Lys Pro Ile Arg Thr Gly Ile Ser
1               5                   10                  15

Pro Leu Ala Leu
            20

<210> SEQ ID NO 14
<211> LENGTH: 20
<212> TYPE: PRT
<213> ORGANISM: Artificial Sequence
<220> FEATURE:
<223> OTHER INFORMATION: Synthetic peptide

<400> SEQUENCE: 14

Ser Pro Leu Ala Leu Ile Lys Gly Met Thr Arg Pro Leu Ser Thr Leu
1               5                   10                  15
```

```
Ile Ser Ser Ser
            20

<210> SEQ ID NO 15
<211> LENGTH: 20
<212> TYPE: PRT
<213> ORGANISM: Artificial Sequence
<220> FEATURE:
<223> OTHER INFORMATION: Synthetic peptide

<400> SEQUENCE: 15

Leu Ile Ser Ser Ser Gln Ser Cys Gln Tyr Thr Leu Asp Ala Lys Arg
1               5                   10                  15

Lys His Val Ala
            20

<210> SEQ ID NO 16
<211> LENGTH: 20
<212> TYPE: PRT
<213> ORGANISM: Artificial Sequence
<220> FEATURE:
<223> OTHER INFORMATION: Synthetic peptide

<400> SEQUENCE: 16

Arg Lys His Val Ala Glu Ala Ile Cys Lys Glu Gln His Leu Phe Leu
1               5                   10                  15

Pro Phe Ser Tyr
            20

<210> SEQ ID NO 17
<211> LENGTH: 20
<212> TYPE: PRT
<213> ORGANISM: Artificial Sequence
<220> FEATURE:
<223> OTHER INFORMATION: Synthetic peptide

<400> SEQUENCE: 17

Leu Pro Phe Ser Tyr Asn Asn Lys Tyr Gly Met Val Ala Gln Val Thr
1               5                   10                  15

Gln Thr Leu Lys
            20

<210> SEQ ID NO 18
<211> LENGTH: 20
<212> TYPE: PRT
<213> ORGANISM: Artificial Sequence
<220> FEATURE:
<223> OTHER INFORMATION: Synthetic peptide

<400> SEQUENCE: 18

Thr Gln Thr Leu Lys Leu Glu Asp Thr Pro Lys Ile Asn Ser Arg Phe
1               5                   10                  15

Phe Gly Glu Gly
            20

<210> SEQ ID NO 19
<211> LENGTH: 20
<212> TYPE: PRT
<213> ORGANISM: Artificial Sequence
<220> FEATURE:
<223> OTHER INFORMATION: Synthetic peptide

<400> SEQUENCE: 19

Phe Phe Gly Glu Gly Thr Lys Lys Met Gly Leu Ala Phe Glu Ser Thr
1               5                   10                  15
```

```
Lys Ser Thr Ser
        20

<210> SEQ ID NO 20
<211> LENGTH: 20
<212> TYPE: PRT
<213> ORGANISM: Artificial Sequence
<220> FEATURE:
<223> OTHER INFORMATION: Synthetic peptide

<400> SEQUENCE: 20

Thr Lys Ser Thr Ser Pro Pro Lys Gln Ala Glu Ala Val Leu Lys Thr
1               5                   10                  15

Leu Gln Glu Leu
        20

<210> SEQ ID NO 21
<211> LENGTH: 20
<212> TYPE: PRT
<213> ORGANISM: Artificial Sequence
<220> FEATURE:
<223> OTHER INFORMATION: Synthetic peptide

<400> SEQUENCE: 21

Thr Leu Gln Glu Leu Lys Lys Leu Thr Ile Ser Glu Gln Asn Ile Gln
1               5                   10                  15

Arg Ala Asn Leu
        20

<210> SEQ ID NO 22
<211> LENGTH: 20
<212> TYPE: PRT
<213> ORGANISM: Artificial Sequence
<220> FEATURE:
<223> OTHER INFORMATION: Synthetic peptide

<400> SEQUENCE: 22

Gln Arg Ala Asn Leu Phe Asn Lys Leu Val Thr Glu Leu Arg Gly Leu
1               5                   10                  15

Ser Asp Glu Ala
        20

<210> SEQ ID NO 23
<211> LENGTH: 20
<212> TYPE: PRT
<213> ORGANISM: Artificial Sequence
<220> FEATURE:
<223> OTHER INFORMATION: Synthetic peptide

<400> SEQUENCE: 23

Leu Ser Asp Glu Ala Val Thr Ser Leu Leu Pro Gln Leu Ile Glu Val
1               5                   10                  15

Ser Ser Pro Ile
        20

<210> SEQ ID NO 24
<211> LENGTH: 20
<212> TYPE: PRT
<213> ORGANISM: Artificial Sequence
<220> FEATURE:
<223> OTHER INFORMATION: Synthetic peptide

<400> SEQUENCE: 24

Val Ser Ser Pro Ile Thr Leu Gln Ala Leu Val Gln Cys Gly Gln Pro
1               5                   10                  15
```

```
Gln Cys Ser Thr
            20

<210> SEQ ID NO 25
<211> LENGTH: 20
<212> TYPE: PRT
<213> ORGANISM: Artificial Sequence
<220> FEATURE:
<223> OTHER INFORMATION: Synthetic peptide

<400> SEQUENCE: 25

Pro Gln Cys Ser Thr His Ile Leu Gln Trp Leu Lys Arg Val His Ala
1               5                   10                  15

Asn Pro Leu Leu
            20

<210> SEQ ID NO 26
<211> LENGTH: 20
<212> TYPE: PRT
<213> ORGANISM: Artificial Sequence
<220> FEATURE:
<223> OTHER INFORMATION: Synthetic peptide

<400> SEQUENCE: 26

Ala Asn Pro Leu Leu Ile Asp Val Val Thr Tyr Leu Val Ala Leu Ile
1               5                   10                  15

Pro Glu Pro Ser
            20

<210> SEQ ID NO 27
<211> LENGTH: 20
<212> TYPE: PRT
<213> ORGANISM: Artificial Sequence
<220> FEATURE:
<223> OTHER INFORMATION: Synthetic peptide

<400> SEQUENCE: 27

Ile Pro Glu Pro Ser Ala Gln Gln Leu Arg Glu Ile Phe Asn Met Ala
1               5                   10                  15

Arg Asp Gln Arg
            20

<210> SEQ ID NO 28
<211> LENGTH: 20
<212> TYPE: PRT
<213> ORGANISM: Artificial Sequence
<220> FEATURE:
<223> OTHER INFORMATION: Synthetic peptide

<400> SEQUENCE: 28

Ala Arg Asp Gln Arg Ser Arg Ala Thr Leu Tyr Ala Leu Ser His Ala
1               5                   10                  15

Val Asn Asn Tyr
            20

<210> SEQ ID NO 29
<211> LENGTH: 20
<212> TYPE: PRT
<213> ORGANISM: Artificial Sequence
<220> FEATURE:
<223> OTHER INFORMATION: Synthetic peptide

<400> SEQUENCE: 29

Ala Val Asn Asn Tyr His Lys Thr Asn Pro Thr Gly Thr Gln Glu Leu
1               5                   10                  15
```

```
Leu Asp Ile Ala
         20

<210> SEQ ID NO 30
<211> LENGTH: 20
<212> TYPE: PRT
<213> ORGANISM: Artificial Sequence
<220> FEATURE:
<223> OTHER INFORMATION: Synthetic peptide

<400> SEQUENCE: 30

Leu Leu Asp Ile Ala Asn Tyr Leu Met Glu Gln Ile Gln Asp Asp Cys
1               5                   10                  15

Thr Gly Asp Glu
         20

<210> SEQ ID NO 31
<211> LENGTH: 20
<212> TYPE: PRT
<213> ORGANISM: Artificial Sequence
<220> FEATURE:
<223> OTHER INFORMATION: Synthetic peptide

<400> SEQUENCE: 31

Cys Thr Gly Asp Glu Asp Tyr Thr Tyr Leu Ile Leu Arg Val Ile Gly
1               5                   10                  15

Asn Met Gly Gln
         20

<210> SEQ ID NO 32
<211> LENGTH: 20
<212> TYPE: PRT
<213> ORGANISM: Artificial Sequence
<220> FEATURE:
<223> OTHER INFORMATION: Synthetic peptide

<400> SEQUENCE: 32

Gly Asn Met Gly Gln Thr Met Glu Gln Leu Thr Pro Glu Leu Lys Ser
1               5                   10                  15

Ser Ile Leu Lys
         20

<210> SEQ ID NO 33
<211> LENGTH: 20
<212> TYPE: PRT
<213> ORGANISM: Artificial Sequence
<220> FEATURE:
<223> OTHER INFORMATION: Synthetic peptide

<400> SEQUENCE: 33

Ser Ser Ile Leu Lys Cys Val Gln Ser Thr Lys Pro Ser Leu Met Ile
1               5                   10                  15

Gln Lys Ala Ala
         20

<210> SEQ ID NO 34
<211> LENGTH: 20
<212> TYPE: PRT
<213> ORGANISM: Artificial Sequence
<220> FEATURE:
<223> OTHER INFORMATION: Synthetic peptide

<400> SEQUENCE: 34

Ile Gln Lys Ala Ala Ile Gln Ala Leu Arg Lys Met Glu Pro Lys Asp
1               5                   10                  15
```

```
Lys Asp Gln Glu
        20

<210> SEQ ID NO 35
<211> LENGTH: 20
<212> TYPE: PRT
<213> ORGANISM: Artificial Sequence
<220> FEATURE:
<223> OTHER INFORMATION: Synthetic peptide

<400> SEQUENCE: 35

Asp Lys Asp Gln Glu Val Leu Leu Gln Thr Phe Leu Asp Asp Ala Ser
1               5                   10                  15

Pro Gly Asp Lys
        20

<210> SEQ ID NO 36
<211> LENGTH: 20
<212> TYPE: PRT
<213> ORGANISM: Artificial Sequence
<220> FEATURE:
<223> OTHER INFORMATION: Synthetic peptide

<400> SEQUENCE: 36

Ser Pro Gly Asp Lys Arg Leu Ala Ala Tyr Leu Met Leu Met Arg Ser
1               5                   10                  15

Pro Ser Gln Ala
        20

<210> SEQ ID NO 37
<211> LENGTH: 20
<212> TYPE: PRT
<213> ORGANISM: Artificial Sequence
<220> FEATURE:
<223> OTHER INFORMATION: Synthetic peptide

<400> SEQUENCE: 37

Ser Pro Ser Gln Ala Asp Ile Asn Lys Ile Val Gln Ile Leu Pro Trp
1               5                   10                  15

Glu Gln Asn Glu
        20

<210> SEQ ID NO 38
<211> LENGTH: 20
<212> TYPE: PRT
<213> ORGANISM: Artificial Sequence
<220> FEATURE:
<223> OTHER INFORMATION: Synthetic peptide

<400> SEQUENCE: 38

Trp Glu Gln Asn Glu Gln Val Lys Asn Phe Val Ala Ser His Ile Ala
1               5                   10                  15

Asn Ile Leu Asn
        20

<210> SEQ ID NO 39
<211> LENGTH: 20
<212> TYPE: PRT
<213> ORGANISM: Artificial Sequence
<220> FEATURE:
<223> OTHER INFORMATION: Synthetic peptide

<400> SEQUENCE: 39

Ala Asn Ile Leu Asn Ser Glu Glu Leu Asp Ile Gln Asp Leu Lys Lys
1               5                   10                  15
```

```
Leu Val Lys Glu
            20

<210> SEQ ID NO 40
<211> LENGTH: 20
<212> TYPE: PRT
<213> ORGANISM: Artificial Sequence
<220> FEATURE:
<223> OTHER INFORMATION: Synthetic peptide

<400> SEQUENCE: 40

Lys Leu Val Lys Glu Ala Leu Lys Glu Ser Gln Leu Pro Thr Val Met
1               5                   10                  15

Asp Phe Arg Lys
            20

<210> SEQ ID NO 41
<211> LENGTH: 20
<212> TYPE: PRT
<213> ORGANISM: Artificial Sequence
<220> FEATURE:
<223> OTHER INFORMATION: Synthetic peptide

<400> SEQUENCE: 41

Met Asp Phe Arg Lys Phe Ser Arg Asn Tyr Gln Leu Tyr Lys Ser Val
1               5                   10                  15

Ser Leu Pro Ser
            20

<210> SEQ ID NO 42
<211> LENGTH: 20
<212> TYPE: PRT
<213> ORGANISM: Artificial Sequence
<220> FEATURE:
<223> OTHER INFORMATION: Synthetic peptide

<400> SEQUENCE: 42

Val Ser Leu Pro Ser Leu Asp Pro Ala Ser Ala Lys Ile Glu Gly Asn
1               5                   10                  15

Leu Ile Phe Asp
            20

<210> SEQ ID NO 43
<211> LENGTH: 20
<212> TYPE: PRT
<213> ORGANISM: Artificial Sequence
<220> FEATURE:
<223> OTHER INFORMATION: Synthetic peptide

<400> SEQUENCE: 43

Asn Leu Ile Phe Asp Pro Asn Asn Tyr Leu Pro Lys Glu Ser Met Leu
1               5                   10                  15

Lys Thr Thr Leu
            20

<210> SEQ ID NO 44
<211> LENGTH: 20
<212> TYPE: PRT
<213> ORGANISM: Artificial Sequence
<220> FEATURE:
<223> OTHER INFORMATION: Synthetic peptide

<400> SEQUENCE: 44

Leu Lys Thr Thr Leu Thr Ala Phe Gly Phe Ala Ser Ala Asp Leu Ile
1               5                   10                  15
```

```
Glu Ile Gly Leu
            20

<210> SEQ ID NO 45
<211> LENGTH: 20
<212> TYPE: PRT
<213> ORGANISM: Artificial Sequence
<220> FEATURE:
<223> OTHER INFORMATION: Synthetic peptide

<400> SEQUENCE: 45

Ile Glu Ile Gly Leu Glu Gly Lys Gly Phe Glu Pro Thr Leu Glu Ala
1               5                   10                  15

Leu Phe Gly Lys
            20

<210> SEQ ID NO 46
<211> LENGTH: 20
<212> TYPE: PRT
<213> ORGANISM: Artificial Sequence
<220> FEATURE:
<223> OTHER INFORMATION: Synthetic peptide

<400> SEQUENCE: 46

Ala Leu Phe Gly Lys Gln Gly Phe Phe Pro Asp Ser Val Asn Lys Ala
1               5                   10                  15

Leu Tyr Trp Val
            20

<210> SEQ ID NO 47
<211> LENGTH: 20
<212> TYPE: PRT
<213> ORGANISM: Artificial Sequence
<220> FEATURE:
<223> OTHER INFORMATION: Synthetic peptide

<400> SEQUENCE: 47

Ala Leu Tyr Trp Val Asn Gly Gln Val Pro Asp Gly Val Ser Lys Val
1               5                   10                  15

Leu Val Asp His
            20

<210> SEQ ID NO 48
<211> LENGTH: 20
<212> TYPE: PRT
<213> ORGANISM: Artificial Sequence
<220> FEATURE:
<223> OTHER INFORMATION: Synthetic peptide

<400> SEQUENCE: 48

Val Leu Val Asp His Phe Gly Tyr Thr Lys Asp Lys His Glu Gln
1               5                   10                  15

Asp Met Val Asn
            20

<210> SEQ ID NO 49
<211> LENGTH: 20
<212> TYPE: PRT
<213> ORGANISM: Artificial Sequence
<220> FEATURE:
<223> OTHER INFORMATION: Synthetic peptide

<400> SEQUENCE: 49

Gln Asp Met Val Asn Gly Ile Met Leu Ser Val Glu Lys Leu Ile Lys
1               5                   10                  15
```

```
Asp Leu Lys Ser
            20

<210> SEQ ID NO 50
<211> LENGTH: 20
<212> TYPE: PRT
<213> ORGANISM: Artificial Sequence
<220> FEATURE:
<223> OTHER INFORMATION: Synthetic peptide

<400> SEQUENCE: 50

Lys Asp Leu Lys Ser Lys Glu Val Pro Glu Ala Arg Ala Tyr Leu Arg
1               5                   10                  15

Ile Leu Gly Glu
            20

<210> SEQ ID NO 51
<211> LENGTH: 20
<212> TYPE: PRT
<213> ORGANISM: Artificial Sequence
<220> FEATURE:
<223> OTHER INFORMATION: Synthetic peptide

<400> SEQUENCE: 51

Arg Ile Leu Gly Glu Glu Leu Gly Phe Ala Ser Leu His Asp Leu Gln
1               5                   10                  15

Leu Leu Gly Lys
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic peptide

<400> SEQUENCE: 52

Gln Leu Leu Gly Lys Leu Leu Leu Met Gly Ala Arg Thr Leu Gln Gly
1               5                   10                  15

Ile Pro Gln Met
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic peptide

<400> SEQUENCE: 53

Gly Ile Pro Gln Met Ile Gly Glu Val Ile Arg Lys Gly Ser Lys Asn
1               5                   10                  15

Asp Phe Phe Leu
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic peptide

<400> SEQUENCE: 54

Asn Asp Phe Phe Leu His Tyr Ile Phe Met Glu Asn Ala Phe Glu Leu
1               5                   10                  15
```

```
Pro Thr Gly Ala
        20

<210> SEQ ID NO 55
<211> LENGTH: 20
<212> TYPE: PRT
<213> ORGANISM: Artificial Sequence
<220> FEATURE:
<223> OTHER INFORMATION: Synthetic peptide

<400> SEQUENCE: 55

Leu Pro Thr Gly Ala Gly Leu Gln Leu Gln Ile Ser Ser Ser Gly Val
1               5                   10                  15

Ile Ala Pro Gly
        20

<210> SEQ ID NO 56
<211> LENGTH: 20
<212> TYPE: PRT
<213> ORGANISM: Artificial Sequence
<220> FEATURE:
<223> OTHER INFORMATION: Synthetic peptide

<400> SEQUENCE: 56

Val Ile Ala Pro Gly Ala Lys Ala Gly Val Lys Leu Glu Val Ala Asn
1               5                   10                  15

Met Gln Ala Glu
        20

<210> SEQ ID NO 57
<211> LENGTH: 20
<212> TYPE: PRT
<213> ORGANISM: Artificial Sequence
<220> FEATURE:
<223> OTHER INFORMATION: Synthetic peptide

<400> SEQUENCE: 57

Asn Met Gln Ala Glu Leu Val Ala Lys Pro Ser Val Ser Val Glu Phe
1               5                   10                  15

Val Thr Asn Met
        20

<210> SEQ ID NO 58
<211> LENGTH: 20
<212> TYPE: PRT
<213> ORGANISM: Artificial Sequence
<220> FEATURE:
<223> OTHER INFORMATION: Synthetic peptide

<400> SEQUENCE: 58

Phe Val Thr Asn Met Gly Ile Ile Ile Pro Asp Phe Ala Arg Ser Gly
1               5                   10                  15

Val Gln Met Asn
        20

<210> SEQ ID NO 59
<211> LENGTH: 20
<212> TYPE: PRT
<213> ORGANISM: Artificial Sequence
<220> FEATURE:
<223> OTHER INFORMATION: Synthetic peptide

<400> SEQUENCE: 59

Gly Val Gln Met Asn Thr Asn Phe Phe His Glu Ser Gly Leu Glu Ala
1               5                   10                  15
```

His Val Ala Leu
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic peptide

<400> SEQUENCE: 60

Ala His Val Ala Leu Lys Ala Gly Lys Leu Lys Phe Ile Ile Pro Ser
1               5                   10                  15

Pro Lys Arg Pro
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic peptide

<400> SEQUENCE: 61

Ser Pro Lys Arg Pro Val Lys Leu Leu Ser Gly Gly Asn Thr Leu His
1               5                   10                  15

Leu Val Ser Thr
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic peptide

<400> SEQUENCE: 62

His Leu Val Ser Thr Thr Lys Thr Glu Val Ile Pro Pro Leu Ile Glu
1               5                   10                  15

Asn Arg Gln Ser
            20

<210> SEQ ID NO 63
<211> LENGTH: 20
<212> TYPE: PRT
<213> ORGANISM: Artificial Sequence
<220> FEATURE:
<223> OTHER INFORMATION: Synthetic peptide

<400> SEQUENCE: 63

Glu Asn Arg Gln Ser Trp Ser Val Cys Lys Gln Val Phe Pro Gly Leu
1               5                   10                  15

Asn Tyr Cys Thr
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic peptide

<400> SEQUENCE: 64

Leu Asn Tyr Cys Thr Ser Gly Ala Tyr Ser Asn Ala Ser Ser Thr Asp
1               5                   10                  15

```
Ser Ala Ser Tyr
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic peptide

<400> SEQUENCE: 65

Asp Ser Ala Ser Tyr Tyr Pro Leu Thr Gly Asp Thr Arg Leu Glu Leu
1               5                   10                  15

Glu Leu Arg Pro
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic peptide

<400> SEQUENCE: 66

Leu Glu Leu Arg Pro Thr Gly Glu Ile Glu Gln Tyr Ser Val Ser Ala
1               5                   10                  15

Thr Tyr Glu Leu
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic peptide

<400> SEQUENCE: 67

Ala Thr Tyr Glu Leu Gln Arg Glu Asp Arg Ala Leu Val Asp Thr Leu
1               5                   10                  15

Lys Phe Val Thr
            20

<210> SEQ ID NO 68
<211> LENGTH: 20
<212> TYPE: PRT
<213> ORGANISM: Artificial Sequence
<220> FEATURE:
<223> OTHER INFORMATION: Synthetic peptide

<400> SEQUENCE: 68

Leu Lys Phe Val Thr Gln Ala Glu Gly Ala Lys Gln Thr Glu Ala Thr
1               5                   10                  15

Met Thr Phe Lys
            20

<210> SEQ ID NO 69
<211> LENGTH: 20
<212> TYPE: PRT
<213> ORGANISM: Artificial Sequence
<220> FEATURE:
<223> OTHER INFORMATION: Synthetic peptide

<400> SEQUENCE: 69

Thr Met Thr Phe Lys Tyr Asn Arg Gln Ser Met Thr Leu Ser Ser Glu
1               5                   10                  15
```

```
Val Gln Ile Pro
            20

<210> SEQ ID NO 70
<211> LENGTH: 20
<212> TYPE: PRT
<213> ORGANISM: Artificial Sequence
<220> FEATURE:
<223> OTHER INFORMATION: Synthetic peptide

<400> SEQUENCE: 70

Glu Val Gln Ile Pro Asp Phe Asp Val Asp Leu Gly Thr Ile Leu Arg
1               5                   10                  15

Val Asn Asp Glu
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic peptide

<400> SEQUENCE: 71

Arg Val Asn Asp Glu Ser Thr Glu Gly Lys Thr Ser Tyr Arg Leu Thr
1               5                   10                  15

Leu Asp Ile Gln
            20

<210> SEQ ID NO 72
<211> LENGTH: 20
<212> TYPE: PRT
<213> ORGANISM: Artificial Sequence
<220> FEATURE:
<223> OTHER INFORMATION: Synthetic peptide

<400> SEQUENCE: 72

Thr Leu Asp Ile Gln Asn Lys Lys Ile Thr Glu Val Ala Leu Met Gly
1               5                   10                  15

His Leu Ser Cys
            20

<210> SEQ ID NO 73
<211> LENGTH: 20
<212> TYPE: PRT
<213> ORGANISM: Artificial Sequence
<220> FEATURE:
<223> OTHER INFORMATION: Synthetic peptide

<400> SEQUENCE: 73

Gly His Leu Ser Cys Asp Thr Lys Glu Glu Arg Lys Ile Lys Gly Val
1               5                   10                  15

Ile Ser Ile Pro
            20

<210> SEQ ID NO 74
<211> LENGTH: 20
<212> TYPE: PRT
<213> ORGANISM: Artificial Sequence
<220> FEATURE:
<223> OTHER INFORMATION: Synthetic peptide

<400> SEQUENCE: 74

Val Ile Ser Ile Pro Arg Leu Gln Ala Glu Ala Arg Ser Glu Ile Leu
1               5                   10                  15
```

-continued

```
Ala His Trp Ser
            20

<210> SEQ ID NO 75
<211> LENGTH: 20
<212> TYPE: PRT
<213> ORGANISM: Artificial Sequence
<220> FEATURE:
<223> OTHER INFORMATION: Synthetic peptide

<400> SEQUENCE: 75

Leu Ala His Trp Ser Pro Ala Lys Leu Leu Gln Met Asp Ser Ser
1               5                   10                  15

Ala Thr Ala Tyr
            20

<210> SEQ ID NO 76
<211> LENGTH: 20
<212> TYPE: PRT
<213> ORGANISM: Artificial Sequence
<220> FEATURE:
<223> OTHER INFORMATION: Synthetic peptide

<400> SEQUENCE: 76

Ser Ala Thr Ala Tyr Gly Ser Thr Val Ser Lys Arg Val Ala Trp His
1               5                   10                  15

Tyr Asp Glu Glu
            20

<210> SEQ ID NO 77
<211> LENGTH: 20
<212> TYPE: PRT
<213> ORGANISM: Artificial Sequence
<220> FEATURE:
<223> OTHER INFORMATION: Synthetic peptide

<400> SEQUENCE: 77

His Tyr Asp Glu Glu Lys Ile Glu Phe Glu Trp Asn Thr Gly Thr Asn
1               5                   10                  15

Val Asp Thr Lys
            20

<210> SEQ ID NO 78
<211> LENGTH: 20
<212> TYPE: PRT
<213> ORGANISM: Artificial Sequence
<220> FEATURE:
<223> OTHER INFORMATION: Synthetic peptide

<400> SEQUENCE: 78

Asn Val Asp Thr Lys Lys Met Thr Ser Asn Phe Pro Val Asp Leu Ser
1               5                   10                  15

Asp Tyr Pro Lys
            20

<210> SEQ ID NO 79
<211> LENGTH: 20
<212> TYPE: PRT
<213> ORGANISM: Artificial Sequence
<220> FEATURE:
<223> OTHER INFORMATION: Synthetic peptide

<400> SEQUENCE: 79

Ser Asp Tyr Pro Lys Ser Leu His Met Tyr Ala Asn Arg Leu Leu Asp
1               5                   10                  15
```

His Arg Val Pro
            20

<210> SEQ ID NO 80
<211> LENGTH: 20
<212> TYPE: PRT
<213> ORGANISM: Artificial Sequence
<220> FEATURE:
<223> OTHER INFORMATION: Synthetic peptide

<400> SEQUENCE: 80

Asp His Arg Val Pro Glu Thr Asp Met Thr Phe Arg His Val Gly Ser
1               5                   10                  15

Lys Leu Ile Val
            20

<210> SEQ ID NO 81
<211> LENGTH: 20
<212> TYPE: PRT
<213> ORGANISM: Artificial Sequence
<220> FEATURE:
<223> OTHER INFORMATION: Synthetic peptide

<400> SEQUENCE: 81

Ser Lys Leu Ile Val Ala Met Ser Ser Trp Leu Gln Lys Ala Ser Gly
1               5                   10                  15

Ser Leu Pro Tyr
            20

<210> SEQ ID NO 82
<211> LENGTH: 20
<212> TYPE: PRT
<213> ORGANISM: Artificial Sequence
<220> FEATURE:
<223> OTHER INFORMATION: Synthetic peptide

<400> SEQUENCE: 82

Gly Ser Leu Pro Tyr Thr Gln Thr Leu Gln Asp His Leu Asn Ser Leu
1               5                   10                  15

Lys Glu Phe Asn
            20

<210> SEQ ID NO 83
<211> LENGTH: 20
<212> TYPE: PRT
<213> ORGANISM: Artificial Sequence
<220> FEATURE:
<223> OTHER INFORMATION: Synthetic peptide

<400> SEQUENCE: 83

Leu Lys Glu Phe Asn Leu Gln Asn Met Gly Leu Pro Asp Phe His Ile
1               5                   10                  15

Pro Glu Asn Leu
            20

<210> SEQ ID NO 84
<211> LENGTH: 20
<212> TYPE: PRT
<213> ORGANISM: Artificial Sequence
<220> FEATURE:
<223> OTHER INFORMATION: Synthetic peptide

<400> SEQUENCE: 84

Ile Pro Glu Asn Leu Phe Leu Lys Ser Asp Gly Arg Val Lys Tyr Thr
1               5                   10                  15

-continued

Leu Asn Lys Asn
            20

<210> SEQ ID NO 85
<211> LENGTH: 20
<212> TYPE: PRT
<213> ORGANISM: Artificial Sequence
<220> FEATURE:
<223> OTHER INFORMATION: Synthetic peptide

<400> SEQUENCE: 85

Thr Leu Asn Lys Asn Ser Leu Lys Ile Glu Ile Pro Leu Pro Phe Gly
1               5                   10                  15

Gly Lys Ser Ser
            20

<210> SEQ ID NO 86
<211> LENGTH: 20
<212> TYPE: PRT
<213> ORGANISM: Artificial Sequence
<220> FEATURE:
<223> OTHER INFORMATION: Synthetic peptide

<400> SEQUENCE: 86

Gly Gly Lys Ser Ser Arg Asp Leu Lys Met Leu Glu Thr Val Arg Thr
1               5                   10                  15

Pro Ala Leu His
            20

<210> SEQ ID NO 87
<211> LENGTH: 20
<212> TYPE: PRT
<213> ORGANISM: Artificial Sequence
<220> FEATURE:
<223> OTHER INFORMATION: Synthetic peptide

<400> SEQUENCE: 87

Thr Pro Ala Leu His Phe Lys Ser Val Gly Phe His Leu Pro Ser Arg
1               5                   10                  15

Glu Phe Gln Val
            20

<210> SEQ ID NO 88
<211> LENGTH: 20
<212> TYPE: PRT
<213> ORGANISM: Artificial Sequence
<220> FEATURE:
<223> OTHER INFORMATION: Synthetic peptide

<400> SEQUENCE: 88

Arg Glu Phe Gln Val Pro Thr Phe Thr Ile Pro Lys Leu Tyr Gln Leu
1               5                   10                  15

Gln Val Pro Leu
            20

<210> SEQ ID NO 89
<211> LENGTH: 20
<212> TYPE: PRT
<213> ORGANISM: Artificial Sequence
<220> FEATURE:
<223> OTHER INFORMATION: Synthetic peptide

<400> SEQUENCE: 89

Leu Gln Val Pro Leu Leu Gly Val Leu Asp Leu Ser Thr Asn Val Tyr
1               5                   10                  15

-continued

Ser Asn Leu Tyr
            20

<210> SEQ ID NO 90
<211> LENGTH: 20
<212> TYPE: PRT
<213> ORGANISM: Artificial Sequence
<220> FEATURE:
<223> OTHER INFORMATION: Synthetic peptide

<400> SEQUENCE: 90

Tyr Ser Asn Leu Tyr Asn Trp Ser Ala Ser Tyr Ser Gly Gly Asn Thr
1               5                   10                  15

Ser Thr Asp His
            20

<210> SEQ ID NO 91
<211> LENGTH: 20
<212> TYPE: PRT
<213> ORGANISM: Artificial Sequence
<220> FEATURE:
<223> OTHER INFORMATION: Synthetic peptide

<400> SEQUENCE: 91

Thr Ser Thr Asp His Phe Ser Leu Arg Ala Arg Tyr His Met Lys Ala
1               5                   10                  15

Asp Ser Val Val
            20

<210> SEQ ID NO 92
<211> LENGTH: 20
<212> TYPE: PRT
<213> ORGANISM: Artificial Sequence
<220> FEATURE:
<223> OTHER INFORMATION: Synthetic peptide

<400> SEQUENCE: 92

Ala Asp Ser Val Val Asp Leu Leu Ser Tyr Asn Val Gln Gly Ser Gly
1               5                   10                  15

Glu Thr Thr Tyr
            20

<210> SEQ ID NO 93
<211> LENGTH: 20
<212> TYPE: PRT
<213> ORGANISM: Artificial Sequence
<220> FEATURE:
<223> OTHER INFORMATION: Synthetic peptide

<400> SEQUENCE: 93

Gly Glu Thr Thr Tyr Asp His Lys Asn Thr Phe Thr Leu Ser Cys Asp
1               5                   10                  15

Gly Ser Leu Arg
            20

<210> SEQ ID NO 94
<211> LENGTH: 20
<212> TYPE: PRT
<213> ORGANISM: Artificial Sequence
<220> FEATURE:
<223> OTHER INFORMATION: Synthetic peptide

<400> SEQUENCE: 94

Asp Gly Ser Leu Arg His Lys Phe Leu Asp Ser Asn Ile Lys Phe Ser
1               5                   10                  15

His Val Glu Lys
            20

<210> SEQ ID NO 95
<211> LENGTH: 20
<212> TYPE: PRT
<213> ORGANISM: Artificial Sequence
<220> FEATURE:
<223> OTHER INFORMATION: Synthetic peptide

<400> SEQUENCE: 95

Ser His Val Glu Lys Leu Gly Asn Asn Pro Val Ser Lys Gly Leu Leu
1               5                   10                  15

Ile Phe Asp Ala
            20

<210> SEQ ID NO 96
<211> LENGTH: 20
<212> TYPE: PRT
<213> ORGANISM: Artificial Sequence
<220> FEATURE:
<223> OTHER INFORMATION: Synthetic peptide

<400> SEQUENCE: 96

Leu Ile Phe Asp Ala Ser Ser Ser Trp Gly Pro Gln Met Ser Ala Ser
1               5                   10                  15

Val His Leu Asp
            20

<210> SEQ ID NO 97
<211> LENGTH: 20
<212> TYPE: PRT
<213> ORGANISM: Artificial Sequence
<220> FEATURE:
<223> OTHER INFORMATION: Synthetic peptide

<400> SEQUENCE: 97

Ser Val His Leu Asp Ser Lys Lys Lys Gln His Leu Phe Val Lys Glu
1               5                   10                  15

Val Lys Ile Asp
            20

<210> SEQ ID NO 98
<211> LENGTH: 20
<212> TYPE: PRT
<213> ORGANISM: Artificial Sequence
<220> FEATURE:
<223> OTHER INFORMATION: Synthetic peptide

<400> SEQUENCE: 98

Glu Val Lys Ile Asp Gly Gln Phe Arg Val Ser Ser Phe Tyr Ala Lys
1               5                   10                  15

Gly Thr Tyr Gly
            20

<210> SEQ ID NO 99
<211> LENGTH: 20
<212> TYPE: PRT
<213> ORGANISM: Artificial Sequence
<220> FEATURE:
<223> OTHER INFORMATION: Synthetic peptide

<400> SEQUENCE: 99

Lys Gly Thr Tyr Gly Leu Ser Cys Gln Arg Asp Pro Asn Thr Gly Arg
1               5                   10                  15

Leu Asn Gly Glu
        20

<210> SEQ ID NO 100
<211> LENGTH: 20
<212> TYPE: PRT
<213> ORGANISM: Artificial Sequence
<220> FEATURE:
<223> OTHER INFORMATION: Synthetic peptide

<400> SEQUENCE: 100

Arg Leu Asn Gly Glu Ser Asn Leu Arg Phe Asn Ser Ser Tyr Leu Gln
1               5                   10                  15

Gly Thr Asn Gln
        20

<210> SEQ ID NO 101
<211> LENGTH: 20
<212> TYPE: PRT
<213> ORGANISM: Artificial Sequence
<220> FEATURE:
<223> OTHER INFORMATION: Synthetic peptide

<400> SEQUENCE: 101

Gln Gly Thr Asn Gln Ile Thr Gly Arg Tyr Glu Asp Gly Thr Leu Ser
1               5                   10                  15

Leu Thr Ser Thr
        20

<210> SEQ ID NO 102
<211> LENGTH: 20
<212> TYPE: PRT
<213> ORGANISM: Artificial Sequence
<220> FEATURE:
<223> OTHER INFORMATION: Synthetic peptide

<400> SEQUENCE: 102

Ser Leu Thr Ser Thr Ser Asp Leu Gln Ser Gly Ile Ile Lys Asn Thr
1               5                   10                  15

Ala Ser Leu Lys
        20

<210> SEQ ID NO 103
<211> LENGTH: 20
<212> TYPE: PRT
<213> ORGANISM: Artificial Sequence
<220> FEATURE:
<223> OTHER INFORMATION: Synthetic peptide

<400> SEQUENCE: 103

Thr Ala Ser Leu Lys Tyr Glu Asn Tyr Glu Leu Thr Leu Lys Ser Asp
1               5                   10                  15

Thr Asn Gly Lys
        20

<210> SEQ ID NO 104
<211> LENGTH: 20
<212> TYPE: PRT
<213> ORGANISM: Artificial Sequence
<220> FEATURE:
<223> OTHER INFORMATION: Synthetic peptide

<400> SEQUENCE: 104

Asp Thr Asn Gly Lys Tyr Lys Asn Phe Ala Thr Ser Asn Lys Met Asp
1               5                   10                  15

```
Met Thr Phe Ser
            20

<210> SEQ ID NO 105
<211> LENGTH: 20
<212> TYPE: PRT
<213> ORGANISM: Artificial Sequence
<220> FEATURE:
<223> OTHER INFORMATION: Synthetic peptide

<400> SEQUENCE: 105

Asp Met Thr Phe Ser Lys Gln Asn Ala Leu Leu Arg Ser Glu Tyr Gln
1               5                   10                  15

Ala Asp Tyr Glu
            20

<210> SEQ ID NO 106
<211> LENGTH: 20
<212> TYPE: PRT
<213> ORGANISM: Artificial Sequence
<220> FEATURE:
<223> OTHER INFORMATION: Synthetic peptide

<400> SEQUENCE: 106

Gln Ala Asp Tyr Glu Ser Leu Arg Phe Phe Ser Leu Leu Ser Gly Ser
1               5                   10                  15

Leu Asn Ser His
            20

<210> SEQ ID NO 107
<211> LENGTH: 20
<212> TYPE: PRT
<213> ORGANISM: Artificial Sequence
<220> FEATURE:
<223> OTHER INFORMATION: Synthetic peptide

<400> SEQUENCE: 107

Ser Leu Asn Ser His Gly Leu Glu Leu Asn Ala Asp Ile Leu Gly Thr
1               5                   10                  15

Asp Lys Ile Asn
            20

<210> SEQ ID NO 108
<211> LENGTH: 20
<212> TYPE: PRT
<213> ORGANISM: Artificial Sequence
<220> FEATURE:
<223> OTHER INFORMATION: Synthetic peptide

<400> SEQUENCE: 108

Thr Asp Lys Ile Asn Ser Gly Ala His Lys Ala Thr Leu Arg Ile Gly
1               5                   10                  15

Gln Asp Gly Ile
            20

<210> SEQ ID NO 109
<211> LENGTH: 20
<212> TYPE: PRT
<213> ORGANISM: Artificial Sequence
<220> FEATURE:
<223> OTHER INFORMATION: Synthetic peptide

<400> SEQUENCE: 109

Gly Gln Asp Gly Ile Ser Thr Ser Ala Thr Thr Asn Leu Lys Cys Ser
1               5                   10                  15
```

```
Leu Leu Val Leu
            20

<210> SEQ ID NO 110
<211> LENGTH: 20
<212> TYPE: PRT
<213> ORGANISM: Artificial Sequence
<220> FEATURE:
<223> OTHER INFORMATION: Synthetic peptide

<400> SEQUENCE: 110

Ser Leu Leu Val Leu Glu Asn Glu Leu Asn Ala Glu Leu Gly Leu Ser
1               5                  10                  15

Gly Ala Ser Met
            20

<210> SEQ ID NO 111
<211> LENGTH: 20
<212> TYPE: PRT
<213> ORGANISM: Artificial Sequence
<220> FEATURE:
<223> OTHER INFORMATION: Synthetic peptide

<400> SEQUENCE: 111

Ser Gly Ala Ser Met Lys Leu Thr Thr Asn Gly Arg Phe Arg Glu His
1               5                  10                  15

Asn Ala Lys Phe
            20

<210> SEQ ID NO 112
<211> LENGTH: 20
<212> TYPE: PRT
<213> ORGANISM: Artificial Sequence
<220> FEATURE:
<223> OTHER INFORMATION: Synthetic peptide

<400> SEQUENCE: 112

His Asn Ala Lys Phe Ser Leu Asp Gly Lys Ala Ala Leu Thr Glu Leu
1               5                  10                  15

Ser Leu Gly Ser
            20

<210> SEQ ID NO 113
<211> LENGTH: 20
<212> TYPE: PRT
<213> ORGANISM: Artificial Sequence
<220> FEATURE:
<223> OTHER INFORMATION: Synthetic peptide

<400> SEQUENCE: 113

Leu Ser Leu Gly Ser Ala Tyr Gln Ala Met Ile Leu Gly Val Asp Ser
1               5                  10                  15

Lys Asn Ile Phe
            20

<210> SEQ ID NO 114
<211> LENGTH: 20
<212> TYPE: PRT
<213> ORGANISM: Artificial Sequence
<220> FEATURE:
<223> OTHER INFORMATION: Synthetic peptide

<400> SEQUENCE: 114

Ser Lys Asn Ile Phe Asn Phe Lys Val Ser Gln Glu Gly Leu Lys Leu
1               5                  10                  15
```

Ser Asn Asp Met
            20

<210> SEQ ID NO 115
<211> LENGTH: 20
<212> TYPE: PRT
<213> ORGANISM: Artificial Sequence
<220> FEATURE:
<223> OTHER INFORMATION: Synthetic peptide

<400> SEQUENCE: 115

Leu Ser Asn Asp Met Met Gly Ser Tyr Ala Glu Met Lys Phe Asp His
1               5                   10                  15

Thr Asn Ser Leu
            20

<210> SEQ ID NO 116
<211> LENGTH: 20
<212> TYPE: PRT
<213> ORGANISM: Artificial Sequence
<220> FEATURE:
<223> OTHER INFORMATION: Synthetic peptide

<400> SEQUENCE: 116

His Thr Asn Ser Leu Asn Ile Ala Gly Leu Ser Leu Asp Phe Ser Ser
1               5                   10                  15

Lys Leu Asp Asn
            20

<210> SEQ ID NO 117
<211> LENGTH: 20
<212> TYPE: PRT
<213> ORGANISM: Artificial Sequence
<220> FEATURE:
<223> OTHER INFORMATION: Synthetic peptide

<400> SEQUENCE: 117

Ser Lys Leu Asp Asn Ile Tyr Ser Ser Asp Lys Phe Tyr Lys Gln Thr
1               5                   10                  15

Val Asn Leu Gln
            20

<210> SEQ ID NO 118
<211> LENGTH: 20
<212> TYPE: PRT
<213> ORGANISM: Artificial Sequence
<220> FEATURE:
<223> OTHER INFORMATION: Synthetic peptide

<400> SEQUENCE: 118

Thr Val Asn Leu Gln Leu Gln Pro Tyr Ser Leu Val Thr Thr Leu Asn
1               5                   10                  15

Ser Asp Leu Lys
            20

<210> SEQ ID NO 119
<211> LENGTH: 20
<212> TYPE: PRT
<213> ORGANISM: Artificial Sequence
<220> FEATURE:
<223> OTHER INFORMATION: Synthetic peptide

<400> SEQUENCE: 119

Asn Ser Asp Leu Lys Tyr Asn Ala Leu Asp Leu Thr Asn Asn Gly Lys
1               5                   10                  15

```
Leu Arg Leu Glu
            20

<210> SEQ ID NO 120
<211> LENGTH: 20
<212> TYPE: PRT
<213> ORGANISM: Artificial Sequence
<220> FEATURE:
<223> OTHER INFORMATION: Synthetic peptide

<400> SEQUENCE: 120

Lys Leu Arg Leu Glu Pro Leu Lys Leu His Val Ala Gly Asn Leu Lys
1               5                   10                  15

Gly Ala Tyr Gln
            20

<210> SEQ ID NO 121
<211> LENGTH: 20
<212> TYPE: PRT
<213> ORGANISM: Artificial Sequence
<220> FEATURE:
<223> OTHER INFORMATION: Synthetic peptide

<400> SEQUENCE: 121

Lys Gly Ala Tyr Gln Asn Asn Glu Ile Lys His Ile Tyr Ala Ile Ser
1               5                   10                  15

Ser Ala Ala Leu
            20

<210> SEQ ID NO 122
<211> LENGTH: 20
<212> TYPE: PRT
<213> ORGANISM: Artificial Sequence
<220> FEATURE:
<223> OTHER INFORMATION: Synthetic peptide

<400> SEQUENCE: 122

Ser Ser Ala Ala Leu Ser Ala Ser Tyr Lys Ala Asp Thr Val Ala Lys
1               5                   10                  15

Val Gln Gly Val
            20

<210> SEQ ID NO 123
<211> LENGTH: 20
<212> TYPE: PRT
<213> ORGANISM: Artificial Sequence
<220> FEATURE:
<223> OTHER INFORMATION: Synthetic peptide

<400> SEQUENCE: 123

Lys Val Gln Gly Val Glu Phe Ser His Arg Leu Asn Thr Asp Ile Ala
1               5                   10                  15

Gly Leu Ala Ser
            20

<210> SEQ ID NO 124
<211> LENGTH: 20
<212> TYPE: PRT
<213> ORGANISM: Artificial Sequence
<220> FEATURE:
<223> OTHER INFORMATION: Synthetic peptide

<400> SEQUENCE: 124

Ala Gly Leu Ala Ser Ala Ile Asp Met Ser Thr Asn Tyr Asn Ser Asp
1               5                   10                  15
```

Ser Leu His Phe
            20

<210> SEQ ID NO 125
<211> LENGTH: 20
<212> TYPE: PRT
<213> ORGANISM: Artificial Sequence
<220> FEATURE:
<223> OTHER INFORMATION: Synthetic peptide

<400> SEQUENCE: 125

Asp Ser Leu His Phe Ser Asn Val Phe Arg Ser Val Met Ala Pro Phe
1               5                   10                  15

Thr Met Thr Ile
            20

<210> SEQ ID NO 126
<211> LENGTH: 20
<212> TYPE: PRT
<213> ORGANISM: Artificial Sequence
<220> FEATURE:
<223> OTHER INFORMATION: Synthetic peptide

<400> SEQUENCE: 126

Phe Thr Met Thr Ile Asp Ala His Thr Asn Gly Asn Gly Lys Leu Ala
1               5                   10                  15

Leu Trp Gly Glu
            20

<210> SEQ ID NO 127
<211> LENGTH: 20
<212> TYPE: PRT
<213> ORGANISM: Artificial Sequence
<220> FEATURE:
<223> OTHER INFORMATION: Synthetic peptide

<400> SEQUENCE: 127

Ala Leu Trp Gly Glu His Thr Gly Gln Leu Tyr Ser Lys Phe Leu Leu
1               5                   10                  15

Lys Ala Glu Pro
            20

<210> SEQ ID NO 128
<211> LENGTH: 20
<212> TYPE: PRT
<213> ORGANISM: Artificial Sequence
<220> FEATURE:
<223> OTHER INFORMATION: Synthetic peptide

<400> SEQUENCE: 128

Leu Lys Ala Glu Pro Leu Ala Phe Thr Phe Ser His Asp Tyr Lys Gly
1               5                   10                  15

Ser Thr Ser His
            20

<210> SEQ ID NO 129
<211> LENGTH: 20
<212> TYPE: PRT
<213> ORGANISM: Artificial Sequence
<220> FEATURE:
<223> OTHER INFORMATION: Synthetic peptide

<400> SEQUENCE: 129

Gly Ser Thr Ser His His Leu Val Ser Arg Lys Ser Ile Ser Ala Ala
1               5                   10                  15

```
Leu Glu His Lys
            20

<210> SEQ ID NO 130
<211> LENGTH: 20
<212> TYPE: PRT
<213> ORGANISM: Artificial Sequence
<220> FEATURE:
<223> OTHER INFORMATION: Synthetic peptide

<400> SEQUENCE: 130

Ala Leu Glu His Lys Val Ser Ala Leu Leu Thr Pro Ala Glu Gln Thr
1               5                  10                  15

Gly Thr Trp Lys
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic peptide

<400> SEQUENCE: 131

Thr Gly Thr Trp Lys Leu Lys Thr Gln Phe Asn Asn Asn Glu Tyr Ser
1               5                  10                  15

Gln Asp Leu Asp
            20

<210> SEQ ID NO 132
<211> LENGTH: 20
<212> TYPE: PRT
<213> ORGANISM: Artificial Sequence
<220> FEATURE:
<223> OTHER INFORMATION: Synthetic peptide

<400> SEQUENCE: 132

Ser Gln Asp Leu Asp Ala Tyr Asn Thr Lys Asp Lys Ile Gly Val Glu
1               5                  10                  15

Leu Thr Gly Arg
            20

<210> SEQ ID NO 133
<211> LENGTH: 20
<212> TYPE: PRT
<213> ORGANISM: Artificial Sequence
<220> FEATURE:
<223> OTHER INFORMATION: Synthetic peptide

<400> SEQUENCE: 133

Glu Leu Thr Gly Arg Thr Leu Ala Asp Leu Thr Leu Leu Asp Ser Pro
1               5                  10                  15

Ile Lys Val Pro
            20

<210> SEQ ID NO 134
<211> LENGTH: 20
<212> TYPE: PRT
<213> ORGANISM: Artificial Sequence
<220> FEATURE:
<223> OTHER INFORMATION: Synthetic peptide

<400> SEQUENCE: 134

Pro Ile Lys Val Pro Leu Leu Leu Ser Glu Pro Ile Asn Ile Ile Asp
1               5                  10                  15
```

```
Ala Leu Glu Met
            20

<210> SEQ ID NO 135
<211> LENGTH: 20
<212> TYPE: PRT
<213> ORGANISM: Artificial Sequence
<220> FEATURE:
<223> OTHER INFORMATION: Synthetic peptide

<400> SEQUENCE: 135

Asp Ala Leu Glu Met Arg Asp Ala Val Glu Lys Pro Gln Glu Phe Thr
1               5                   10                  15

Ile Val Ala Phe
            20

<210> SEQ ID NO 136
<211> LENGTH: 20
<212> TYPE: PRT
<213> ORGANISM: Artificial Sequence
<220> FEATURE:
<223> OTHER INFORMATION: Synthetic peptide

<400> SEQUENCE: 136

Thr Ile Val Ala Phe Val Lys Tyr Asp Lys Asn Gln Asp Val His Ser
1               5                   10                  15

Ile Asn Leu Pro
            20

<210> SEQ ID NO 137
<211> LENGTH: 20
<212> TYPE: PRT
<213> ORGANISM: Artificial Sequence
<220> FEATURE:
<223> OTHER INFORMATION: Synthetic peptide

<400> SEQUENCE: 137

Ser Ile Asn Leu Pro Phe Phe Glu Thr Leu Gln Glu Tyr Phe Glu Arg
1               5                   10                  15

Asn Arg Gln Thr
            20

<210> SEQ ID NO 138
<211> LENGTH: 20
<212> TYPE: PRT
<213> ORGANISM: Artificial Sequence
<220> FEATURE:
<223> OTHER INFORMATION: Synthetic peptide

<400> SEQUENCE: 138

Arg Asn Arg Gln Thr Ile Ile Val Val Val Glu Asn Val Gln Arg Asn
1               5                   10                  15

Leu Lys His Ile
            20

<210> SEQ ID NO 139
<211> LENGTH: 20
<212> TYPE: PRT
<213> ORGANISM: Artificial Sequence
<220> FEATURE:
<223> OTHER INFORMATION: Synthetic peptide

<400> SEQUENCE: 139

Asn Leu Lys His Ile Asn Ile Asp Gln Phe Val Arg Lys Tyr Arg Ala
1               5                   10                  15
```

Ala Leu Gly Lys
            20

<210> SEQ ID NO 140
<211> LENGTH: 20
<212> TYPE: PRT
<213> ORGANISM: Artificial Sequence
<220> FEATURE:
<223> OTHER INFORMATION: Synthetic peptide

<400> SEQUENCE: 140

Ala Ala Leu Gly Lys Leu Pro Gln Gln Ala Asn Asp Tyr Leu Asn Ser
1               5                   10                  15

Phe Asn Trp Glu
            20

<210> SEQ ID NO 141
<211> LENGTH: 20
<212> TYPE: PRT
<213> ORGANISM: Artificial Sequence
<220> FEATURE:
<223> OTHER INFORMATION: Synthetic peptide

<400> SEQUENCE: 141

Ser Phe Asn Trp Glu Arg Gln Val Ser His Ala Lys Glu Lys Leu Thr
1               5                   10                  15

Ala Leu Thr Lys
            20

<210> SEQ ID NO 142
<211> LENGTH: 20
<212> TYPE: PRT
<213> ORGANISM: Artificial Sequence
<220> FEATURE:
<223> OTHER INFORMATION: Synthetic peptide

<400> SEQUENCE: 142

Thr Ala Leu Thr Lys Lys Tyr Arg Ile Thr Glu Asn Asp Ile Gln Ile
1               5                   10                  15

Ala Leu Asp Asp
            20

<210> SEQ ID NO 143
<211> LENGTH: 20
<212> TYPE: PRT
<213> ORGANISM: Artificial Sequence
<220> FEATURE:
<223> OTHER INFORMATION: Synthetic peptide

<400> SEQUENCE: 143

Ile Ala Leu Asp Asp Ala Lys Ile Asn Phe Asn Glu Lys Leu Ser Gln
1               5                   10                  15

Leu Gln Thr Tyr
            20

<210> SEQ ID NO 144
<211> LENGTH: 20
<212> TYPE: PRT
<213> ORGANISM: Artificial Sequence
<220> FEATURE:
<223> OTHER INFORMATION: Synthetic peptide

<400> SEQUENCE: 144

Gln Leu Gln Thr Tyr Met Ile Gln Phe Asp Gln Tyr Ile Lys Asp Ser
1               5                   10                  15

```
Tyr Asp Leu His
            20

<210> SEQ ID NO 145
<211> LENGTH: 20
<212> TYPE: PRT
<213> ORGANISM: Artificial Sequence
<220> FEATURE:
<223> OTHER INFORMATION: Synthetic peptide

<400> SEQUENCE: 145

Ser Tyr Asp Leu His Asp Leu Lys Ile Ala Ile Ala Asn Ile Ile Asp
1               5                   10                  15

Glu Ile Ile Glu
            20

<210> SEQ ID NO 146
<211> LENGTH: 20
<212> TYPE: PRT
<213> ORGANISM: Artificial Sequence
<220> FEATURE:
<223> OTHER INFORMATION: Synthetic peptide

<400> SEQUENCE: 146

Asp Glu Ile Ile Glu Lys Leu Lys Ser Leu Asp Glu His Tyr His Ile
1               5                   10                  15

Arg Val Asn Leu
            20

<210> SEQ ID NO 147
<211> LENGTH: 20
<212> TYPE: PRT
<213> ORGANISM: Artificial Sequence
<220> FEATURE:
<223> OTHER INFORMATION: Synthetic peptide

<400> SEQUENCE: 147

Ile Arg Val Asn Leu Val Lys Thr Ile His Asp Leu His Leu Phe Ile
1               5                   10                  15

Glu Asn Ile Asp
            20

<210> SEQ ID NO 148
<211> LENGTH: 20
<212> TYPE: PRT
<213> ORGANISM: Artificial Sequence
<220> FEATURE:
<223> OTHER INFORMATION: Synthetic peptide

<400> SEQUENCE: 148

Ile Glu Asn Ile Asp Phe Asn Lys Ser Gly Ser Ser Thr Ala Ser Trp
1               5                   10                  15

Ile Gln Asn Val
            20

<210> SEQ ID NO 149
<211> LENGTH: 20
<212> TYPE: PRT
<213> ORGANISM: Artificial Sequence
<220> FEATURE:
<223> OTHER INFORMATION: Synthetic peptide

<400> SEQUENCE: 149

Trp Ile Gln Asn Val Asp Thr Lys Tyr Gln Ile Arg Ile Gln Ile Gln
1               5                   10                  15
```

```
Glu Lys Leu Gln
            20

<210> SEQ ID NO 150
<211> LENGTH: 20
<212> TYPE: PRT
<213> ORGANISM: Artificial Sequence
<220> FEATURE:
<223> OTHER INFORMATION: Synthetic peptide

<400> SEQUENCE: 150

Gln Glu Lys Leu Gln Gln Leu Lys Arg His Ile Gln Asn Ile Asp Ile
1               5                   10                  15

Gln His Leu Ala
            20

<210> SEQ ID NO 151
<211> LENGTH: 20
<212> TYPE: PRT
<213> ORGANISM: Artificial Sequence
<220> FEATURE:
<223> OTHER INFORMATION: Synthetic peptide

<400> SEQUENCE: 151

Ile Gln His Leu Ala Gly Lys Leu Lys Gln His Ile Glu Ala Ile Asp
1               5                   10                  15

Val Arg Val Leu
            20

<210> SEQ ID NO 152
<211> LENGTH: 20
<212> TYPE: PRT
<213> ORGANISM: Artificial Sequence
<220> FEATURE:
<223> OTHER INFORMATION: Synthetic peptide

<400> SEQUENCE: 152

Asp Val Arg Val Leu Leu Asp Gln Leu Gly Thr Thr Ile Ser Phe Glu
1               5                   10                  15

Arg Ile Asn Asp
            20

<210> SEQ ID NO 153
<211> LENGTH: 20
<212> TYPE: PRT
<213> ORGANISM: Artificial Sequence
<220> FEATURE:
<223> OTHER INFORMATION: Synthetic peptide

<400> SEQUENCE: 153

Glu Arg Ile Asn Asp Val Leu Glu His Val Lys His Phe Val Ile Asn
1               5                   10                  15

Leu Ile Gly Asp
            20

<210> SEQ ID NO 154
<211> LENGTH: 20
<212> TYPE: PRT
<213> ORGANISM: Artificial Sequence
<220> FEATURE:
<223> OTHER INFORMATION: Synthetic peptide

<400> SEQUENCE: 154

Asn Leu Ile Gly Asp Phe Glu Val Ala Glu Lys Ile Asn Ala Phe Arg
1               5                   10                  15
```

```
Ala Lys Val His
            20

<210> SEQ ID NO 155
<211> LENGTH: 20
<212> TYPE: PRT
<213> ORGANISM: Artificial Sequence
<220> FEATURE:
<223> OTHER INFORMATION: Synthetic peptide

<400> SEQUENCE: 155

Arg Ala Lys Val His Glu Leu Ile Glu Arg Tyr Glu Val Asp Gln Gln
1               5                   10                  15

Ile Gln Val Leu
            20

<210> SEQ ID NO 156
<211> LENGTH: 20
<212> TYPE: PRT
<213> ORGANISM: Artificial Sequence
<220> FEATURE:
<223> OTHER INFORMATION: Synthetic peptide

<400> SEQUENCE: 156

Gln Ile Gln Val Leu Met Asp Lys Leu Val Glu Leu Thr His Gln Tyr
1               5                   10                  15

Lys Leu Lys Glu
            20

<210> SEQ ID NO 157
<211> LENGTH: 20
<212> TYPE: PRT
<213> ORGANISM: Artificial Sequence
<220> FEATURE:
<223> OTHER INFORMATION: Synthetic peptide

<400> SEQUENCE: 157

Tyr Lys Leu Lys Glu Thr Ile Gln Lys Leu Ser Asn Val Leu Gln Gln
1               5                   10                  15

Val Lys Ile Lys
            20

<210> SEQ ID NO 158
<211> LENGTH: 20
<212> TYPE: PRT
<213> ORGANISM: Artificial Sequence
<220> FEATURE:
<223> OTHER INFORMATION: Synthetic peptide

<400> SEQUENCE: 158

Gln Val Lys Ile Lys Asp Tyr Phe Glu Lys Leu Val Gly Phe Ile Asp
1               5                   10                  15

Asp Ala Val Lys
            20

<210> SEQ ID NO 159
<211> LENGTH: 20
<212> TYPE: PRT
<213> ORGANISM: Artificial Sequence
<220> FEATURE:
<223> OTHER INFORMATION: Synthetic peptide

<400> SEQUENCE: 159

Asp Asp Ala Val Lys Lys Leu Asn Glu Leu Ser Phe Lys Thr Phe Ile
1               5                   10                  15
```

```
Glu Asp Val Asn
            20

<210> SEQ ID NO 160
<211> LENGTH: 20
<212> TYPE: PRT
<213> ORGANISM: Artificial Sequence
<220> FEATURE:
<223> OTHER INFORMATION: Synthetic peptide

<400> SEQUENCE: 160

Ile Glu Asp Val Asn Lys Phe Leu Asp Met Leu Ile Lys Lys Leu Lys
1               5                   10                  15

Ser Phe Asp Tyr
            20

<210> SEQ ID NO 161
<211> LENGTH: 20
<212> TYPE: PRT
<213> ORGANISM: Artificial Sequence
<220> FEATURE:
<223> OTHER INFORMATION: Synthetic peptide

<400> SEQUENCE: 161

Lys Ser Phe Asp Tyr His Gln Phe Val Asp Glu Thr Asn Asp Lys Ile
1               5                   10                  15

Arg Glu Val Thr
            20

<210> SEQ ID NO 162
<211> LENGTH: 20
<212> TYPE: PRT
<213> ORGANISM: Artificial Sequence
<220> FEATURE:
<223> OTHER INFORMATION: Synthetic peptide

<400> SEQUENCE: 162

Ile Arg Glu Val Thr Gln Arg Leu Asn Gly Glu Ile Gln Ala Leu Glu
1               5                   10                  15

Leu Pro Gln Lys
            20

<210> SEQ ID NO 163
<211> LENGTH: 20
<212> TYPE: PRT
<213> ORGANISM: Artificial Sequence
<220> FEATURE:
<223> OTHER INFORMATION: Synthetic peptide

<400> SEQUENCE: 163

Glu Leu Pro Gln Lys Ala Glu Ala Leu Lys Leu Phe Leu Glu Glu Thr
1               5                   10                  15

Lys Ala Thr Val
            20

<210> SEQ ID NO 164
<211> LENGTH: 20
<212> TYPE: PRT
<213> ORGANISM: Artificial Sequence
<220> FEATURE:
<223> OTHER INFORMATION: Synthetic peptide

<400> SEQUENCE: 164

Thr Lys Ala Thr Val Ala Val Tyr Leu Glu Ser Leu Gln Asp Thr Lys
1               5                   10                  15
```

Ile Thr Leu Ile
            20

<210> SEQ ID NO 165
<211> LENGTH: 20
<212> TYPE: PRT
<213> ORGANISM: Artificial Sequence
<220> FEATURE:
<223> OTHER INFORMATION: Synthetic peptide

<400> SEQUENCE: 165

Lys Ile Thr Leu Ile Ile Asn Trp Leu Gln Glu Ala Leu Ser Ser Ala
1               5                   10                  15

Ser Leu Ala His
            20

<210> SEQ ID NO 166
<211> LENGTH: 20
<212> TYPE: PRT
<213> ORGANISM: Artificial Sequence
<220> FEATURE:
<223> OTHER INFORMATION: Synthetic peptide

<400> SEQUENCE: 166

Ala Ser Leu Ala His Met Lys Ala Lys Phe Arg Glu Thr Leu Glu Asp
1               5                   10                  15

Thr Arg Asp Arg
            20

<210> SEQ ID NO 167
<211> LENGTH: 20
<212> TYPE: PRT
<213> ORGANISM: Artificial Sequence
<220> FEATURE:
<223> OTHER INFORMATION: Synthetic peptide

<400> SEQUENCE: 167

Asp Thr Arg Asp Arg Met Tyr Gln Met Asp Ile Gln Gln Glu Leu Gln
1               5                   10                  15

Arg Tyr Leu Ser
            20

<210> SEQ ID NO 168
<211> LENGTH: 20
<212> TYPE: PRT
<213> ORGANISM: Artificial Sequence
<220> FEATURE:
<223> OTHER INFORMATION: Synthetic peptide

<400> SEQUENCE: 168

Gln Arg Tyr Leu Ser Leu Val Gly Gln Val Tyr Ser Thr Leu Val Thr
1               5                   10                  15

Tyr Ile Ser Asp
            20

<210> SEQ ID NO 169
<211> LENGTH: 20
<212> TYPE: PRT
<213> ORGANISM: Artificial Sequence
<220> FEATURE:
<223> OTHER INFORMATION: Synthetic peptide

<400> SEQUENCE: 169

Thr Tyr Ile Ser Asp Trp Trp Thr Leu Ala Ala Lys Asn Leu Thr Asp
1               5                   10                  15

```
Phe Ala Glu Gln
        20

<210> SEQ ID NO 170
<211> LENGTH: 20
<212> TYPE: PRT
<213> ORGANISM: Artificial Sequence
<220> FEATURE:
<223> OTHER INFORMATION: Synthetic peptide

<400> SEQUENCE: 170

Asp Phe Ala Glu Gln Tyr Ser Ile Gln Asp Trp Ala Lys Arg Met Lys
1               5                   10                  15

Ala Leu Val Glu
        20

<210> SEQ ID NO 171
<211> LENGTH: 20
<212> TYPE: PRT
<213> ORGANISM: Artificial Sequence
<220> FEATURE:
<223> OTHER INFORMATION: Synthetic peptide

<400> SEQUENCE: 171

Lys Ala Leu Val Glu Gln Gly Phe Thr Val Pro Glu Ile Lys Thr Ile
1               5                   10                  15

Leu Gly Thr Met
        20

<210> SEQ ID NO 172
<211> LENGTH: 20
<212> TYPE: PRT
<213> ORGANISM: Artificial Sequence
<220> FEATURE:
<223> OTHER INFORMATION: Synthetic peptide

<400> SEQUENCE: 172

Ile Leu Gly Thr Met Pro Ala Phe Glu Val Ser Leu Gln Ala Leu Gln
1               5                   10                  15

Lys Ala Thr Phe
        20

<210> SEQ ID NO 173
<211> LENGTH: 20
<212> TYPE: PRT
<213> ORGANISM: Artificial Sequence
<220> FEATURE:
<223> OTHER INFORMATION: Synthetic peptide

<400> SEQUENCE: 173

Gln Lys Ala Thr Phe Gln Thr Pro Asp Phe Ile Val Pro Leu Thr Asp
1               5                   10                  15

Leu Arg Ile Pro
        20

<210> SEQ ID NO 174
<211> LENGTH: 20
<212> TYPE: PRT
<213> ORGANISM: Artificial Sequence
<220> FEATURE:
<223> OTHER INFORMATION: Synthetic peptide

<400> SEQUENCE: 174

Asp Leu Arg Ile Pro Ser Val Gln Ile Asn Phe Lys Asp Leu Lys Asn
1               5                   10                  15
```

Ile Lys Ile Pro
            20

<210> SEQ ID NO 175
<211> LENGTH: 20
<212> TYPE: PRT
<213> ORGANISM: Artificial Sequence
<220> FEATURE:
<223> OTHER INFORMATION: Synthetic peptide

<400> SEQUENCE: 175

Asn Ile Lys Ile Pro Ser Arg Phe Ser Thr Pro Glu Phe Thr Ile Leu
1               5                   10                  15

Asn Thr Phe His
            20

<210> SEQ ID NO 176
<211> LENGTH: 20
<212> TYPE: PRT
<213> ORGANISM: Artificial Sequence
<220> FEATURE:
<223> OTHER INFORMATION: Synthetic peptide

<400> SEQUENCE: 176

Leu Asn Thr Phe His Ile Pro Ser Phe Thr Ile Asp Phe Val Glu Met
1               5                   10                  15

Lys Val Lys Ile
            20

<210> SEQ ID NO 177
<211> LENGTH: 20
<212> TYPE: PRT
<213> ORGANISM: Artificial Sequence
<220> FEATURE:
<223> OTHER INFORMATION: Synthetic peptide

<400> SEQUENCE: 177

Met Lys Val Lys Ile Ile Arg Thr Ile Asp Gln Met Gln Asn Ser Glu
1               5                   10                  15

Leu Gln Trp Pro
            20

<210> SEQ ID NO 178
<211> LENGTH: 20
<212> TYPE: PRT
<213> ORGANISM: Artificial Sequence
<220> FEATURE:
<223> OTHER INFORMATION: Synthetic peptide

<400> SEQUENCE: 178

Glu Leu Gln Trp Pro Val Pro Asp Ile Tyr Leu Arg Asp Leu Lys Val
1               5                   10                  15

Glu Asp Ile Pro
            20

<210> SEQ ID NO 179
<211> LENGTH: 20
<212> TYPE: PRT
<213> ORGANISM: Artificial Sequence
<220> FEATURE:
<223> OTHER INFORMATION: Synthetic peptide

<400> SEQUENCE: 179

Val Glu Asp Ile Pro Leu Ala Arg Ile Thr Leu Pro Asp Phe Arg Leu
1               5                   10                  15

```
Pro Glu Ile Ala
            20

<210> SEQ ID NO 180
<211> LENGTH: 20
<212> TYPE: PRT
<213> ORGANISM: Artificial Sequence
<220> FEATURE:
<223> OTHER INFORMATION: Synthetic peptide

<400> SEQUENCE: 180

Leu Pro Glu Ile Ala Ile Pro Glu Phe Ile Ile Pro Thr Leu Asn Leu
1               5                   10                  15

Asn Asp Phe Gln
            20

<210> SEQ ID NO 181
<211> LENGTH: 20
<212> TYPE: PRT
<213> ORGANISM: Artificial Sequence
<220> FEATURE:
<223> OTHER INFORMATION: Synthetic peptide

<400> SEQUENCE: 181

Leu Asn Asp Phe Gln Val Pro Asp Leu His Ile Pro Glu Phe Gln Leu
1               5                   10                  15

Pro His Ile Ser
            20

<210> SEQ ID NO 182
<211> LENGTH: 20
<212> TYPE: PRT
<213> ORGANISM: Artificial Sequence
<220> FEATURE:
<223> OTHER INFORMATION: Synthetic peptide

<400> SEQUENCE: 182

Leu Pro His Ile Ser His Thr Ile Glu Val Pro Thr Phe Gly Lys Leu
1               5                   10                  15

Tyr Ser Ile Leu
            20

<210> SEQ ID NO 183
<211> LENGTH: 20
<212> TYPE: PRT
<213> ORGANISM: Artificial Sequence
<220> FEATURE:
<223> OTHER INFORMATION: Synthetic peptide

<400> SEQUENCE: 183

Leu Tyr Ser Ile Leu Lys Ile Gln Ser Pro Leu Phe Thr Leu Asp Ala
1               5                   10                  15

Asn Ala Asp Ile
            20

<210> SEQ ID NO 184
<211> LENGTH: 20
<212> TYPE: PRT
<213> ORGANISM: Artificial Sequence
<220> FEATURE:
<223> OTHER INFORMATION: Synthetic peptide

<400> SEQUENCE: 184

Ala Asn Ala Asp Ile Gly Asn Gly Thr Thr Ser Ala Asn Glu Ala Gly
1               5                   10                  15
```

```
Ile Ala Ala Ser
            20

<210> SEQ ID NO 185
<211> LENGTH: 20
<212> TYPE: PRT
<213> ORGANISM: Artificial Sequence
<220> FEATURE:
<223> OTHER INFORMATION: Synthetic peptide

<400> SEQUENCE: 185

Gly Ile Ala Ala Ser Ile Thr Ala Lys Gly Glu Ser Lys Leu Glu Val
1               5                   10                  15

Leu Asn Phe Asp
            20

<210> SEQ ID NO 186
<211> LENGTH: 20
<212> TYPE: PRT
<213> ORGANISM: Artificial Sequence
<220> FEATURE:
<223> OTHER INFORMATION: Synthetic peptide

<400> SEQUENCE: 186

Val Leu Asn Phe Asp Phe Gln Ala Asn Ala Gln Leu Ser Asn Pro Lys
1               5                   10                  15

Ile Asn Pro Leu
            20

<210> SEQ ID NO 187
<211> LENGTH: 20
<212> TYPE: PRT
<213> ORGANISM: Artificial Sequence
<220> FEATURE:
<223> OTHER INFORMATION: Synthetic peptide

<400> SEQUENCE: 187

Lys Ile Asn Pro Leu Ala Leu Lys Glu Ser Val Lys Phe Ser Ser Lys
1               5                   10                  15

Tyr Leu Arg Thr
            20

<210> SEQ ID NO 188
<211> LENGTH: 20
<212> TYPE: PRT
<213> ORGANISM: Artificial Sequence
<220> FEATURE:
<223> OTHER INFORMATION: Synthetic peptide

<400> SEQUENCE: 188

Lys Tyr Leu Arg Thr Glu His Gly Ser Glu Met Leu Phe Phe Gly Asn
1               5                   10                  15

Ala Ile Glu Gly
            20

<210> SEQ ID NO 189
<211> LENGTH: 20
<212> TYPE: PRT
<213> ORGANISM: Artificial Sequence
<220> FEATURE:
<223> OTHER INFORMATION: Synthetic peptide

<400> SEQUENCE: 189

Asn Ala Ile Glu Gly Lys Ser Asn Thr Val Ala Ser Leu His Thr Glu
1               5                   10                  15
```

Lys Asn Thr Leu
            20

<210> SEQ ID NO 190
<211> LENGTH: 20
<212> TYPE: PRT
<213> ORGANISM: Artificial Sequence
<220> FEATURE:
<223> OTHER INFORMATION: Synthetic peptide

<400> SEQUENCE: 190

Glu Lys Asn Thr Leu Glu Leu Ser Asn Gly Val Ile Val Lys Ile Asn
1               5                   10                  15

Asn Gln Leu Thr
            20

<210> SEQ ID NO 191
<211> LENGTH: 20
<212> TYPE: PRT
<213> ORGANISM: Artificial Sequence
<220> FEATURE:
<223> OTHER INFORMATION: Synthetic peptide

<400> SEQUENCE: 191

Asn Asn Gln Leu Thr Leu Asp Ser Asn Thr Lys Tyr Phe His Lys Leu
1               5                   10                  15

Asn Ile Pro Lys
            20

<210> SEQ ID NO 192
<211> LENGTH: 20
<212> TYPE: PRT
<213> ORGANISM: Artificial Sequence
<220> FEATURE:
<223> OTHER INFORMATION: Synthetic peptide

<400> SEQUENCE: 192

Leu Asn Ile Pro Lys Leu Asp Phe Ser Ser Gln Ala Asp Leu Arg Asn
1               5                   10                  15

Glu Ile Lys Thr
            20

<210> SEQ ID NO 193
<211> LENGTH: 20
<212> TYPE: PRT
<213> ORGANISM: Artificial Sequence
<220> FEATURE:
<223> OTHER INFORMATION: Synthetic peptide

<400> SEQUENCE: 193

Asn Glu Ile Lys Thr Leu Leu Lys Ala Gly His Ile Ala Trp Thr Ser
1               5                   10                  15

Ser Gly Lys Gly
            20

<210> SEQ ID NO 194
<211> LENGTH: 20
<212> TYPE: PRT
<213> ORGANISM: Artificial Sequence
<220> FEATURE:
<223> OTHER INFORMATION: Synthetic peptide

<400> SEQUENCE: 194

Ser Ser Gly Lys Gly Ser Trp Lys Trp Ala Cys Pro Arg Phe Ser Asp
1               5                   10                  15

Glu Gly Thr His
            20

<210> SEQ ID NO 195
<211> LENGTH: 20
<212> TYPE: PRT
<213> ORGANISM: Artificial Sequence
<220> FEATURE:
<223> OTHER INFORMATION: Synthetic peptide

<400> SEQUENCE: 195

Asp Glu Gly Thr His Glu Ser Gln Ile Ser Phe Thr Ile Glu Gly Pro
1               5                   10                  15

Leu Thr Ser Phe
            20

<210> SEQ ID NO 196
<211> LENGTH: 20
<212> TYPE: PRT
<213> ORGANISM: Artificial Sequence
<220> FEATURE:
<223> OTHER INFORMATION: Synthetic peptide

<400> SEQUENCE: 196

Pro Leu Thr Ser Phe Gly Leu Ser Asn Lys Ile Asn Ser Lys His Leu
1               5                   10                  15

Arg Val Asn Gln
            20

<210> SEQ ID NO 197
<211> LENGTH: 20
<212> TYPE: PRT
<213> ORGANISM: Artificial Sequence
<220> FEATURE:
<223> OTHER INFORMATION: Synthetic peptide

<400> SEQUENCE: 197

Leu Arg Val Asn Gln Asn Leu Val Tyr Glu Ser Gly Ser Leu Asn Phe
1               5                   10                  15

Ser Lys Leu Glu
            20

<210> SEQ ID NO 198
<211> LENGTH: 20
<212> TYPE: PRT
<213> ORGANISM: Artificial Sequence
<220> FEATURE:
<223> OTHER INFORMATION: Synthetic peptide

<400> SEQUENCE: 198

Phe Ser Lys Leu Glu Ile Gln Ser Gln Val Asp Ser Gln His Val Gly
1               5                   10                  15

His Ser Val Leu
            20

<210> SEQ ID NO 199
<211> LENGTH: 20
<212> TYPE: PRT
<213> ORGANISM: Artificial Sequence
<220> FEATURE:
<223> OTHER INFORMATION: Synthetic peptide

<400> SEQUENCE: 199

Gly His Ser Val Leu Thr Ala Lys Gly Met Ala Leu Phe Gly Glu Gly
1               5                   10                  15

```
Lys Ala Glu Phe
            20

<210> SEQ ID NO 200
<211> LENGTH: 20
<212> TYPE: PRT
<213> ORGANISM: Artificial Sequence
<220> FEATURE:
<223> OTHER INFORMATION: Synthetic peptide

<400> SEQUENCE: 200

Gly Lys Ala Glu Phe Thr Gly Arg His Asp Ala His Leu Asn Gly Lys
1               5                   10                  15

Val Ile Gly Thr
            20

<210> SEQ ID NO 201
<211> LENGTH: 20
<212> TYPE: PRT
<213> ORGANISM: Artificial Sequence
<220> FEATURE:
<223> OTHER INFORMATION: Synthetic peptide

<400> SEQUENCE: 201

Lys Val Ile Gly Thr Leu Lys Asn Ser Leu Phe Phe Ser Ala Gln Pro
1               5                   10                  15

Phe Glu Ile Thr
            20

<210> SEQ ID NO 202
<211> LENGTH: 20
<212> TYPE: PRT
<213> ORGANISM: Artificial Sequence
<220> FEATURE:
<223> OTHER INFORMATION: Synthetic peptide

<400> SEQUENCE: 202

Pro Phe Glu Ile Thr Ala Ser Thr Asn Asn Glu Gly Asn Leu Lys Val
1               5                   10                  15

Arg Phe Pro Leu
            20

<210> SEQ ID NO 203
<211> LENGTH: 20
<212> TYPE: PRT
<213> ORGANISM: Artificial Sequence
<220> FEATURE:
<223> OTHER INFORMATION: Synthetic peptide

<400> SEQUENCE: 203

Val Arg Phe Pro Leu Arg Leu Thr Gly Lys Ile Asp Phe Leu Asn Asn
1               5                   10                  15

Tyr Ala Leu Phe
            20

<210> SEQ ID NO 204
<211> LENGTH: 20
<212> TYPE: PRT
<213> ORGANISM: Artificial Sequence
<220> FEATURE:
<223> OTHER INFORMATION: Synthetic peptide

<400> SEQUENCE: 204

Asn Tyr Ala Leu Phe Leu Ser Pro Ser Ala Gln Gln Ala Ser Trp Gln
1               5                   10                  15
```

```
Val Ser Ala Arg
            20

<210> SEQ ID NO 205
<211> LENGTH: 20
<212> TYPE: PRT
<213> ORGANISM: Artificial Sequence
<220> FEATURE:
<223> OTHER INFORMATION: Synthetic peptide

<400> SEQUENCE: 205

Gln Val Ser Ala Arg Phe Asn Gln Tyr Lys Tyr Asn Gln Asn Phe Ser
1               5                   10                  15

Ala Gly Asn Asn
            20

<210> SEQ ID NO 206
<211> LENGTH: 20
<212> TYPE: PRT
<213> ORGANISM: Artificial Sequence
<220> FEATURE:
<223> OTHER INFORMATION: Synthetic peptide

<400> SEQUENCE: 206

Ser Ala Gly Asn Asn Glu Asn Ile Met Glu Ala His Val Gly Ile Asn
1               5                   10                  15

Gly Glu Ala Asn
            20

<210> SEQ ID NO 207
<211> LENGTH: 20
<212> TYPE: PRT
<213> ORGANISM: Artificial Sequence
<220> FEATURE:
<223> OTHER INFORMATION: Synthetic peptide

<400> SEQUENCE: 207

Asn Gly Glu Ala Asn Leu Asp Phe Leu Asn Ile Pro Leu Thr Ile Pro
1               5                   10                  15

Glu Met Arg Leu
            20

<210> SEQ ID NO 208
<211> LENGTH: 20
<212> TYPE: PRT
<213> ORGANISM: Artificial Sequence
<220> FEATURE:
<223> OTHER INFORMATION: Synthetic peptide

<400> SEQUENCE: 208

Pro Glu Met Arg Leu Pro Tyr Thr Ile Ile Thr Thr Pro Pro Leu Lys
1               5                   10                  15

Asp Phe Ser Leu
            20

<210> SEQ ID NO 209
<211> LENGTH: 20
<212> TYPE: PRT
<213> ORGANISM: Artificial Sequence
<220> FEATURE:
<223> OTHER INFORMATION: Synthetic peptide

<400> SEQUENCE: 209

Lys Asp Phe Ser Leu Trp Glu Lys Thr Gly Leu Lys Glu Phe Leu Lys
1               5                   10                  15
```

```
Thr Thr Lys Gln
            20

<210> SEQ ID NO 210
<211> LENGTH: 20
<212> TYPE: PRT
<213> ORGANISM: Artificial Sequence
<220> FEATURE:
<223> OTHER INFORMATION: Synthetic peptide

<400> SEQUENCE: 210

Lys Thr Thr Lys Gln Ser Phe Asp Leu Ser Val Lys Ala Gln Tyr Lys
1               5                   10                  15

Lys Asn Lys His
            20

<210> SEQ ID NO 211
<211> LENGTH: 20
<212> TYPE: PRT
<213> ORGANISM: Artificial Sequence
<220> FEATURE:
<223> OTHER INFORMATION: Synthetic peptide

<400> SEQUENCE: 211

Lys Lys Asn Lys His Arg His Ser Ile Thr Asn Pro Leu Ala Val Leu
1               5                   10                  15

Cys Glu Phe Ile
            20

<210> SEQ ID NO 212
<211> LENGTH: 20
<212> TYPE: PRT
<213> ORGANISM: Artificial Sequence
<220> FEATURE:
<223> OTHER INFORMATION: Synthetic peptide

<400> SEQUENCE: 212

Leu Cys Glu Phe Ile Ser Gln Ser Ile Lys Ser Phe Asp Arg His Phe
1               5                   10                  15

Glu Lys Asn Arg
            20

<210> SEQ ID NO 213
<211> LENGTH: 20
<212> TYPE: PRT
<213> ORGANISM: Artificial Sequence
<220> FEATURE:
<223> OTHER INFORMATION: Synthetic peptide

<400> SEQUENCE: 213

Phe Glu Lys Asn Arg Asn Asn Ala Leu Asp Phe Val Thr Lys Ser Tyr
1               5                   10                  15

Asn Glu Thr Lys
            20

<210> SEQ ID NO 214
<211> LENGTH: 20
<212> TYPE: PRT
<213> ORGANISM: Artificial Sequence
<220> FEATURE:
<223> OTHER INFORMATION: Synthetic peptide

<400> SEQUENCE: 214

Tyr Asn Glu Thr Lys Ile Lys Phe Asp Lys Tyr Lys Ala Glu Lys Ser
1               5                   10                  15
```

His Asp Glu Leu
            20

<210> SEQ ID NO 215
<211> LENGTH: 20
<212> TYPE: PRT
<213> ORGANISM: Artificial Sequence
<220> FEATURE:
<223> OTHER INFORMATION: Synthetic peptide

<400> SEQUENCE: 215

Ser His Asp Glu Leu Pro Arg Thr Phe Gln Ile Pro Gly Tyr Thr Val
1               5                   10                  15

Pro Val Val Asn
            20

<210> SEQ ID NO 216
<211> LENGTH: 20
<212> TYPE: PRT
<213> ORGANISM: Artificial Sequence
<220> FEATURE:
<223> OTHER INFORMATION: Synthetic peptide

<400> SEQUENCE: 216

Val Pro Val Val Asn Val Glu Val Ser Pro Phe Thr Ile Glu Met Ser
1               5                   10                  15

Ala Phe Gly Tyr
            20

<210> SEQ ID NO 217
<211> LENGTH: 20
<212> TYPE: PRT
<213> ORGANISM: Artificial Sequence
<220> FEATURE:
<223> OTHER INFORMATION: Synthetic peptide

<400> SEQUENCE: 217

Ser Ala Phe Gly Tyr Val Phe Pro Lys Ala Val Ser Met Pro Ser Phe
1               5                   10                  15

Ser Ile Leu Gly
            20

<210> SEQ ID NO 218
<211> LENGTH: 20
<212> TYPE: PRT
<213> ORGANISM: Artificial Sequence
<220> FEATURE:
<223> OTHER INFORMATION: Synthetic peptide

<400> SEQUENCE: 218

Phe Ser Ile Leu Gly Ser Asp Val Arg Val Pro Ser Tyr Thr Leu Ile
1               5                   10                  15

Leu Pro Ser Leu
            20

<210> SEQ ID NO 219
<211> LENGTH: 20
<212> TYPE: PRT
<213> ORGANISM: Artificial Sequence
<220> FEATURE:
<223> OTHER INFORMATION: Synthetic peptide

<400> SEQUENCE: 219

Ile Leu Pro Ser Leu Glu Leu Pro Val Leu His Val Pro Arg Asn Leu
1               5                   10                  15

Lys Leu Ser Leu
            20

<210> SEQ ID NO 220
<211> LENGTH: 20
<212> TYPE: PRT
<213> ORGANISM: Artificial Sequence
<220> FEATURE:
<223> OTHER INFORMATION: Synthetic peptide

<400> SEQUENCE: 220

Leu Lys Leu Ser Leu Pro His Phe Lys Glu Leu Cys Thr Ile Ser His
1               5                   10                  15

Ile Phe Ile Pro
            20

<210> SEQ ID NO 221
<211> LENGTH: 20
<212> TYPE: PRT
<213> ORGANISM: Artificial Sequence
<220> FEATURE:
<223> OTHER INFORMATION: Synthetic peptide

<400> SEQUENCE: 221

His Ile Phe Ile Pro Ala Met Gly Asn Ile Thr Tyr Asp Phe Ser Phe
1               5                   10                  15

Lys Ser Ser Val
            20

<210> SEQ ID NO 222
<211> LENGTH: 20
<212> TYPE: PRT
<213> ORGANISM: Artificial Sequence
<220> FEATURE:
<223> OTHER INFORMATION: Synthetic peptide

<400> SEQUENCE: 222

Phe Lys Ser Ser Val Ile Thr Leu Asn Thr Asn Ala Glu Leu Phe Asn
1               5                   10                  15

Gln Ser Asp Ile
            20

<210> SEQ ID NO 223
<211> LENGTH: 20
<212> TYPE: PRT
<213> ORGANISM: Artificial Sequence
<220> FEATURE:
<223> OTHER INFORMATION: Synthetic peptide

<400> SEQUENCE: 223

Asn Gln Ser Asp Ile Val Ala His Leu Leu Ser Ser Ser Ser Ser Val
1               5                   10                  15

Ile Asp Ala Leu
            20

<210> SEQ ID NO 224
<211> LENGTH: 20
<212> TYPE: PRT
<213> ORGANISM: Artificial Sequence
<220> FEATURE:
<223> OTHER INFORMATION: Synthetic peptide

<400> SEQUENCE: 224

Val Ile Asp Ala Leu Gln Tyr Lys Leu Glu Gly Thr Thr Arg Leu Thr
1               5                   10                  15

```
Arg Lys Arg Gly
        20

<210> SEQ ID NO 225
<211> LENGTH: 20
<212> TYPE: PRT
<213> ORGANISM: Artificial Sequence
<220> FEATURE:
<223> OTHER INFORMATION: Synthetic peptide

<400> SEQUENCE: 225

Thr Arg Lys Arg Gly Leu Lys Leu Ala Thr Ala Leu Ser Leu Ser Asn
1               5                   10                  15

Lys Phe Val Glu
        20

<210> SEQ ID NO 226
<211> LENGTH: 20
<212> TYPE: PRT
<213> ORGANISM: Artificial Sequence
<220> FEATURE:
<223> OTHER INFORMATION: Synthetic peptide

<400> SEQUENCE: 226

Asn Lys Phe Val Glu Gly Ser His Asn Ser Thr Val Ser Leu Thr Thr
1               5                   10                  15

Lys Asn Met Glu
        20

<210> SEQ ID NO 227
<211> LENGTH: 20
<212> TYPE: PRT
<213> ORGANISM: Artificial Sequence
<220> FEATURE:
<223> OTHER INFORMATION: Synthetic peptide

<400> SEQUENCE: 227

Thr Lys Asn Met Glu Val Ser Val Ala Lys Thr Thr Lys Ala Glu Ile
1               5                   10                  15

Pro Ile Leu Arg
        20

<210> SEQ ID NO 228
<211> LENGTH: 20
<212> TYPE: PRT
<213> ORGANISM: Artificial Sequence
<220> FEATURE:
<223> OTHER INFORMATION: Synthetic peptide

<400> SEQUENCE: 228

Ile Pro Ile Leu Arg Met Asn Phe Lys Gln Glu Leu Asn Gly Asn Thr
1               5                   10                  15

Lys Ser Lys Pro
        20

<210> SEQ ID NO 229
<211> LENGTH: 20
<212> TYPE: PRT
<213> ORGANISM: Artificial Sequence
<220> FEATURE:
<223> OTHER INFORMATION: Synthetic peptide

<400> SEQUENCE: 229

Thr Lys Ser Lys Pro Thr Val Ser Ser Ser Met Glu Phe Lys Tyr Asp
1               5                   10                  15
```

Phe Asn Ser Ser
            20

<210> SEQ ID NO 230
<211> LENGTH: 20
<212> TYPE: PRT
<213> ORGANISM: Artificial Sequence
<220> FEATURE:
<223> OTHER INFORMATION: Synthetic peptide

<400> SEQUENCE: 230

Asp Phe Asn Ser Ser Met Leu Tyr Ser Thr Ala Lys Gly Ala Val Asp
1               5                   10                  15

His Lys Leu Ser
            20

<210> SEQ ID NO 231
<211> LENGTH: 20
<212> TYPE: PRT
<213> ORGANISM: Artificial Sequence
<220> FEATURE:
<223> OTHER INFORMATION: Synthetic peptide

<400> SEQUENCE: 231

Asp His Lys Leu Ser Leu Glu Ser Leu Thr Ser Tyr Phe Ser Ile Glu
1               5                   10                  15

Ser Ser Thr Lys
            20

<210> SEQ ID NO 232
<211> LENGTH: 20
<212> TYPE: PRT
<213> ORGANISM: Artificial Sequence
<220> FEATURE:
<223> OTHER INFORMATION: Synthetic peptide

<400> SEQUENCE: 232

Glu Ser Ser Thr Lys Gly Asp Val Lys Gly Ser Val Leu Ser Arg Glu
1               5                   10                  15

Tyr Ser Gly Thr
            20

<210> SEQ ID NO 233
<211> LENGTH: 20
<212> TYPE: PRT
<213> ORGANISM: Artificial Sequence
<220> FEATURE:
<223> OTHER INFORMATION: Synthetic peptide

<400> SEQUENCE: 233

Glu Tyr Ser Gly Thr Ile Ala Ser Glu Ala Asn Thr Tyr Leu Asn Ser
1               5                   10                  15

Lys Ser Thr Arg
            20

<210> SEQ ID NO 234
<211> LENGTH: 20
<212> TYPE: PRT
<213> ORGANISM: Artificial Sequence
<220> FEATURE:
<223> OTHER INFORMATION: Synthetic peptide

<400> SEQUENCE: 234

Ser Lys Ser Thr Arg Ser Ser Val Lys Leu Gln Gly Thr Ser Lys Ile
1               5                   10                  15

Asp Asp Ile Trp
        20

<210> SEQ ID NO 235
<211> LENGTH: 20
<212> TYPE: PRT
<213> ORGANISM: Artificial Sequence
<220> FEATURE:
<223> OTHER INFORMATION: Synthetic peptide

<400> SEQUENCE: 235

Ile Asp Asp Ile Trp Asn Leu Glu Val Lys Glu Asn Phe Ala Gly Glu
1               5                   10                  15

Ala Thr Leu Gln
        20

<210> SEQ ID NO 236
<211> LENGTH: 20
<212> TYPE: PRT
<213> ORGANISM: Artificial Sequence
<220> FEATURE:
<223> OTHER INFORMATION: Synthetic peptide

<400> SEQUENCE: 236

Glu Ala Thr Leu Gln Arg Ile Tyr Ser Leu Trp Glu His Ser Thr Lys
1               5                   10                  15

Asn His Leu Gln
        20

<210> SEQ ID NO 237
<211> LENGTH: 20
<212> TYPE: PRT
<213> ORGANISM: Artificial Sequence
<220> FEATURE:
<223> OTHER INFORMATION: Synthetic peptide

<400> SEQUENCE: 237

Lys Asn His Leu Gln Leu Glu Gly Leu Phe Phe Thr Asn Gly Glu His
1               5                   10                  15

Thr Ser Lys Ala
        20

<210> SEQ ID NO 238
<211> LENGTH: 20
<212> TYPE: PRT
<213> ORGANISM: Artificial Sequence
<220> FEATURE:
<223> OTHER INFORMATION: Synthetic peptide

<400> SEQUENCE: 238

His Thr Ser Lys Ala Thr Leu Glu Leu Ser Pro Trp Gln Met Ser Ala
1               5                   10                  15

Leu Val Gln Val
        20

<210> SEQ ID NO 239
<211> LENGTH: 20
<212> TYPE: PRT
<213> ORGANISM: Artificial Sequence
<220> FEATURE:
<223> OTHER INFORMATION: Synthetic peptide

<400> SEQUENCE: 239

Ala Leu Val Gln Val His Ala Ser Gln Pro Ser Ser Phe His Asp Phe
1               5                   10                  15

```
Pro Asp Leu Gly
            20

<210> SEQ ID NO 240
<211> LENGTH: 20
<212> TYPE: PRT
<213> ORGANISM: Artificial Sequence
<220> FEATURE:
<223> OTHER INFORMATION: Synthetic peptide

<400> SEQUENCE: 240

Phe Pro Asp Leu Gly Gln Glu Val Ala Leu Asn Ala Asn Thr Lys Asn
1               5                   10                  15

Gln Lys Ile Arg
            20

<210> SEQ ID NO 241
<211> LENGTH: 20
<212> TYPE: PRT
<213> ORGANISM: Artificial Sequence
<220> FEATURE:
<223> OTHER INFORMATION: Synthetic peptide

<400> SEQUENCE: 241

Asn Gln Lys Ile Arg Trp Lys Asn Glu Val Arg Ile His Ser Gly Ser
1               5                   10                  15

Phe Gln Ser Gln
            20

<210> SEQ ID NO 242
<211> LENGTH: 20
<212> TYPE: PRT
<213> ORGANISM: Artificial Sequence
<220> FEATURE:
<223> OTHER INFORMATION: Synthetic peptide

<400> SEQUENCE: 242

Ser Phe Gln Ser Gln Val Glu Leu Ser Asn Asp Gln Glu Lys Ala His
1               5                   10                  15

Leu Asp Ile Ala
            20

<210> SEQ ID NO 243
<211> LENGTH: 20
<212> TYPE: PRT
<213> ORGANISM: Artificial Sequence
<220> FEATURE:
<223> OTHER INFORMATION: Synthetic peptide

<400> SEQUENCE: 243

His Leu Asp Ile Ala Gly Ser Leu Glu Gly His Leu Arg Phe Leu Lys
1               5                   10                  15

Asn Ile Ile Leu
            20

<210> SEQ ID NO 244
<211> LENGTH: 20
<212> TYPE: PRT
<213> ORGANISM: Artificial Sequence
<220> FEATURE:
<223> OTHER INFORMATION: Synthetic peptide

<400> SEQUENCE: 244

Lys Asn Ile Ile Leu Pro Val Tyr Asp Lys Ser Leu Trp Asp Phe Leu
1               5                   10                  15
```

```
Lys Leu Asp Val
            20

<210> SEQ ID NO 245
<211> LENGTH: 20
<212> TYPE: PRT
<213> ORGANISM: Artificial Sequence
<220> FEATURE:
<223> OTHER INFORMATION: Synthetic peptide

<400> SEQUENCE: 245

Leu Lys Leu Asp Val Thr Thr Ser Ile Gly Arg Arg Gln His Leu Arg
1               5                   10                  15

Val Ser Thr Ala
            20

<210> SEQ ID NO 246
<211> LENGTH: 20
<212> TYPE: PRT
<213> ORGANISM: Artificial Sequence
<220> FEATURE:
<223> OTHER INFORMATION: Synthetic peptide

<400> SEQUENCE: 246

Arg Val Ser Thr Ala Phe Val Tyr Thr Lys Asn Pro Asn Gly Tyr Ser
1               5                   10                  15

Phe Ser Ile Pro
            20

<210> SEQ ID NO 247
<211> LENGTH: 20
<212> TYPE: PRT
<213> ORGANISM: Artificial Sequence
<220> FEATURE:
<223> OTHER INFORMATION: Synthetic peptide

<400> SEQUENCE: 247

Ser Phe Ser Ile Pro Val Lys Val Leu Ala Asp Lys Phe Ile Thr Pro
1               5                   10                  15

Gly Leu Lys Leu
            20

<210> SEQ ID NO 248
<211> LENGTH: 20
<212> TYPE: PRT
<213> ORGANISM: Artificial Sequence
<220> FEATURE:
<223> OTHER INFORMATION: Synthetic peptide

<400> SEQUENCE: 248

Pro Gly Leu Lys Leu Asn Asp Leu Asn Ser Val Leu Val Met Pro Thr
1               5                   10                  15

Phe His Val Pro
            20

<210> SEQ ID NO 249
<211> LENGTH: 20
<212> TYPE: PRT
<213> ORGANISM: Artificial Sequence
<220> FEATURE:
<223> OTHER INFORMATION: Synthetic peptide

<400> SEQUENCE: 249

Thr Phe His Val Pro Phe Thr Asp Leu Gln Val Pro Ser Cys Lys Leu
1               5                   10                  15
```

```
Asp Phe Arg Glu
            20

<210> SEQ ID NO 250
<211> LENGTH: 20
<212> TYPE: PRT
<213> ORGANISM: Artificial Sequence
<220> FEATURE:
<223> OTHER INFORMATION: Synthetic peptide

<400> SEQUENCE: 250

Leu Asp Phe Arg Glu Ile Gln Ile Tyr Lys Lys Leu Arg Thr Ser Ser
1               5                   10                  15

Phe Ala Leu Asn
            20

<210> SEQ ID NO 251
<211> LENGTH: 20
<212> TYPE: PRT
<213> ORGANISM: Artificial Sequence
<220> FEATURE:
<223> OTHER INFORMATION: Synthetic peptide

<400> SEQUENCE: 251

Ser Phe Ala Leu Asn Leu Pro Thr Leu Pro Glu Val Lys Phe Pro Glu
1               5                   10                  15

Val Asp Val Leu
            20

<210> SEQ ID NO 252
<211> LENGTH: 20
<212> TYPE: PRT
<213> ORGANISM: Artificial Sequence
<220> FEATURE:
<223> OTHER INFORMATION: Synthetic peptide

<400> SEQUENCE: 252

Glu Val Asp Val Leu Thr Lys Tyr Ser Gln Pro Glu Asp Ser Leu Ile
1               5                   10                  15

Pro Phe Phe Glu
            20

<210> SEQ ID NO 253
<211> LENGTH: 20
<212> TYPE: PRT
<213> ORGANISM: Artificial Sequence
<220> FEATURE:
<223> OTHER INFORMATION: Synthetic peptide

<400> SEQUENCE: 253

Ile Pro Phe Phe Glu Ile Thr Val Pro Glu Ser Gln Leu Thr Val Ser
1               5                   10                  15

Gln Phe Thr Leu
            20

<210> SEQ ID NO 254
<211> LENGTH: 20
<212> TYPE: PRT
<213> ORGANISM: Artificial Sequence
<220> FEATURE:
<223> OTHER INFORMATION: Synthetic peptide

<400> SEQUENCE: 254

Ser Gln Phe Thr Leu Pro Lys Ser Val Ser Asp Gly Ile Ala Ala Leu
1               5                   10                  15
```

Asp Leu Asn Ala
        20

<210> SEQ ID NO 255
<211> LENGTH: 20
<212> TYPE: PRT
<213> ORGANISM: Artificial Sequence
<220> FEATURE:
<223> OTHER INFORMATION: Synthetic peptide

<400> SEQUENCE: 255

Leu Asp Leu Asn Ala Val Ala Asn Lys Ile Ala Asp Phe Glu Leu Pro
1               5                   10                  15

Thr Ile Ile Val
        20

<210> SEQ ID NO 256
<211> LENGTH: 20
<212> TYPE: PRT
<213> ORGANISM: Artificial Sequence
<220> FEATURE:
<223> OTHER INFORMATION: Synthetic peptide

<400> SEQUENCE: 256

Pro Thr Ile Ile Val Pro Glu Gln Thr Ile Glu Ile Pro Ser Ile Lys
1               5                   10                  15

Phe Ser Val Pro
        20

<210> SEQ ID NO 257
<211> LENGTH: 20
<212> TYPE: PRT
<213> ORGANISM: Artificial Sequence
<220> FEATURE:
<223> OTHER INFORMATION: Synthetic peptide

<400> SEQUENCE: 257

Lys Phe Ser Val Pro Ala Gly Ile Val Ile Pro Ser Phe Gln Ala Leu
1               5                   10                  15

Thr Ala Arg Phe
        20

<210> SEQ ID NO 258
<211> LENGTH: 20
<212> TYPE: PRT
<213> ORGANISM: Artificial Sequence
<220> FEATURE:
<223> OTHER INFORMATION: Synthetic peptide

<400> SEQUENCE: 258

Leu Thr Ala Arg Phe Glu Val Asp Ser Pro Val Tyr Asn Ala Thr Trp
1               5                   10                  15

Ser Ala Ser Leu
        20

<210> SEQ ID NO 259
<211> LENGTH: 20
<212> TYPE: PRT
<213> ORGANISM: Artificial Sequence
<220> FEATURE:
<223> OTHER INFORMATION: Synthetic peptide

<400> SEQUENCE: 259

Trp Ser Ala Ser Leu Lys Asn Lys Ala Asp Tyr Val Glu Thr Val Leu
1               5                   10                  15

```
Asp Ser Thr Cys
            20

<210> SEQ ID NO 260
<211> LENGTH: 20
<212> TYPE: PRT
<213> ORGANISM: Artificial Sequence
<220> FEATURE:
<223> OTHER INFORMATION: Synthetic peptide

<400> SEQUENCE: 260

Leu Asp Ser Thr Cys Ser Ser Thr Val Gln Phe Leu Glu Tyr Glu Leu
1               5                   10                  15

Asn Val Leu Gly
            20

<210> SEQ ID NO 261
<211> LENGTH: 20
<212> TYPE: PRT
<213> ORGANISM: Artificial Sequence
<220> FEATURE:
<223> OTHER INFORMATION: Synthetic peptide

<400> SEQUENCE: 261

Leu Asn Val Leu Gly Thr His Lys Ile Glu Asp Gly Thr Leu Ala Ser
1               5                   10                  15

Lys Thr Lys Gly
            20

<210> SEQ ID NO 262
<211> LENGTH: 20
<212> TYPE: PRT
<213> ORGANISM: Artificial Sequence
<220> FEATURE:
<223> OTHER INFORMATION: Synthetic peptide

<400> SEQUENCE: 262

Ser Lys Thr Lys Gly Thr Leu Ala His Arg Asp Phe Ser Ala Glu Tyr
1               5                   10                  15

Glu Glu Asp Gly
            20

<210> SEQ ID NO 263
<211> LENGTH: 20
<212> TYPE: PRT
<213> ORGANISM: Artificial Sequence
<220> FEATURE:
<223> OTHER INFORMATION: Synthetic peptide

<400> SEQUENCE: 263

Tyr Glu Glu Asp Gly Lys Phe Glu Gly Leu Gln Glu Trp Glu Gly Lys
1               5                   10                  15

Ala His Leu Asn
            20

<210> SEQ ID NO 264
<211> LENGTH: 20
<212> TYPE: PRT
<213> ORGANISM: Artificial Sequence
<220> FEATURE:
<223> OTHER INFORMATION: Synthetic peptide

<400> SEQUENCE: 264

Lys Ala His Leu Asn Ile Lys Ser Pro Ala Phe Thr Asp Leu His Leu
1               5                   10                  15
```

Arg Tyr Gln Lys
        20

<210> SEQ ID NO 265
<211> LENGTH: 20
<212> TYPE: PRT
<213> ORGANISM: Artificial Sequence
<220> FEATURE:
<223> OTHER INFORMATION: Synthetic peptide

<400> SEQUENCE: 265

Leu Arg Tyr Gln Lys Asp Lys Gly Ile Ser Thr Ser Ala Ala Ser
1               5                   10                  15

Pro Ala Val Gly
        20

<210> SEQ ID NO 266
<211> LENGTH: 20
<212> TYPE: PRT
<213> ORGANISM: Artificial Sequence
<220> FEATURE:
<223> OTHER INFORMATION: Synthetic peptide

<400> SEQUENCE: 266

Ser Pro Ala Val Gly Thr Val Gly Met Asp Met Asp Glu Asp Asp
1               5                   10                  15

Phe Ser Lys Trp
        20

<210> SEQ ID NO 267
<211> LENGTH: 20
<212> TYPE: PRT
<213> ORGANISM: Artificial Sequence
<220> FEATURE:
<223> OTHER INFORMATION: Synthetic peptide

<400> SEQUENCE: 267

Asp Phe Ser Lys Trp Asn Phe Tyr Tyr Ser Pro Gln Ser Ser Pro Asp
1               5                   10                  15

Lys Lys Leu Thr
        20

<210> SEQ ID NO 268
<211> LENGTH: 20
<212> TYPE: PRT
<213> ORGANISM: Artificial Sequence
<220> FEATURE:
<223> OTHER INFORMATION: Synthetic peptide

<400> SEQUENCE: 268

Asp Lys Lys Leu Thr Ile Phe Lys Thr Glu Leu Arg Val Arg Glu Ser
1               5                   10                  15

Asp Glu Glu Thr
        20

<210> SEQ ID NO 269
<211> LENGTH: 20
<212> TYPE: PRT
<213> ORGANISM: Artificial Sequence
<220> FEATURE:
<223> OTHER INFORMATION: Synthetic peptide

<400> SEQUENCE: 269

Ser Asp Glu Glu Thr Gln Ile Lys Val Asn Trp Glu Glu Glu Ala Ala
1               5                   10                  15

```
Ser Gly Leu Leu
            20

<210> SEQ ID NO 270
<211> LENGTH: 20
<212> TYPE: PRT
<213> ORGANISM: Artificial Sequence
<220> FEATURE:
<223> OTHER INFORMATION: Synthetic peptide

<400> SEQUENCE: 270

Ala Ser Gly Leu Leu Thr Ser Leu Lys Asp Asn Val Pro Lys Ala Thr
1               5                   10                  15

Gly Val Leu Tyr
            20

<210> SEQ ID NO 271
<211> LENGTH: 20
<212> TYPE: PRT
<213> ORGANISM: Artificial Sequence
<220> FEATURE:
<223> OTHER INFORMATION: Synthetic peptide

<400> SEQUENCE: 271

Thr Gly Val Leu Tyr Asp Tyr Val Asn Lys Tyr His Trp Glu His Thr
1               5                   10                  15

Gly Leu Thr Leu
            20

<210> SEQ ID NO 272
<211> LENGTH: 20
<212> TYPE: PRT
<213> ORGANISM: Artificial Sequence
<220> FEATURE:
<223> OTHER INFORMATION: Synthetic peptide

<400> SEQUENCE: 272

Thr Gly Leu Thr Leu Arg Glu Val Ser Ser Lys Leu Arg Arg Asn Leu
1               5                   10                  15

Gln Asn Asn Ala
            20

<210> SEQ ID NO 273
<211> LENGTH: 20
<212> TYPE: PRT
<213> ORGANISM: Artificial Sequence
<220> FEATURE:
<223> OTHER INFORMATION: Synthetic peptide

<400> SEQUENCE: 273

Leu Gln Asn Asn Ala Glu Trp Val Tyr Gln Gly Ala Ile Arg Gln Ile
1               5                   10                  15

Asp Asp Ile Asp
            20

<210> SEQ ID NO 274
<211> LENGTH: 20
<212> TYPE: PRT
<213> ORGANISM: Artificial Sequence
<220> FEATURE:
<223> OTHER INFORMATION: Synthetic peptide

<400> SEQUENCE: 274

Ile Asp Asp Ile Asp Val Arg Phe Gln Lys Ala Ala Ser Gly Thr Thr
1               5                   10                  15
```

Gly Thr Tyr Gln
            20

<210> SEQ ID NO 275
<211> LENGTH: 20
<212> TYPE: PRT
<213> ORGANISM: Artificial Sequence
<220> FEATURE:
<223> OTHER INFORMATION: Synthetic peptide

<400> SEQUENCE: 275

Thr Gly Thr Tyr Gln Glu Trp Lys Asp Lys Ala Gln Asn Leu Tyr Gln
1               5                   10                  15

Glu Leu Leu Thr
            20

<210> SEQ ID NO 276
<211> LENGTH: 20
<212> TYPE: PRT
<213> ORGANISM: Artificial Sequence
<220> FEATURE:
<223> OTHER INFORMATION: Synthetic peptide

<400> SEQUENCE: 276

Gln Glu Leu Leu Thr Gln Glu Gly Gln Ala Ser Phe Gln Gly Leu Lys
1               5                   10                  15

Asp Asn Val Phe
            20

<210> SEQ ID NO 277
<211> LENGTH: 20
<212> TYPE: PRT
<213> ORGANISM: Artificial Sequence
<220> FEATURE:
<223> OTHER INFORMATION: Synthetic peptide

<400> SEQUENCE: 277

Lys Asp Asn Val Phe Asp Gly Leu Val Arg Val Thr Gln Lys Phe His
1               5                   10                  15

Met Lys Val Lys
            20

<210> SEQ ID NO 278
<211> LENGTH: 20
<212> TYPE: PRT
<213> ORGANISM: Artificial Sequence
<220> FEATURE:
<223> OTHER INFORMATION: Synthetic peptide

<400> SEQUENCE: 278

His Met Lys Val Lys His Leu Ile Asp Ser Leu Ile Asp Phe Leu Asn
1               5                   10                  15

Phe Pro Arg Phe
            20

<210> SEQ ID NO 279
<211> LENGTH: 20
<212> TYPE: PRT
<213> ORGANISM: Artificial Sequence
<220> FEATURE:
<223> OTHER INFORMATION: Synthetic peptide

<400> SEQUENCE: 279

Asn Phe Pro Arg Phe Gln Phe Pro Gly Lys Pro Gly Ile Tyr Thr Arg
1               5                   10                  15

```
Glu Glu Leu Cys
            20

<210> SEQ ID NO 280
<211> LENGTH: 20
<212> TYPE: PRT
<213> ORGANISM: Artificial Sequence
<220> FEATURE:
<223> OTHER INFORMATION: Synthetic peptide

<400> SEQUENCE: 280

Arg Glu Glu Leu Cys Thr Met Phe Ile Arg Glu Val Gly Thr Val Leu
1               5                   10                  15

Ser Gln Val Tyr
            20

<210> SEQ ID NO 281
<211> LENGTH: 20
<212> TYPE: PRT
<213> ORGANISM: Artificial Sequence
<220> FEATURE:
<223> OTHER INFORMATION: Synthetic peptide

<400> SEQUENCE: 281

Leu Ser Gln Val Tyr Ser Lys Val His Asn Gly Ser Glu Ile Leu Phe
1               5                   10                  15

Ser Tyr Phe Gln
            20

<210> SEQ ID NO 282
<211> LENGTH: 20
<212> TYPE: PRT
<213> ORGANISM: Artificial Sequence
<220> FEATURE:
<223> OTHER INFORMATION: Synthetic peptide

<400> SEQUENCE: 282

Phe Ser Tyr Phe Gln Asp Leu Val Ile Thr Leu Pro Phe Glu Leu Arg
1               5                   10                  15

Lys His Lys Leu
            20

<210> SEQ ID NO 283
<211> LENGTH: 20
<212> TYPE: PRT
<213> ORGANISM: Artificial Sequence
<220> FEATURE:
<223> OTHER INFORMATION: Synthetic peptide

<400> SEQUENCE: 283

Arg Lys His Lys Leu Ile Asp Val Ile Ser Met Tyr Arg Glu Leu Leu
1               5                   10                  15

Lys Asp Leu Ser
            20

<210> SEQ ID NO 284
<211> LENGTH: 20
<212> TYPE: PRT
<213> ORGANISM: Artificial Sequence
<220> FEATURE:
<223> OTHER INFORMATION: Synthetic peptide

<400> SEQUENCE: 284

Leu Lys Asp Leu Ser Lys Glu Ala Gln Glu Val Phe Lys Ala Ile Gln
1               5                   10                  15
```

```
Ser Leu Lys Thr
            20

<210> SEQ ID NO 285
<211> LENGTH: 20
<212> TYPE: PRT
<213> ORGANISM: Artificial Sequence
<220> FEATURE:
<223> OTHER INFORMATION: Synthetic peptide

<400> SEQUENCE: 285

Gln Ser Leu Lys Thr Thr Glu Val Leu Arg Asn Leu Gln Asp Leu Leu
1               5                   10                  15

Gln Phe Ile Phe
            20

<210> SEQ ID NO 286
<211> LENGTH: 20
<212> TYPE: PRT
<213> ORGANISM: Artificial Sequence
<220> FEATURE:
<223> OTHER INFORMATION: Synthetic peptide

<400> SEQUENCE: 286

Leu Gln Phe Ile Phe Gln Leu Ile Glu Asp Asn Ile Lys Gln Leu Lys
1               5                   10                  15

Glu Met Lys Phe
            20

<210> SEQ ID NO 287
<211> LENGTH: 20
<212> TYPE: PRT
<213> ORGANISM: Artificial Sequence
<220> FEATURE:
<223> OTHER INFORMATION: Synthetic peptide

<400> SEQUENCE: 287

Lys Glu Met Lys Phe Thr Tyr Leu Ile Asn Tyr Ile Gln Asp Glu Ile
1               5                   10                  15

Asn Thr Ile Phe
            20

<210> SEQ ID NO 288
<211> LENGTH: 20
<212> TYPE: PRT
<213> ORGANISM: Artificial Sequence
<220> FEATURE:
<223> OTHER INFORMATION: Synthetic peptide

<400> SEQUENCE: 288

Ile Asn Thr Ile Phe Asn Asp Tyr Ile Pro Tyr Val Phe Lys Leu Leu
1               5                   10                  15

Lys Glu Asn Leu
            20

<210> SEQ ID NO 289
<211> LENGTH: 20
<212> TYPE: PRT
<213> ORGANISM: Artificial Sequence
<220> FEATURE:
<223> OTHER INFORMATION: Synthetic peptide

<400> SEQUENCE: 289

Leu Lys Glu Asn Leu Cys Leu Asn Leu His Lys Phe Asn Glu Phe Ile
1               5                   10                  15
```

Gln Asn Glu Leu
        20

<210> SEQ ID NO 290
<211> LENGTH: 20
<212> TYPE: PRT
<213> ORGANISM: Artificial Sequence
<220> FEATURE:
<223> OTHER INFORMATION: Synthetic peptide

<400> SEQUENCE: 290

Ile Gln Asn Glu Leu Gln Glu Ala Ser Gln Glu Leu Gln Gln Ile His
1               5                   10                  15

Gln Tyr Ile Met
        20

<210> SEQ ID NO 291
<211> LENGTH: 20
<212> TYPE: PRT
<213> ORGANISM: Artificial Sequence
<220> FEATURE:
<223> OTHER INFORMATION: Synthetic peptide

<400> SEQUENCE: 291

His Gln Tyr Ile Met Ala Leu Arg Glu Glu Tyr Phe Asp Pro Ser Ile
1               5                   10                  15

Val Gly Trp Thr
        20

<210> SEQ ID NO 292
<211> LENGTH: 20
<212> TYPE: PRT
<213> ORGANISM: Artificial Sequence
<220> FEATURE:
<223> OTHER INFORMATION: Synthetic peptide

<400> SEQUENCE: 292

Ile Val Gly Trp Thr Val Lys Tyr Tyr Glu Leu Glu Glu Lys Ile Val
1               5                   10                  15

Ser Leu Ile Lys
        20

<210> SEQ ID NO 293
<211> LENGTH: 20
<212> TYPE: PRT
<213> ORGANISM: Artificial Sequence
<220> FEATURE:
<223> OTHER INFORMATION: Synthetic peptide

<400> SEQUENCE: 293

Val Ser Leu Ile Lys Asn Leu Leu Val Ala Leu Lys Asp Phe His Ser
1               5                   10                  15

Glu Tyr Ile Val
        20

<210> SEQ ID NO 294
<211> LENGTH: 20
<212> TYPE: PRT
<213> ORGANISM: Artificial Sequence
<220> FEATURE:
<223> OTHER INFORMATION: Synthetic peptide

<400> SEQUENCE: 294

Ser Glu Tyr Ile Val Ser Ala Ser Asn Phe Thr Ser Gln Leu Ser Ser
1               5                   10                  15

```
Gln Val Glu Gln
            20

<210> SEQ ID NO 295
<211> LENGTH: 20
<212> TYPE: PRT
<213> ORGANISM: Artificial Sequence
<220> FEATURE:
<223> OTHER INFORMATION: Synthetic peptide

<400> SEQUENCE: 295

Ser Gln Val Glu Gln Phe Leu His Arg Asn Ile Gln Glu Tyr Leu Ser
1               5                   10                  15

Ile Leu Thr Asp
            20

<210> SEQ ID NO 296
<211> LENGTH: 20
<212> TYPE: PRT
<213> ORGANISM: Artificial Sequence
<220> FEATURE:
<223> OTHER INFORMATION: Synthetic peptide

<400> SEQUENCE: 296

Ser Ile Leu Thr Asp Pro Asp Gly Lys Gly Lys Glu Lys Ile Ala Glu
1               5                   10                  15

Leu Ser Ala Thr
            20

<210> SEQ ID NO 297
<211> LENGTH: 20
<212> TYPE: PRT
<213> ORGANISM: Artificial Sequence
<220> FEATURE:
<223> OTHER INFORMATION: Synthetic peptide

<400> SEQUENCE: 297

Glu Leu Ser Ala Thr Ala Gln Glu Ile Ile Lys Ser Gln Ala Ile Ala
1               5                   10                  15

Thr Lys Lys Ile
            20

<210> SEQ ID NO 298
<211> LENGTH: 20
<212> TYPE: PRT
<213> ORGANISM: Artificial Sequence
<220> FEATURE:
<223> OTHER INFORMATION: Synthetic peptide

<400> SEQUENCE: 298

Thr Lys Lys Ile Ile Ser Asp Tyr His Gln Gln Phe Arg Tyr Lys Leu
1               5                   10                  15

Gln Asp Phe Ser
            20

<210> SEQ ID NO 299
<211> LENGTH: 20
<212> TYPE: PRT
<213> ORGANISM: Artificial Sequence
<220> FEATURE:
<223> OTHER INFORMATION: Synthetic peptide

<400> SEQUENCE: 299

Leu Gln Asp Phe Ser Asp Gln Leu Ser Asp Tyr Tyr Glu Lys Phe Ile
1               5                   10                  15
```

```
Ala Glu Ser Lys
            20

<210> SEQ ID NO 300
<211> LENGTH: 20
<212> TYPE: PRT
<213> ORGANISM: Artificial Sequence
<220> FEATURE:
<223> OTHER INFORMATION: Synthetic peptide

<400> SEQUENCE: 300

Ile Ala Glu Ser Lys Arg Leu Ile Asp Leu Ser Ile Gln Asn Tyr His
1               5                   10                  15

Thr Phe Leu Ile
            20

<210> SEQ ID NO 301
<211> LENGTH: 20
<212> TYPE: PRT
<213> ORGANISM: Artificial Sequence
<220> FEATURE:
<223> OTHER INFORMATION: Synthetic peptide

<400> SEQUENCE: 301

His Thr Phe Leu Ile Tyr Ile Thr Glu Leu Leu Lys Lys Leu Gln Ser
1               5                   10                  15

Thr Thr Val Met
            20

<210> SEQ ID NO 302
<211> LENGTH: 20
<212> TYPE: PRT
<213> ORGANISM: Artificial Sequence
<220> FEATURE:
<223> OTHER INFORMATION: Synthetic peptide

<400> SEQUENCE: 302

Ser Thr Thr Val Met Asn Pro Tyr Met Lys Leu Ala Pro Gly Glu Leu
1               5                   10                  15

Thr Ile Ile Leu
            20

<210> SEQ ID NO 303
<211> LENGTH: 63
<212> TYPE: DNA
<213> ORGANISM: Artificial Sequence
<220> FEATURE:
<223> OTHER INFORMATION: Synthetic polynucleotide

<400> SEQUENCE: 303
caaaacgacc aagcaaagct tgatctgag cgtgaaagcg cagtataaga aaacaaaca      60 cta                                                                 63

<210> SEQ ID NO 304
<211> LENGTH: 71
<212> TYPE: DNA
<213> ORGANISM: Artificial Sequence
<220> FEATURE:
<223> OTHER INFORMATION: Synthetic polynucleotide

<400> SEQUENCE: 304
catggttttg ctggttcgtt tcgaaactag actcgcactt tcgcgtcata ttcttttgt    60 ttgtgattcg a                                                       71
```

```
<210> SEQ ID NO 305
<211> LENGTH: 22
<212> TYPE: PRT
<213> ORGANISM: Artificial Sequence
<220> FEATURE:
<223> OTHER INFORMATION: Synthetic peptide

<400> SEQUENCE: 305

Lys Thr Thr Lys Gln Ser Phe Asp Leu Ser Val Lys Ala Gln Tyr Lys
1               5                   10                  15

Lys Asn Ser Asp Lys His
            20
```

FUSION PROTEINS AND RELATED COMPOSITIONS, METHODS AND SYSTEMS FOR TREATMENT AND/OR PREVENTION OF ATHEROSCLEROSIS

CROSS REFERENCE TO RELATED APPLICATIONS

The present application is related and claims priority of U.S. provisional application Ser. No. 61/302,051 entitled "Fusion Proteins and Related Compositions, Methods and Systems For Treatment and/or Prevention of Atherosclerosis" filed on Feb. 5, 2010 which is incorporated herein by reference in its entirety.

TECHNICAL FIELD

The present disclosure relates to fusion proteins and related compositions, methods and systems for treatment and/or prevention of atherosclerosis.

BACKGROUND

Atherosclerosis is currently viewed as a chronic lipid-related and immune-mediated inflammatory disease of the arterial walls. Many immune components have been identified that participate in atherogenesis and pre-clinical studies have yielded promising results suggesting that immuno-modulatory therapies targeting these components can reduce atherosclerosis.

SUMMARY

Provided herein, are methods and systems for inducing immunomodulatory responses in an individual. In several embodiments, the immunomodulatory responses induced by the methods and systems of the present disclosure are associated to a therapeutic or preventive effect related to atherosclerosis in the individual or a condition associated thereto.

According a first aspect a fusion protein is described. The fusion protein comprises an antigenic fragment of apoB-100 protein or a derivative thereof and a protein carrier, the antigenic fragment and the carrier comprised in the fusion protein in a fragment:carrier 1:1 molar ratio the fusion protein capable of inducing antigen specific regulatory T cells, the antigen specific regulatory T cells specific for the antigenic fragment of apoB-100.

According to a second aspect, a method to treat and/or prevent atherosclerosis in an individual is described. The method comprises administering to the individual an effective amount of a fusion protein herein described, the effective amount eliciting an antigen specific Treg immunomodulatory response in the individual, the antigen specific Treg immunomodulatory response specific for the antigenic fragments of apoB-100 or a derivative thereof.

According to a third aspect, a composition is described. The composition comprises a fusion protein herein described and an adjuvant and/or excipient. In several embodiments the adjuvant and/or excipients are pharmaceutically acceptable and the composition is pharmaceutical composition According to a fourth aspect, a method to produce a fusion protein is described. The method comprises conjugating a fragment of apoB-100 or a derivative thereof with a suitable protein carrier to provide a fusion protein capable of inducing antigen specific regulatory T cells, the antigen specific regulatory T cells specific for the fragment of apoB-100 or the derivative thereof.

According to a fifth aspect, a method to induce an antigen specific Tregulatory cell is described. The method comprises contacting a Tregulatory cell with a fusion protein herein described for a time and under conditions to allow induction of a Tregulatory response, wherein the contacting results in an antigen-specific induction of a Tregulatory cell that is specific for the fragment of apoB-100 or derivative thereof comprised in the fusion protein.

The methods and systems herein described can be used in connection with applications wherein reduction of plaque, attenuation of plaque growth and/or a therapeutic or preventive effect for atherosclerosis in an individual is desired.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and examples sections, serve to explain the principles and implementations of the disclosure.

DETAILED DESCRIPTION

Figure 1:
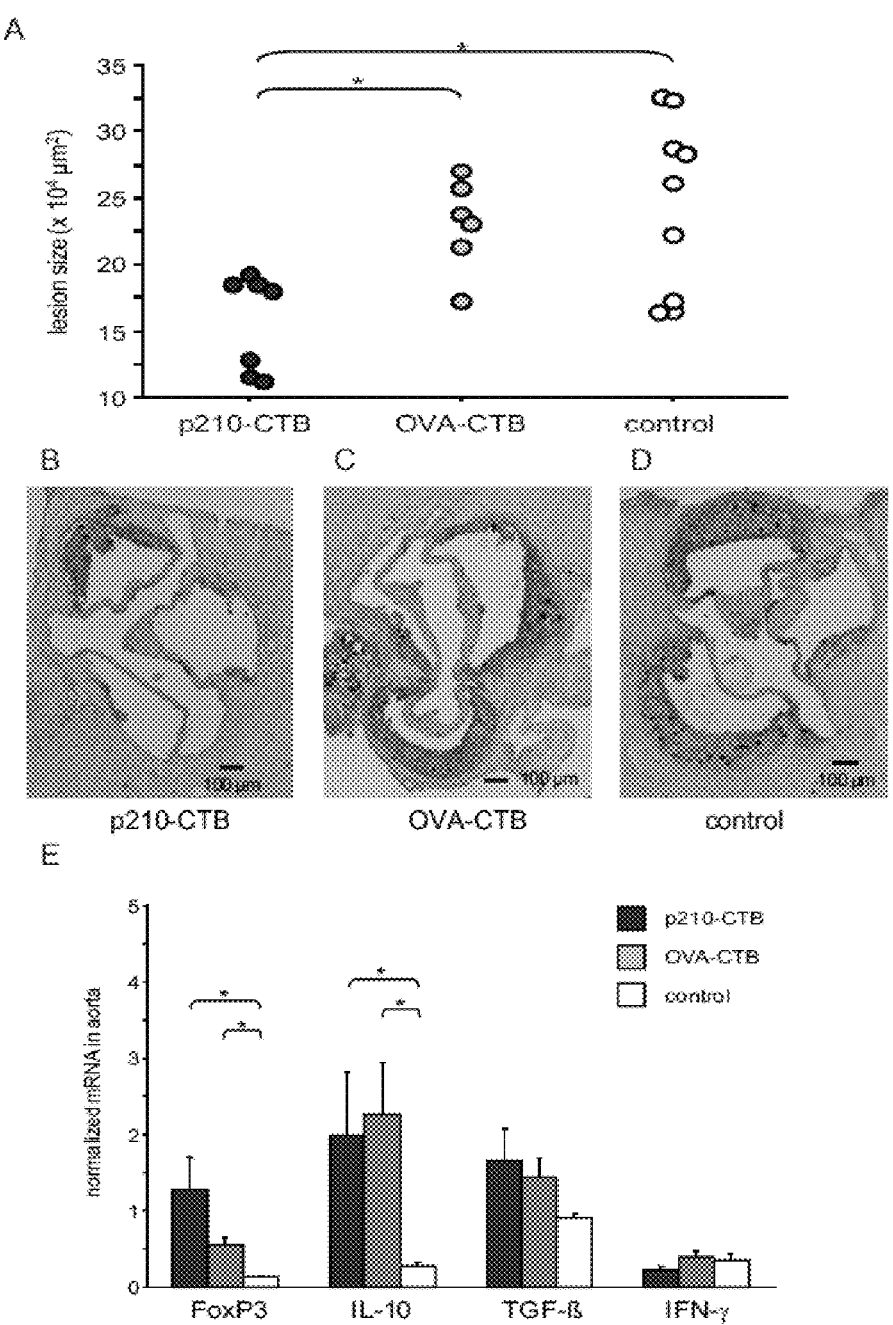
FIG. 1 shows data concerning intranasal p210-CTB administered twice weekly for 12 weeks reduced atherosclerotic lesion size in the aortic root of female apoe$^{-/-}$ mice. (A) Data from the three groups are shown: black circles represent animals from the p210-CTB group, grey circles animals from the OVA-CTB group and white circles animals from the control group, respectively. * indicates p<0.05. (B-D) Representative photomicrographs show oil red O stained aortic root sections from each group (50× magnification). (E) Nasal immunization with CTB fusion proteins increased FoxP3 and IL-10 mRNA levels in thoracic aorta from apoe$^{-/-}$ mice after 12 weeks of treatment. mRNA transcript ratios based on HPRT expression are shown for each gene of interest for all three groups. * indicates p<0.05

Provided herein are fusion proteins, compositions, methods and systems that in several embodiments are suitable to be used for immunoprotection against atherosclerosis.

The term "fusion protein" as used herein indicates a protein created through the attaching of two or more polypeptides which originated from separate proteins. In particular fusion proteins can be created by recombinant DNA technology and are typically used in biological research or therapeutics. Fusion proteins can also be created through chemical covalent conjugation with or without a linker between the polypeptides portion of the fusion proteins.

The term "attach" or "attached" as used herein, refers to connecting or uniting by a bond, link, force or tie in order to keep two or more components together, which encompasses either direct or indirect attachment such that for example where a first polypeptide is directly bound to a second polypeptide or material, and the embodiments wherein one or more intermediate compounds, and in particular polypeptides, are disposed between the first polypeptide and the second polypeptide or material.

The term "protein" or "polypeptide" as used herein indicates an organic polymer composed of two or more amino acid monomers and/or analogs thereof. The term "polypeptide" includes amino acid polymers of any length including full length proteins and peptides, as well as analogs and fragments thereof. A polypeptide of three or more amino acids is also called an oligopeptide. As used herein the term "amino acid", "amino acidic monomer", or "amino acid residue" refers to any of the twenty naturally occurring amino acids including synthetic amino acids with unnatural side chains and including both D and L optical isomers. The term "amino acid analog" refers to an amino acid in which one or more individual atoms have been replaced, either with a different atom, isotope, or with a different functional group but is otherwise identical to its natural amino acid analog.

In particular in several embodiments, fusion proteins, compositions methods and systems are described that in several embodiments are suitable for eliciting an antigen specific T regulatory cells response in an individual.

The term "antigen", as it is used herein, relates to any substance that, when introduced into the body can stimulate an immune response. Antigens comprise exogenous antigens (antigens that have entered the body from the outside, for example by inhalation, ingestion, or injection) and endogenous antigens or autoantigens (antigens that have been generated within the body). In particular, an "autoantigen" is an antigen that despite being a normal tissue constituent is the target of a humoral or cell-mediated immune response. Exemplary autoantigens comprise autoantigens associated to atherogenesis and/or atherosclerosis provided by low-density lipoprotein and its constituent protein, ApoB100.

The term "regulatory T cell" or "Treg" as used herein indicates a component of the immune system that suppress immune responses of other cells, and comprises T cells that express the CD8 transmembrane glycoprotein (CD8+ T cells); T cells that express CD4, CD25, and Foxp3 (CD4+ CD25+ regulatory T cells); and other T cell types that have suppressive function identifiable by a skilled person. Treg comprise both naturally occurring T cells and T cells generated in vitro.

The term "antigen-specific" as used indicates an immunitary response, and in particular, immunological tolerance, for a certain antigen which is characterized by a substantially less or no immune response (and in particular, immunological tolerance) for another antigen. Accordingly, an antigen specific regulatory T cell, specific for one or more autoantigens is able, under appropriate conditions to minimize to the specific immune response to the one or more autoantigens with substantially less or no minimizing effect on the immune response towards other antigens or autoantigens.

Fusion proteins comprising autoantigen associated with atherogenesis and/or atherosclerosis and related methods and systems are herein described that are capable of eliciting an autoantigen specific Treg response and that in several embodiments can be used for treating and/or preventing atherosclerosis or a condition associated thereto in an individual.

The term "atherosclerosis" as used herein indicates an inflammatory condition, and in particular the condition in which an artery wall thickens as the result of a build-up of fatty materials such as cholesterol. In some cases, atherosclerosis is treated with statin therapy (1). In several cases, atherosclerosis is a syndrome affecting arterial blood vessels, a chronic inflammatory response in the walls of arteries, in large part due to the accumulation of macrophage white blood cells and promoted by Low-density lipoproteins (plasma proteins that carry cholesterol and triglycerides) without adequate removal of fats and cholesterol from the macrophages by functional high density lipoproteins (HDL), (see apoA-1 Milano). Lipid retention and modification in the arterial intima in some cases elicit a chronic inflammatory process with autoimmune responses and the development of atherosclerotic lesions (2). Both adaptive and innate immune mechanisms have been described as contributors to this process (3-6). While pattern recognition receptors of innate immunity are believed to account for cholesterol uptake and contribute to activation of macrophages and endothelial cells, antigen-specific T cells recognizing low density lipoprotein (LDL) particles in the intima provide strong proinflammatory stimuli that accelerate atherogenesis. Atherosclerosis is commonly referred to as a hardening or furring of the arteries. It is believed to be caused by the formation of multiple plaques within the arteries. Typically, autoimmune responses to low-density lipoproteins (LDL) contribute to its progression, while immunization with LDL may induce atheroprotective or proatherogenic responses.

The term "treating" or "treatment" as used herein indicates any activity that is part of a medical care for, or that deals with, a condition medically or surgically. The term "preventing" or "prevention" as used herein indicates any activity, which reduces the burden of mortality or morbidity from a condition in an individual. This takes place at primary, secondary and tertiary prevention levels, wherein: a) primary prevention avoids the development of a disease; b) secondary prevention activities are aimed at early disease treatment, thereby increasing opportunities for interventions to prevent progression of the disease and emergence of symptoms; and c) tertiary prevention reduces the negative impact of an already established disease by restoring function and reducing disease-related complications.

The term "condition" as used herein indicates as usually the physical status of the body of an individual (as a whole or of one or more of its parts) that does not conform to a physical status of the individual (as a whole or of one or more of its parts) that is associated with a state of complete physical, mental and possibly social well-being. Conditions herein described include but are not limited to disorders and diseases wherein the term "disorder" indicates a condition of the living individual that is associated to a functional abnormality of the body or of any of its parts, and the term "disease" indicates a condition of the living individual that impairs normal functioning of the body or of any of its parts and is typically manifested by distinguishing signs and symptoms. Exemplary conditions include but are not limited to injuries, disabilities, disorders (including mental and physical disorders), syndromes, infections, deviant behaviors of the individual and atypical variations of structure and functions of the body of an individual or parts thereof.

The wording "associated to" as used herein with reference to two items indicates a relation between the two items such that the occurrence of a first item is accompanied by the occurrence of the second item, which includes but is not limited to a cause-effect relation and sign/symptoms-disease relation.

The term "individuals" as used herein indicates a single biological organism such as higher animals and in particular vertebrates such as mammals and more particularly human beings.

In several embodiments, induction of an antigen specific Tregulatory cell response is provided by a fusion protein comprising an antigenic fragment of apoB-100 and a protein carrier attached directly or through a linker in an fragment: carrier 1:1 proportion.

The term "fragment" as used herein indicates a portion of a polypeptide of any length. A skilled person will understand that the term encompasses peptides of any origin which have a sequence corresponding to the portion of the polypeptide at issue. An antigenic fragment of apoB100 is accordingly a portion of apoB-100 that presents antigenic properties. Antigenic fragments of apoB-100 herein described also include possible derivatives thereof.

The term "derivative" as used herein with reference to a first polypeptide (e.g., apoB-100 antigenic fragment), indicates a second polypeptide that is structurally related to the first polypeptide and is derivable from the first polypeptide by a modification that introduces a feature that is not present in the first polypeptide, while retaining functional properties of the first polypeptide. Accordingly, a derivative polypeptide of an antigenic fragment of apoB-100, usually differs from the original polypeptide or portion thereof by modification of the amino acidic sequence that might or might not be associated with an additional function not present in the original polypeptide or portion thereof. A derivative polypeptide of an antigenic fragment of apoB-100 retains however antigenic properties comparable to the ones described in connection with apoB-100 or the antigenic fragment thereof. Retaining of one or more antigenic properties can be verified with methods identifiable by a skilled person upon reading of the present disclosure, on the basis of the specific antigenic property of the fragment at issue. Exemplary methods comprise immunizing an animal (e.g. mouse) with a candidate derivative, determining production of antibody specific for the derivative in the animal (e.g. by ELISA such as immunometric ELISA) and comparing the determined antibody production for the candidate derivative with a corresponding antibody production of the fragment. Additional methods to determine further antigenic properties can be identified by a skilled person upon reading of the present disclosure.

The term "protein carrier" as used herein indicates proteins that transport a specific substance or group of substances through intracellular compartments or in extracellular fluids (e.g. in the blood) or else across the cell membrane. Exemplary carrier proteins comprise subunit B of cholera toxin, Avidin, BTG protein, Bovine G globulin, Bovine Immunoglobulin G, Bovine Thyroglobulin, Bovine Serum Albumin (BSA), Conalbumin, Edestein, Exoprotein A from *Pseudomonas aeruginosa*, HC (Hemocyanin from crab *Paralithodes camtschatica*), *Helix Promatia* Haemocyanin (HPH), Human Serum Albumin (HSA), KTI (Kunits trypsin inhibitor from soybeans), Keyhole Limpet Heamocyanin (KLH), LPH (Haemocyanin from *Limulus polyphemus*), Ovalbumin, Pam3Cys-Th, Polylysine, porcine Thyroglobulin (PTG), Purified Protein Derivative (PPD), Rabbit Serum Albumin (RSA), Soybean Trypsin Inhibitor (STI) Sunflower Globulin (SFG) and additional molecules identifiable by a skilled person. Additional carriers comprise molecule having immunogenic activities including cytokines such as IL-10, IL12, IL-4 IL-16 and Transforming Growth Factor Beta (TGFβ).

In some embodiments, attachment of the carrier is performed at the C-terminus or N-terminus of the fragment. In an embodiment the fusion protein can be provided as a single polypeptide through recombinant DNA technology and related processes, such as cloning, chimeric constructs, Polymerase Chain Reaction and additional procedures identifiable by a skilled person. In some embodiments, attachment can be performed through chemical linkage of the fragment to the carrier using methods also identifiable by a skilled person.

In some embodiments, the antigenic fragment of apoB-100 comprises amino acids 3136-3155 of human apoB-100 (p210) and/or additional fragments selected from the peptides illustrated in the Examples section.

In particular in some embodiments the fragment portion of the fusion product can comprise one or more of peptides P2, P11, P25, P32, P45, P74, P102, P129, P143, P148, P154, P162, P210, P219, P240. More particularly, in some embodiments the fragment portion of the fusion products can comprise one or more of peptides P2, P45, P102 and P210.

In an embodiment, wherein the fragment portion of the fusion protein comprise more than one peptide, the fragment portion can comprise up to 10 peptides in a construct that, at least in some of those embodiments, is expected to have effects analogous to those of cancer or infectious vaccines, such as the ones described in (35) herein incorporated by reference in its entirety. As skilled person will be able to identify suitable combination of peptides for a desired immunogenic, preventive and/or therapeutic effect upon reading of the present disclosure.

In some embodiments, the carrier protein can comprise at least one monomer of the subunit B of cholera toxin which can be formed by a recombinant pentameric B oligomer that is capable of binding GM-1 receptors (e.g. on the surface of intestinal epithelial cells). In particular, in some embodiments, the carrier protein can be formed by at least one of five identical monomers with a molecular weight of approximately 11.6 kDa recombinant pentameric B oligomer molecule. In some of those embodiments, the monomers are tightly linked into a trypsin-resistant pentameric ring-like structure with a molecular weight of approximately 58 kDa.

In some embodiments, the antigenic fragments can be attached to the carrier molecule using biological genetic engineering to produce a fusion protein (with single or multiple copies of the immunogenic peptide) and procedures identifiable by a skilled person upon reading of the present disclosure.

In some embodiments, the antigenic fragments can be attached to the carrier molecule using chemical covalent conjugation (with or without a linker group) and procedures identifiable by a skilled person upon reading of the present disclosure.

In some embodiments, fusion products or antigenic fragments can be used in the treatment of atherosclerosis and or for induction of regulatory T-cells In some embodiments, antigen-specific immunomodulation by vaccination is an approach used to prevent or treat chronic inflammatory diseases associated to atherogenesis. In some of those cases, by mobilizing protective immune responses in an antigen-specific manner, side effects due to hampered host defense against infections can be avoided. Exemplary protocols comprise protocols described to treat atherosclerosis in mice and rabbits immunized with LDL, beta2-glycoprotein-1b, or heat-shock protein 60/65, and parenteral (7-10) as well as oral (11-14) immunization reduced atherosclerotic disease in hyperlipidemic animals.

In some embodiments, antigen-specific immunoprotection can be achieved through several different mechanisms, such as production of protective antibodies, deletion or inactivation (anergy) of pathogenic T cell clones, or induction of suppressive cellular immunity mediated by the family of regulatory T cells (Treg) (15-16). In some of those embodiments, immunization with immunodominant peptide sequences can be performed in several cases in alternative to immunization with LDL particles (17-18).

In an embodiment, an immunization protocol that facilitates selective targeting of antigen-specific regulatory T cells can be performed. The type of immune response triggered is largely determined by the route of immunization.

In several embodiments, fusion products or antigenic fragments herein described can be administered to an individual using various routes of administration including subcutaneous, intramuscular, parenteral, and systemic and mucosal administration such as oral and/or nasal. In particular, the mucosal linings of airways and intestines contain lymphatic tissue that, when exposed to antigen, elicits anti-inflammatory, immunosuppressive responses (19). Distinct immunological features of the respiratory and intestinal mucosa lead to partly different types of protective immunity upon antigen exposure by the nasal or oral route (20). In some embodiments, the B subunit of cholera toxin (CTB) promotes uptake of antigen via the nasal and oral mucosa and induction of protective immunity (21, 22).

In some embodiments, administration of carrier/adjuvant/peptide vaccines is performed for a time and under condition to activate regulatory T cells and down-regulate pathogenic autoimmunity against Apo B.

In particular, in some embodiments, administration of a fusion protein is performed by nasal administration of an apoB100 peptide-CTB fusion protein (p210-CTB). In some embodiments, treatment with p210-CTB significantly reduced atherosclerosis in apoe$^{-/-}$ mice and was associated with induction of antigen-specific Treg activity.

In some embodiments, intranasal immunization with an apoB-100 fusion protein induces antigen-specific regulatory T cells and reduces atherosclerosis.

In several embodiments, nasal administration of an apoB100 peptide fused to CTB attenuates atherosclerosis and induces regulatory Tr1 cells that inhibit T effector responses to apolipoprotein B-100.

In some embodiments, fusion products, compositions and/or methods compositions herein described can be used a novel strategy for induction of atheroprotective immunity involving antigen-specific regulatory T cells. In particular, in several By nasal administration of a fusion protein between an immunodominant peptide of apoB-100 and immunomodulatory CTB, we were able to induce an atheroprotective immune response to apoB-100 that involved expansion of antigen-specific regulatory CD4$^+$ T cells and inhibition of aortic lesion development.

In several embodiments, induction of antigen-specific Treg with fusion protein methods and systems herein described provides atheroprotection using parenteral or oral routes for LDL immunization. Additionally, results illustrated in the Examples section concerning induction of antigen-specific atheroprotective immunity mucosal immunization in apoe$^{-/-}$ mice, which spontaneously develop atherosclerosis and are therefore already sensitized to plaque antigens such as LDL particles at the time of vaccination, supports the conclusion that a comparable approach in humans with pre-existing lesions is expected to provide immunization.

In some embodiments, herein described fusion proteins trigger a mechanism of atheroprotection where the atheroprotective effect paralleled an induction of Treg suppression of apoB-100-specific effector T cells and an increase in IL-10$^+$ CD4$^+$ T cells. In particular, in some embodiments, nasal immunization with p210-CTB protects against atherosclerosis by induction of antigen-specific, IL-10$^+$ regulatory Tr1 cells. A possible explanation that is provided herein for guidance purpose only and it is not intended to be limiting is that atheroprotection in several cases does not involve the immunosuppressive cytokine TGF-β since nasal immunization with p210-CTB reduced atherosclerosis also in mice lacking functional TGF-β receptors on T cells.

In some embodiments, fusion protein herein described provide an antigen-specific as well as antigen-independent effects similar to what reported in studies of Treg (25). In particular, in some embodiments, Treg suppress conventional effector T cells with the same antigen specificity. In some embodiments, Treg exert major effects on antigen-presenting cells in an antigen-independent manner. In some embodiments, the antigen-specific atheroprotection is paralleled by inhibition of apoB100-specific effector T cells by Treg specific for p210 but not OVA. These findings support a protective role for autoantigen-specific Treg in atherosclerosis.

In some embodiments, two major types of Treg induced in the periphery by antigen exposure have been identified: FoxP3$^+$ induced Treg (Th3)$^{14}$ and Tr1 cells (26). Tr1 cells are FoxP3 negative, secrete IL-10, and are believed to play an important role when regulatory immunity is induced by nasal immunization (27), (28). In some embodiments, where atheroprotection is induced by nasal immunization and associated with suppressor T cell activity and IL-10 producing CD4+ T cells, administration of fusion protein herein described is associated with Tr1 induction by p210-CTB. CD4+ T cells with antigen-specific suppressor activity were derived from spleen, a known reservoir of Tr1 cells (26).

In some embodiments, FoxP3$^+$ Treg can contribute to atheroprotection in this model following administration of a fusion protein herein described as indicated by an increase of FoxP3 mRNA was increased in the aorta of nasally immunized mice. In some embodiments, these cells can not only act directly to control proinflammatory effector T cells but also promote the activation of Tr1 cells (19). In some embodiments, wherein abrogation of TGF-β signaling is detected, Tr1 cells do not extinguish atheroprotection.

In some embodiments, where Treg markers are elevated also in OVA-CTB immunized mice, antigenically nonspecific effects can synergize with antigen-specific ones to confer protection.

In some embodiments, antibodies to the apoB100 peptide sequence are induced by nasal immunization, but do not crossreact with native mouse LDL particles. Furthermore, in some embodiments where particular antibody titers are not correlated with lesion size and no difference in lipoprotein profiles is detected between apoB-100-CTB immunized and OVA-CTB, immunized mice atheroprotection is associated to immunomodulation rather than antibody-dependent elimination of LDL.

In some embodiments, fusion proteins herein described are comprised in a composition together with suitable adjuvant and/or excipients.

The term adjuvant as used herein indicates a pharmacological or immunological agent that modify the effect of other agents (e.g., drugs, vaccines) while having few if any direct effects when given by themselves. They are often included in vaccines to enhance the recipient's immune response to a supplied antigen while keeping the injected foreign material at a minimum. Types of adjuvants include: Immunologic adjuvant that stimulate the immune system and increase the response to a vaccine, without having any specific antigenic effect in itself.

The term excipients as used herein indicates an inactive substance used as a carrier for the active ingredients of a medication. Exemplary excipients can also be used to bulk up formulations that contain very potent active ingredients, to allow for convenient and accurate dosage. In addition to their use in the single-dosage quantity, excipients can be used in the manufacturing process to aid in the handling of the active substance concerned. Depending on the route of administration, and form of medication, different excipients may be used that are identifiable by a skilled person.

In some embodiments, the compositions comprises selected (immunogenic) peptide fragments of apoB-100 (single or multiple copies) fused with a carrier molecule and possibly toxins/toxoids: tetanus toxin, diphtheria toxoid, B subunit of cholera toxin, as well as BSA, HAS, rHSA, KLH, ovalbumin In some embodiments, the adjuvants and excipients are pharmaceutically acceptable and the resulting composition is a pharmaceutical composition. In some of those embodiments, the pharmaceutical composition is a vaccine.

In some embodiments, adjuvants are components of the vaccine formulation that enhance immunogenicity of the antigen, for instance by promoting their uptake by antigen-presenting cells (17, 29). Interestingly, two studies documented an atheroprotective effect of complete Freund's adjuvant in hypercholesterolemic ldlr$^{-/-}$ and apoe$^{-/-}$ mice (30-31). In a recent study, subcutaneous administration of alum adjuvant was shown to increase antigen uptake and activation of cellular immune responses in hypercholesterolemic mice (32). In some embodiments, a specific antibody response against the apoB-100 peptide and an immunomodulatory cytokine profile in aortas of mice immunized with OVA-CTB described herein is in line with such an adjuvant effect. This further underlines the importance of using optimal immunomodulatory components in vaccine preparations.

In several embodiments, atheroprotective vaccine is provided by targeting a peptide of the LDL protein constituent apolipoprotein B-100 to the nasal mucosa to induce a protective mucosal immune response.

Further details concerning the implementation of the fusion products methods herein described including systems for performance of the methods which can be in the form of kit of parts as well as related compositions including donors, acceptors, compounds and other reagents together with suitable carrier, agent or auxiliary agent of the compositions, and generally manufacturing and packaging of the kit, can be identified by the person skilled in the art upon reading of the present disclosure.

EXAMPLES

The fusion proteins and related compositions methods and systems herein described are further illustrated in the following examples, which are provided by way of illustration and are not intended to be limiting.

In particular, the following examples illustrate an exemplary immunization performed with a fusion protein comprising amino acids 3136-3155 of human apoB-100 (p210) fused with CTB identified also as p210-CTB. A person skilled in the art will appreciate the applicability of the features described in detail for P210-CTB for additional fusion protein comprising another antigenic peptide of apoB-100 and a carrier molecule according to the present disclosure.

More particular, in the following examples the recombinant protein, p210-CTB, was made from amino acids 3136-3155 of human apoB-100 (p210)[15] fused with CTB. This sequence is identical to the corresponding murine sequence with the exception of a 2-residue insert at the C-terminal end in the mouse. As a control, amino acids 323-339 of ovalbumin were fused to CTB (OVA-CTB). 8-week-old female apoe$^{-/-}$ mice received a nasal spray with 15 μG (in 15 μL) p210-CTB or OVA-CTB twice weekly. Lesions and immune parameters were analyzed 12 weeks later. In another set of experiments, apoe$^{-/-}$xCD4dnTGFbRII mice (23) were immunized using the same protocol. All experiments were approved by the Stockholm regional ethical board. Atherosclerotic lesions were analyzed in cryostat sections of the aortic root using a standardized protocol (24). Antibodies to p210 and to mouse LDL particles were analyzed by immunometric ELISA[15].

Antigen-specific Treg activity was analyzed in the following way: apoe$^{-/-}$ mice were immunized subcutaneously with apoB-100 to generate effector T cells. CD4$^+$ T cells from these mice were exposed to antigen and activation recorded as DNA synthesis. CD4$^+$ T cells from apoe$^{-/-}$ mice immunized intranasally with p210-CTB were added to effector T cell preparations and Treg activity was recorded as inhibition of DNA synthesis. Intracellular staining was performed on CD4$^+$ T cells to characterize cytokine production and T cell subtype.

Additional details concerning procedures used and results obtained are reported below.

Example 1

Generation of Peptide Library

Specific immunogenic epitopes by focusing on the single protein found in LDL, apolipoprotein B-100 (apo B) were characterized. A peptide library comprised of 302 peptides, 20 amino acid residues in length, covering the complete 4563 amino acid sequence of human apo B was produced. The peptides were produced with a 5 amino acid overlap to cover all sequences at break points. Peptides were numbered 1-302 starting at the N-terminal of apo B as indicated in Table 1 below.

TABLE 1

| Peptide | Sequence | Apolipoprotein B aa | SEQ ID NO |
|---|---|---|---|
| P1: | EEEML ENVSL VCPKD ATRFK | aa 1-20 | 1 |
| P2: | ATRFK HLRKY TYNYE AESSS | aa 16-35 | 2 |
| P3: | AESSS GVPGT ADSRS ATRIN | aa 31-50 | 3 |
| P4: | ATRIN CKVEL EVPQL CSFIL | aa 46-65 | 4 |
| P5: | CSFIL KTSQC TLKEV YGFNP | aa 61-80 | 5 |
| P6: | YGFNP EGKAL LKKTK NSEEF | aa 76-95 | 6 |
| P7: | NSEEF AAAMS RYELK LAIPE | aa 91-110 | 7 |
| P8: | LAIPE GKQVF LYPEK DEPTY | aa 106-125 | 8 |
| P9: | DEPTY ILNIK RGIIS ALLVP | aa 121-140 | 9 |
| P10: | ALLVP PETEE AKQVL FLDTV | aa 136-155 | 10 |
| P11: | FLDTV YGNCS THFTV KTRKG | aa 151-170 | 11 |
| P12: | KTRKG NVATE ISTER DLGQC | aa 166-185 | 12 |
| P13: | DLGQC DRFKP IRTGI SPLAL | aa 181-200 | 13 |
| P14: | SPLAL IKGMT RPLST LISSS | aa 196-215 | 14 |
| P15: | LISSS QSCQY TLDAK RKHVA | aa 211-230 | 15 |
| P16: | RKHVA EAICK EQHLF LPFSY | aa 226-245 | 16 |
| P17: | LPFSY NNKYG MVAQV TQTLK | aa 241-260 | 17 |
| P18: | TQTLK LEDTP KINSR FFGEG | aa 256-275 | 18 |
| P19: | FFGEG TKKMG LAFES TKSTS | aa 271-290 | 19 |
| P20: | TKSTS PPKQA EAVLK TLQEL | aa 286-305 | 20 |
| P21: | TLQEL KKLTI SEQNI QRANL | aa 301-320 | 21 |
| P22: | QRANL FNKLV TELRG LSDEA | aa 316-335 | 22 |
| P23: | LSDEA VTSLL PQLIE VSSPI | aa 331-350 | 23 |
| P24: | VSSPI TLQAL VQCGQ PQCST | aa 346-365 | 24 |
| P25: | PQCST HILQW LKRVH ANPLL | aa 361-380 | 25 |
| P26: | ANPLL IDVVT YLVAL IPEPS | aa 376-395 | 26 |
| P27: | IPEPS AQQLR EIFNM ARDQR | aa 391-410 | 27 |
| P28: | ARDQR SRATL YALSH AVNNY | aa 406-425 | 28 |
| P29: | AVNNY HKTNP TGTQE LLDIA | aa 421-440 | 29 |
| P30: | LLDIA NYLME QIQDD CTGDE | aa 436-455 | 30 |
| P31: | CTGDE DYTYL ILRVI GNMGQ | aa 451-470 | 31 |
| P32: | GNMGQ TMEQL TPELK SSILK | aa 466-485 | 32 |
| P33: | SSILK CVQST KPSLM IQKAA | aa 481-500 | 33 |
| P34: | IQKAA IQALR KMEPK DKDQE | aa 496-515 | 34 |
| P35: | DKDQE VLLQT FLDDA SPGDK | aa 511-530 | 35 |
| P36: | SPGDK RLAAY LMLMR SPSQA | aa 526-545 | 36 |
| P37: | SPSQA DINKI VQILP WEQNE | aa 541-560 | 37 |
| P38: | WEQNE QVKNF VASHI ANILN | aa 556-575 | 38 |
| P39: | ANILN SEELD IQDLK KLVKE | aa 571-590 | 39 |
| P40: | KLVKE ALKES QLPTV MDFRK | aa 586-605 | 40 |
| P41: | MDFRK FSRNY QLYKS VSLPS | aa 601-620 | 41 |

TABLE 1-continued

| Peptide | Sequence | Apolipoprotein B aa | SEQ ID NO |
|---|---|---|---|
| P42: | VSLPS LDPAS AKIEG NLIFD | aa 616-635 | 42 |
| P43: | NLIFD PNNYL PKESM LKTTL | aa 631-650 | 43 |
| P44: | LKTTL TAFGF ASADL IEIGL | aa 646-665 | 44 |
| P45: | IEIGL EGKGF EPTLE ALFGK | aa 661-680 | 45 |
| P46: | ALFGK QGFFP DSVNK ALYWV | aa 676-695 | 46 |
| P47: | ALYWV NGQVP DGVSK VLVDH | aa 691-710 | 47 |
| P48: | VLVDH FGYTK DDKHE QDMVN | aa 706-725 | 48 |
| P49: | QDMVN GIMLS VEKLI KDLKS | aa 721-740 | 49 |
| P50: | KDLKS KEVPE ARAYL RILGE | aa 736-755 | 50 |
| P51: | RILGE ELGFA SLHDL QLLGK | aa 751-770 | 51 |
| P52: | QLLGK LLLMG ARTLQ GIPQM | aa 766-785 | 52 |
| P53: | GIPQM IGEVI RKGSK NDFFL | aa 781-800 | 53 |
| P54: | NDFFL HYIFM ENAFE LPTGA | aa 796-815 | 54 |
| P55: | LPTGA GLQLQ ISSSG VIAPG | aa 811-830 | 55 |
| P56: | VIAPG AKAGV KLEVA NMQAE | aa 826-845 | 56 |
| P57: | NMQAE LVAKP SVSVE FVTNM | aa 841-860 | 57 |
| P58: | FVTNM GIIIP DFARS GVQMN | aa 856-875 | 58 |
| P59: | GVQMN TNFFH ESGLE AHVAL | aa 871-890 | 59 |
| P60: | AHVAL KAGKL KFIIP SPKRP | aa 886-905 | 60 |
| P61: | SPKRP VKLLS GGNTL HLVST | aa 901-920 | 61 |
| P62: | HLVST TKTEV IPPLI ENRQS | aa 916-935 | 62 |
| P63: | ENRQS WSVCK QVFPG LNYCT | aa 931-950 | 63 |
| P64: | LNYCT SGAYS NASST DSASY | aa 946-965 | 64 |
| P65: | DSASY YPLTG DTRLE LELRP | aa 961-980 | 65 |
| P66: | LELRP TGEIE QYSVS ATYEL | aa 976-995 | 66 |
| P67: | ATYEL QREDR ALVDT LKFVT | aa 991-1010 | 67 |
| P68: | LKFVT QAEGA KQTEA TMTFK | aa 1006-1025 | 68 |
| P69: | TMTFK YNRQS MTLSS EVQIP | aa 1021-1040 | 69 |
| P70: | EVQIP DFDVD LGTIL RVNDE | aa 1036-1055 | 70 |
| P71: | RVNDE STEGK TSYRL TLDIQ | aa 1051-1070 | 71 |
| P72: | TLDIQ NKKIT EVALM GHLSC | aa 1066-1085 | 72 |
| P73: | GHLSC DTKEE RKIKG VISIP | aa 1081-1100 | 73 |
| P74: | VISIP RLQAE ARSEI LAHWS | aa 1096-1115 | 74 |
| P75: | LAHWS PAKLL LQMDS SATAY | aa 1111-1130 | 75 |
| P76: | SATAY GSTVS KRVAW HYDEE | aa 1126-1145 | 76 |
| P77: | HYDEE KIEFE WNTGT NVDTK | aa 1141-1160 | 77 |
| P78: | NVDTK KMTSN FPVDL SDYPK | aa 1156-1175 | 78 |
| P79: | SDYPK SLHMY ANRLL DHRVP | aa 1171-1190 | 79 |
| P80: | DHRVP ETDMT FRHVG SKLIV | aa 1186-1205 | 80 |
| P81: | SKLIV AMSSW LQKAS GSLPY | aa 1201-1220 | 81 |
| P82: | GSLPY TQTLQ DHLNS LKEFN | aa 1216-1235 | 82 |
| P83: | LKEFN LQNMG LPDFH IPENL | aa 1231-1250 | 83 |
| P84: | IPENL FLKSD GRVKY TLNKN | aa 1246-1260 | 84 |
| P85: | TLNKN SLKIE IPLPF GGKSS | aa 1261-1280 | 85 |
| P86: | GGKSS RDLKM LETVR TPALH | aa 1276-1295 | 86 |
| P87: | TPALH FKSVG FHLPS REFQV | aa 1291-1310 | 87 |
| P88: | REFQV PTFTI PKLYQ LQVPL | aa 1306-1325 | 88 |
| P89: | LQVPL LGVLD LSTNV YSNLY | aa 1321-1340 | 89 |
| P90: | YSNLY NWSAS YSGGN TSTDH | aa 1336-1355 | 90 |
| P91: | TSTDH FSLRA RYHMK ADSVV | aa 1351-1370 | 91 |
| P92: | ADSVV DLLSY NVQGS GETTY | aa 1366-1385 | 92 |
| P93: | GETTY DHKNT FTLSC DGSLR | aa 1381-1400 | 93 |
| P94: | DGSLR HKFLD SNIKF SHVEK | aa 1396-1415 | 94 |
| P95: | SHVEK LGNNP VSKGL LIFDA | aa 1411-1430 | 95 |
| P96: | LIFDA SSSWG PQMSA SVHLD | aa 1426-1445 | 96 |
| P97: | SVHLD SKKKQ HLFVK EVKID | aa 1441-1460 | 97 |
| P98: | EVKID GQFRV SSFYA KGTYG | aa 1456-1475 | 98 |
| P99: | KGTYG LSCQR DPNTG RLNGE | aa 1471-1490 | 99 |
| P100: | RLNGE SNLRF NSSYL QGTNQ | aa 1486-1505 | 100 |
| P101: | QGTNQ ITGRY EDGTL SLTST | aa 1501-1520 | 101 |
| P102: | SLTST SDLQS GIIKN TASLK | aa 1516-1535 | 102 |
| P103: | TASLK YENYE LTLKS DTNGK | aa 1531-1550 | 103 |
| P104: | DTNGK YKNFA TSNKM DMTFS | aa 1546-1565 | 104 |
| P105: | DMTFS KQNAL LRSEY QADYE | aa 1561-1580 | 105 |
| P106: | QADYE SLRFF SLLSG SLNSH | aa 1576-1595 | 106 |
| P107: | SLNSH GLELN ADILG TDKIN | aa 1591-1610 | 107 |
| P108: | TDKIN SGAHK ATLRI GQDGI | aa 1606-1625 | 108 |
| P109: | GQDGI STSAT TNLKC SLLVL | aa 1621-1640 | 109 |
| P110: | SLLVL ENELN AELGL SGASM | aa 1636-1655 | 110 |
| P111: | SGASM KLTTN GRFRE HNAKF | aa 1651-1670 | 111 |
| P112: | HNAKF SLDGK AALTE LSLGS | aa 1666-1685 | 112 |
| P113: | LSLGS AYQAM ILGVD SKNIF | aa 1681-1700 | 113 |
| P114: | SKNIF NFKVS QEGLK LSNDM | aa 1696-1715 | 114 |
| P115: | LSNDM MGSYA EMKFD HTNSL | aa 1711-1730 | 115 |
| P116: | HTNSL NIAGL SLDFS SKLDN | aa 1726-1745 | 116 |
| P117: | SKLDN IYSSD KFYKQ TVNLQ | aa 1741-1760 | 117 |

TABLE 1-continued

| Peptide | Sequence | Apolipoprotein B aa | SEQ ID NO |
|---|---|---|---|
| P118: | TVNLQ LQPYS LVTTL NSDLK | aa 1756-1775 | 118 |
| P119: | NSDLK YNALD LTNNG KLRLE | aa 1771-1790 | 119 |
| P120: | KLRLE PLKLH VAGNL KGAYQ | aa 1786-1805 | 120 |
| P121: | KGAYQ NNEIK HIYAI SSAAL | aa 1801-1820 | 121 |
| P122: | SSAAL SASYK ADTVA KVQGV | aa 1816-1835 | 122 |
| P123: | KVQGV EFSHR LNTDI AGLAS | aa 1831-1850 | 123 |
| P124: | AGLAS AIDMS TNYNS DSLHF | aa 1846-1865 | 124 |
| P125: | DSLHF SNVFR SVMAP FTMTI | aa 1861-1880 | 125 |
| P126: | FTMTI DAHTN GNGKL ALWGE | aa 1876-1895 | 126 |
| P127: | ALWGE HTGQL YSKFL LKAEP | aa 1891-1910 | 127 |
| P128: | LKAEP LAFTF SHDYK GSTSH | aa 1906-1925 | 128 |
| P129: | GSTSH HLVSR KSISA ALEHK | aa 1921-1940 | 129 |
| P130: | ALEHK VSALL TPAEQ TGTWK | aa 1936-1955 | 130 |
| P131: | TGTWK LKTQF NNNEY SQDLD | aa 1951-1970 | 131 |
| P132: | SQDLD AYNTK DKIGV ELTGR | aa 1966-1985 | 132 |
| P133: | ELTGR TLADL TLLDS PIKVP | aa 1981-2000 | 133 |
| P134: | PIKVP LLLSE PINII DALEM | aa 1996-2015 | 134 |
| P135: | DALEM RDAVE KPQEF TIVAF | aa 2011-2030 | 135 |
| P136: | TIVAF VKYDK NQDVH SINLP | aa 2026-2045 | 136 |
| P137: | SINLP FFETL QEYFE RNRQT | aa 2041-2060 | 137 |
| P138: | RNRQT IIVVV ENVQR NLKHI | aa 2056-2075 | 138 |
| P139: | NLKHI NIDQF VRKYR AALGK | aa 2071-2090 | 139 |
| P140: | AALGK LPQQA NDYLN SFNWE | aa 2086-2105 | 140 |
| P141: | SFNWE RQVSH AKEKL TALTK | aa 2101-2120 | 141 |
| P142: | TALTK KYRIT ENDIQ IALDD | aa 2116-2135 | 142 |
| P143: | IALDD AKINF NEKLS QLQTY | aa 2131-2150 | 143 |
| P144: | QLQTY MIQFD QYIKD SYDLH | aa 2146-2165 | 144 |
| P145: | SYDLH DLKIA IANII DEIIE | aa 2161-2180 | 145 |
| P146: | DEIIE KLKSL DEHYH IRVNL | aa 2176-2195 | 146 |
| P147: | IRVNL VKTIH DLHLF IENID | aa 2191-2210 | 147 |
| P148: | IENID FNKSG SSTAS WIQNV | aa 2206-2225 | 148 |
| P149: | WIQNV DTKYQ IRIQI QEKLQ | aa 2221-2240 | 149 |
| P150: | QEKLQ QLKRH IQNID IQHLA | aa 2236-2255 | 150 |
| P151: | IQHLA GKLKQ HIEAI DVRVL | aa 2251-2270 | 151 |
| P152: | DVRVL LDQLG TTISF ERIND | aa 2266-2285 | 152 |
| P153: | ERIND VLEHV KHFVI NLIGD | aa 2281-2300 | 153 |
| P154: | NLIGD FEVAE KINAF RAKVH | aa 2296-2315 | 154 |
| P155: | RAKVH ELIER YEVDQ QIQVL | aa 2311-2330 | 155 |
| P156: | QIQVL MDKLV ELTHQ YKLKE | aa 2326-2345 | 156 |
| P157: | YKLKE TIQKL SNVLQ QVKIK | aa 2341-2360 | 157 |
| P158: | QVKIK DYFEK LVGFI DDAVK | aa 2356-2375 | 158 |
| P159: | DDAVK KLNEL SFKTF IEDVN | aa 2371-2390 | 159 |
| P160: | IEDVN KFLDM LIKKL KSFDY | aa 2386-2405 | 160 |
| P161: | KSFDY HQFVD ETNDK IREVT | aa 2401-2420 | 161 |
| P162: | IREVT QRLNG EIQAL ELPQK | aa 2416-2435 | 162 |
| P163: | ELPQK AEALK LFLEE TKATV | aa 2431-2450 | 163 |
| P164: | TKATV AVYLE SLQDT KITLI | aa 2446-2465 | 164 |
| P165: | KITLI INWLQ EALSS ASLAH | aa 2461-2480 | 165 |
| P166: | ASLAH MKAKF RETLE DTRDR | aa 2476-2495 | 166 |
| P167: | DTRDR MYQMD IQQEL QRYLS | aa 2491-2510 | 167 |
| P168: | QRYLS LVGQV YSTLV TYISD | aa 2506-2515 | 168 |
| P169: | TYISD WWTLA AKNLT DFAEQ | aa 2521-2540 | 169 |
| P170: | DFAEQ YSIQD WAKRM KALVE | aa 2536-2555 | 170 |
| P171: | KALVE QGFTV PEIKT ILGTM | aa 2551-2570 | 171 |
| P172: | ILGTM PAFEV SLQAL QKATF | aa 2566-2585 | 172 |
| P173: | QKATF QTPDF IVPLT DLRIP | aa 2581-2600 | 173 |
| P174: | DLRIP SVQIN FKDLK NIKIP | aa 2596-2615 | 174 |
| P175: | NIKIP SRFST PEFTI LNTFH | aa 2611-2630 | 175 |
| P176: | LNTFH IPSFT IDFVE MKVKI | aa 2626-2645 | 176 |
| P177: | MKVKI IRTID QMQNS ELQWP | aa 2641-2660 | 177 |
| P178: | ELQWP VPDIY LRDLK VEDIP | aa 2656-2675 | 178 |
| P179: | VEDIP LARIT LPDFR LPEIA | aa 2671-2690 | 179 |
| P180: | LPEIA IPEFI IPTLN LNDFQ | aa 2686-2705 | 180 |
| P181: | LNDFQ VPDLH IPEFQ LPHIS | aa 2701-2720 | 181 |
| P182: | LPHIS HTIEV PTFGK LYSIL | aa 2716-2735 | 182 |
| P183: | LYSIL KIQSP LFTLD ANADI | aa 2731-2750 | 183 |
| P184: | ANADI GNGTT SANEA GIAAS | aa 2746-2765 | 184 |
| P185: | GIAAS ITAKG ESKLE VLNFD | aa 2761-2780 | 185 |
| P186: | VLNFD FQANA QLSNP KINPL | aa 2776-2795 | 186 |
| P187: | KINPL ALKES VKFSS KYLRT | aa 2791-2810 | 187 |
| P188: | KYLRT EHGSE MLFFG NAIEG | aa 2806-2825 | 188 |
| P189: | NAIEG KSNTV ASLHT EKNTL | aa 2821-2840 | 189 |
| P190: | EKNTL ELSNG VIVKI NNQLT | aa 2836-2855 | 190 |
| P191: | NNQLT LDSNT KYFHK LNIPK | aa 2851-2870 | 191 |
| P192: | LNIPK LDFSS QADLR NEIKT | aa 2866-2885 | 192 |
| P193: | NEIKT LLKAG HIAWT SSGKG | aa 2881-2900 | 193 |

TABLE 1-continued

| Peptide | Sequence | Apolipo-protein B aa | SEQ ID NO |
|---|---|---|---|
| P194: | SSGKG SWKWA CPRFS DEGTH | aa 2896-2915 | 194 |
| P195: | DEGTH ESQIS FTIEG PLTSF | aa 2911-2930 | 195 |
| P196: | PLTSF GLSNK INSKH LRVNQ | aa 2926-2945 | 196 |
| P197: | LRVNQ NLVYE SGSLN FSKLE | aa 2941-2960 | 197 |
| P198: | FSKLE IQSQV DSQHV GHSVL | aa 2956-2975 | 198 |
| P199: | GHSVL TAKGM ALFGE GKAEF | aa 2971-2990 | 199 |
| P200: | GKAEF TGRHD AHLNG KVIGT | aa 2986-3005 | 200 |
| P201: | KVIGT LKNSL FFSAQ PFEIT | aa 3001-3020 | 201 |
| P202: | PFEIT ASTNN EGNLK VRFPL | aa 3016-3035 | 202 |
| P203: | VRFPL RLTGK IDFLN NYALF | aa 3031-3050 | 203 |
| P204: | NYALF LSPSA QQASW QVSAR | aa 3046-3065 | 204 |
| P205: | QVSAR FNQYK YNQNF SAGNN | aa 3061-3080 | 205 |
| P206: | SAGNN ENIME AHVGI NGEAN | aa 3076-3095 | 206 |
| P207: | NGEAN LDFLN IPLTI PEMRL | aa 3091-3110 | 207 |
| P208: | PEMRL PYTII TTPPL KDFSL | aa 3106-3125 | 208 |
| P209: | KDFSL WEKTG LKEFL KTTKQ | aa 3121-3140 | 209 |
| P210: | KTTKQ SFDLS VKAQY KKNKH | aa 3136-3155 | 210 |
| P211: | KKNKH RHSIT NPLAV LCEFI | aa 3151-3170 | 211 |
| P212: | LCEFI SQSIK SFDRH FEKNR | aa 3166-3185 | 212 |
| P213: | FEKNR NNALD FVTKS YNETK | aa 3181-3200 | 213 |
| P214: | YNETK IKFDK YKAEK SHDEL | aa 3196-3215 | 214 |
| P215: | SHDEL PRTFQ IPGYT VPVVN | aa 3211-3230 | 215 |
| P216: | VPVVN VEVSP FTIEM SAFGY | aa 3226-3245 | 216 |
| P217: | SAFGY VFPKA VSMPS FSILG | aa 3241-3260 | 217 |
| P218: | FSILG SDVRV PSYTL ILPSL | aa 3256-3275 | 218 |
| P219: | ILPSL ELPVL HVPRN LKLSL | aa 3271-3290 | 219 |
| P220: | LKLSL PHFKE LCTIS HIFIP | aa 3286-3305 | 220 |
| P221: | HIFIP AMGNI TYDFS FKSSV | aa 3301-3320 | 221 |
| P222: | FKSSV ITLNT NAELF NQSDI | aa 3316-3335 | 222 |
| P223: | NQSDI VAHLL SSSSS VIDAL | aa 3331-3350 | 223 |
| P224: | VIDAL QYKLE GTTRL TRKRG | aa 3346-3365 | 224 |
| P225: | TRKRG LKLAT ALSLS NKFVE | aa 3361-3380 | 225 |
| P226: | NKFVE GSHNS TVSLT TKNME | aa 3376-3395 | 226 |
| P227: | TKNME VSVAK TTKAE IPILR | aa 3391-3410 | 227 |
| P228: | IPILR MNFKQ ELNGN TKSKP | aa 3406-3425 | 228 |
| P229: | TKSKP TVSSS MEFKY DFNSS | aa 3421-3440 | 229 |
| P230: | DFNSS MLYST AKGAV DHKLS | aa 3436-3455 | 230 |
| P231: | DHKLS LESLT SYFSI ESSTK | aa 3451-3470 | 231 |
| P232: | ESSTK GDVKG SVLSR EYSGT | aa 3466-3485 | 232 |
| P233: | EYSGT IASEA NTYLN SKSTR | aa 3481-3500 | 233 |
| P234: | SKSTR SSVKL QGTSK IDDIW | aa 3496-3515 | 234 |
| P235: | IDDIW NLEVK ENFAG EATLQ | aa 3511-3530 | 235 |
| P236: | EATLQ RIYSL WEHST KNHLQ | aa 3526-3545 | 236 |
| P237: | KNHLQ LEGLF TNGE HTSKA | aa 3541-3560 | 237 |
| P238: | HTSKA TLELS PWQMS ALVQV | aa 3556-3575 | 238 |
| P239: | ALVQV HASQP SSFHD FPDLG | aa 3571-3590 | 239 |
| P240: | FPDLG QEVAL NANTK NQKIR | aa 3586-3605 | 240 |
| P241: | NQKIR WKNEV RIHSG SFQSQ | aa 3601-3620 | 241 |
| P242: | SFQSQ VELSN DQEKA HLDIA | aa 3616-3635 | 242 |
| P243: | HLDIA GSLEG HLRFL KNIIL | aa 3631-3650 | 243 |
| P244: | KNIIL PVYDK SLWDF LKLDV | aa 3646-3665 | 244 |
| P245: | LKLDV TTSIG RRQHL RVSTA | aa 3661-3680 | 245 |
| P246: | RVSTA FVYTK NPNGY SFSIP | aa 3676-3695 | 246 |
| P247: | SFSIP VKVLA DKFIT PGLKL | aa 3691-3710 | 247 |
| P248: | PGLKL NDLNS VLVMP TFHVP | aa 3706-3725 | 248 |
| P249: | TFHVP FTDLQ VPSCK LDFRE | aa 3721-3740 | 249 |
| P250: | LDFRE IQIYK KLRTS SFALN | aa 3736-3755 | 250 |
| P251: | SFALN LPTLP EVKFP EVDVL | aa 3751-3770 | 251 |
| P252: | EVDVL TKYSQ PEDSL IPFFE | aa 3766-3785 | 252 |
| P253: | IPFFE ITVPE SQLTV SQFTL | aa 3781-3800 | 253 |
| P254: | SQFTL PKSVS DGIAA LDLNA | aa 3796-3815 | 254 |
| P255: | LDLNA VANKI ADFEL PTIIV | aa 3811-3830 | 255 |
| P256: | PTIIV PEQTI EIPSI KFSVP | aa 3826-3845 | 256 |
| P257: | KFSVP AGIVI PSFQA LTARF | aa 3841-3860 | 257 |
| P258: | LTARF EVDSP VYNAT WSASL | aa 3856-3875 | 258 |
| P259: | WSASL KNKAD YVETV LDSTC | aa 3871-3890 | 259 |
| P260: | LDSTC SSTVQ FLEYE LNVLG | aa 3886-3905 | 260 |
| P261: | LNVLG THKIE DGTLA SKTKG | aa 3901-3920 | 261 |
| P262: | SKTKG TLAHR DFSAE YEEDG | aa 3916-3935 | 262 |
| P263: | YEEDG KFEGL QEWEG KAHLN | aa 3931-3950 | 263 |
| P264: | KAHLN IKSPA FTDLH LRYQK | aa 3946-3965 | 264 |
| P265: | LRYQK DKKGI STSAA SPAVG | aa 3961-3980 | 265 |
| P266: | SPAVG TVGMD MDEDD DFSKW | aa 3976-3995 | 266 |
| P267: | DFSKW NFYYS PQSSP DKKLT | aa 3991-4010 | 267 |
| P268: | DKKLT IFKTE LRVRE SDEET | aa 4006-4025 | 268 |
| P269: | SDEET QIKVN WEEEA ASGLL | aa 4021-4040 | 269 |

TABLE 1-continued

| Peptide | Sequence | Apolipoprotein B aa | SEQ ID NO |
|---|---|---|---|
| P270: | ASGLL TSLKD NVPKA TGVLY | aa 4036-4055 | 270 |
| P271: | TGVLY DYVNK YHWEH TGLTL | aa 4051-4070 | 271 |
| P272: | TGLTL REVSS KLRRN LQNNA | aa 4066-4085 | 272 |
| P273: | LQNNA EWVYQ GAIRQ IDDID | aa 4081-4100 | 273 |
| P274: | IDDID VRFQK AASGT TGTYQ | aa 4096-4115 | 274 |
| P275: | TGTYQ EWKDK AQNLY QELLT | aa 4111-4130 | 275 |
| P276: | QELLT QEGQA SFQGL KDNVF | aa 4126-4145 | 276 |
| P277: | KDNVF DGLVR VTQKF HMKVK | aa 4141-4160 | 277 |
| P278: | HMKVK HLIDS LIDFL NFPRF | aa 4156-4175 | 278 |
| P279: | NFPRF QFPGK PGIYT REELC | aa 4171-4190 | 279 |
| P280: | REELC TMFIR EVGTV LSQVY | aa 4186-4205 | 280 |
| P281: | LSQVY SKVHN GSEIL FSYFQ | aa 4201-4220 | 281 |
| P282: | FSYFQ DLVIT LPFEL RKHKL | aa 4216-4235 | 282 |
| P283: | RKHKL IDVIS MYREL LKDLS | aa 4231-4250 | 283 |
| P284: | LKDLS KEAQE VFKAI QSLKT | aa 4246-4265 | 284 |
| P285: | QSLKT TEVLR NLQDL LQFIF | aa 4261-4280 | 285 |
| P286: | LQFIF QLIED NIKQL KEMKF | aa 4276-4295 | 286 |
| P287: | KEMKF TYLIN YIQDE INTIF | aa 4291-4310 | 287 |
| P288: | INTIF NDYIP YVFKL LKENL | aa 4306-4325 | 288 |
| P289: | LKENL CLNLH KFNEF IQNEL | aa 4321-4340 | 289 |
| P290: | IQNEL QEASQ ELQQI HQYIM | aa 4336-4355 | 290 |
| P291: | HQYIM ALREE YFDPS IVGWT | aa 4351-4370 | 291 |
| P292: | IVGWT VKYYE LEEKI VSLIK | aa 4366-4385 | 292 |
| P293: | VSLIK NLLVA LKDFH SEYIV | aa 4381-4400 | 293 |
| P294: | SEYIV SASNF TSQLS SQVEQ | aa 4396-4415 | 294 |
| P295: | SQVEQ FLHRN IQEYL SILTD | aa 4411-4430 | 295 |
| P296: | SILTD PDGKG KEKIA ELSAT | aa 4426-4445 | 296 |
| P297: | ELSAT AQEII KSQAI ATKKI | aa 4441-4460 | 297 |
| P298: | TKKII SDYHQ QFRYK LQDFS | aa 4457-4476 | 298 |
| P299: | LQDFS DQLSD YYEKF IAESK | aa 4472-4491 | 299 |
| P300: | IAESK RLTDL SIQNY HTFLI | aa 4487-4506 | 300 |
| P301: | HTFLI YITEL LKKLQ STTVM | aa 4502-4521 | 301 |
| P302: | STTVM NPYMK LAPGE LTIIL | aa 4517-4536 | 302 |

Example 2

ApoB-100-Peptides Selection

Plasma samples were obtained from 10 patients with clinically evident atherosclerotic heart disease. In addition, 50 plasma samples were obtained from 25 men and 25 women with no evidence of atherosclerotic heart disease. Samples of the 20 amino acid long peptides were adsorbed to microtiter plates to perform enzyme-linked immunosorbent assay (ELISA) analyses of the plasma samples. Peptides were used in their native state or after oxidation by exposure to copper or after modification by malondialdehyde (MDA).

Plasma samples from patients and normal subjects contained antibodies to a large number of different peptides. Antibodies against both native and modified peptides were identified. A total of 38 peptide sequences were identified as potential targets for immune reactions that may be of importance for the development of atherosclerosis.

The peptide sequences against which the highest antibody levels were detected could be divided in six groups with certain common characteristics as indicated in Table 2 below.

TABLE 2

| Peptide | Sequence | Apo B-100 Amino Acid | SEQ ID NO |
|---|---|---|---|
| A. High levels of IgG antibodies to MDA modified peptides (n = 3) ||||
| P11 | FLDTV-YGNCS-THFTV-KTRKG | 151-170 | 11 |
| P25 | PQCST-HILQW-LKRVH-ANPLL | 361-380 | 25 |
| P74 | VISIP-RLQAE-ARSEI-LAHWS | 1096-1115 | 74 |
| B. High levels of IgM antibodies, no difference between native and MDA-modified peptides (n = 9) ||||
| P40 | KLVKE-ALKES-QLPTV-MDFRK | 586-605 | 40 |
| P94 | DGSLR-HKFLD-SNIKF-SHVEK | 1396-1415 | 94 |
| P99 | KGTYG-LSCQR-DPNTG-RLNGE | 1471-1490 | 99 |

TABLE 2-continued

| Peptide | Sequence | Apo B-100 Amino Acid | SEQ ID NO |
|---|---|---|---|
| P100 | RLNGE-SNLRF-NSSYL-QGTNQ | 1486-1505 | 100 |
| P102 | SLTST-SDLQS-GIIKN-TASLK | 1516-1535 | 102 |
| P103 | TASLK-YENYE-LTLKS-DTNGK | 1531-1550 | 103 |
| P105 | DMTFS-KQANL-LRSEY-QADYE | 1561-1580 | 105 |
| P177 | MKVKI-IRTID-QMQNS-ELQWP | 2641-2660 | 177 |

C. High levels of IgG antibodies, no difference between native and MDA-modified peptides (n = 2)

| Peptide | Sequence | Apo B-100 Amino Acid | SEQ ID NO |
|---|---|---|---|
| P143 | IALDD-AKINF-NEKLS-QLQTY | 2131-2150 | 143 |
| P210 | KTTKQ-SFDLS-VKAQY-KKNKH | 3136-3155 | 210 |

D. High levels of IgG antibodies to MDA-modified peptides and at least twice as much antibodies in the plasma of normal subjects as compared to the plasma of individuals with atherosclerosis (n = 5)

| Peptide | Sequence | Apo B-100 Amino Acid | SEQ ID NO |
|---|---|---|---|
| P1 | EEEML-ENVSL-VCPKD-ATRFK | 1-20 | 1 |
| P129 | GSTSH-HLVSR-KSISA-ALEHK | 1921-1940 | 129 |
| P148 | IENID-FNKSG-SSTAS-WIQNV | 2206-2225 | 148 |
| P162 | IREVT-QRLNG-EIQAL-ELPQK | 2416-2435 | 162 |
| P252 | EVDVL-TKYSQ-PEDSL-IPFFE | 3766-3785 | 252 |

E. High levels of IgM antibodies to MDA-modified peptides and at least twice as much antibodies in the plasma of normal subjects as compared to the plasma of individuals with atherosclerosis (n = 11)

| Peptide | Sequence | Apo B-100 Amino Acid | SEQ ID NO |
|---|---|---|---|
| P30 | LLDIA-NYLME-QIQDD-CTGDE | 436-455 | 30 |
| P31 | CTGDE-DYTYK-IKRVI-GNMGQ | 451-470 | 31 |
| P32 | GNMGQ-TMEQL-TPELK-SSILK | 466-485 | 32 |
| P33 | SSILK-CVQST-KPSLM-IQKAA | 481-500 | 33 |
| P34 | IQKAA-IQALR-KMEPK-DKDQE | 496-515 | 34 |
| P100 | RLNGE-SNLRF-NSSYL-QGTNQ | 1486-1505 | 100 |
| P107 | SLNSH-GLELN-ADILG-TDKIN | 1591-1610 | 107 |
| P149 | WIQNV-DTKYQ-IRIQI-QEKLQ | 2221-2240 | 149 |
| P169 | TYISD-WWTLA-AKNLT-DFAEQ | 2521-2540 | 169 |
| P236 | EATLQ-RIYSL-WEHST-KNHLQ | 3526-3545 | 236 |
| P301 | HTFLI-YITEL-LKKLQ-STTVM | 4501-4520 | 301 |

F. High levels of IgG antibodies, but no difference between intact and MDA-modified peptides but at least twice as much antibodies in the plasma of individuals with atherosclerosis as compared to the plasma of normal subjects (n = 7)

| Peptide | Sequence | Apo B-100 Amino Acid | SEQ ID NO |
|---|---|---|---|
| P10 | ALLVP-PETEE-AKQVL-FLDTV | 131-150 | 10 |
| P45 | IEIGL-EGKGF-EPTLE-ALFGK | 661-680 | 45 |
| P111 | SGASM-KLTTN-GRFRE-HNAKF | 1651-1670 | 111 |
| P154 | NLIGD-FEVAE-KINAF-RAKVH | 2296-2315 | 154 |

TABLE 2-continued

| Peptide | Sequence | Apo B-100 Amino Acid | SEQ ID NO |
|---|---|---|---|
| P199 | GHSVL-TAKGM-ALFGE-GKAEF | 2971-2990 | 199 |
| P222 | FKSSV-ITLNT-NAELF-NQSDI | 3316-3335 | 222 |
| P240 | FPDLG-QEVAL-NANTK-NQKIR | 3586-3605 | 240 |
| G. No level of IgG or IgM antibodies (n = 1) | | | |
| P2 | ATRFK-HLRKY-TYNYE-AESSS | 16-35 | 2 |

Example 3

ApoB-100-Peptides Selection

Inhibition of atherosclerosis in apo E −/− mice by immunization with fifteen different test articles based on fifteen different peptide fragments of apo B was investigated.

TABLE 3A

| Peptide | Sequence | Apo B-100 Amino Acid | SEQ ID NO |
|---|---|---|---|
| P2 | ATRFK-HLRKY-TYNYE-AESSS | 16-35 | 2 |
| P11 | FLDTV-YGNCS-THFTV-KTRKG | 151-170 | 11 |
| P25 | PQCST-HILQW-LKRVH-ANPLL | 361-380 | 25 |
| P32 | GNMGQ-TMEQL-TPELK-SSILK | 466-485 | 32 |
| P45 | IEIGL-EGKGF-EPTLE-ALFGK | 661-680 | 45 |
| P74 | VISIP-RLQAE-ARSEI-LAHWS | 1096-1115 | 74 |
| P102 | SLTST-SDLQS-GIIKN-TASLK | 1516-1535 | 102 |
| P129 | GSTSH-HLVSR-KSISA-ALEHK | 1921-1940 | 129 |
| P143 | IALDD-AKINF-NEKLS-QLQTY | 2131-2150 | 143 |
| P148 | IENID-FNKSG-SSTAS-MIQNV | 2206-2225 | 148 |
| P154 | NLIGD-FEVAE-KINAF-RAKVH | 2296-2315 | 154 |
| P162 | IREVT-QRLNG-EIQAL-ELPQK | 2416-2435 | 162 |
| P210 | KTTKQ-SFDLS-VKAQY-KKNKH | 3136-3155 | 210 |
| P219 | ILPSL-ELPVL-HVPRN-LKLSL | 3271-3290 | 219 |
| P240 | FPDLG-QEVAL-NANTK-NQKIR | 3586-3605 | 240 |

In these experiments, apo E −/− mice received primary subcutaneous immunization at 6-7 weeks of age, followed by two boosters administered 3 and 5 weeks later. The mice were fed a high cholesterol diet from 1 week after the second injection (10 weeks of age) and continued until sacrifice at 25 weeks of age. The effect of immunization on atherosclerosis formation was assessed by measuring plaque size (percent area stained with Oil Red O) in an en face preparation of the aorta.

Based on the results from these and other experiments, four peptides were identified as particularly effective in reducing the progression of atherosclerosis.

TABLE 3B

| Peptide | Reduction in atherosclerosis progression |
|---|---|
| P2 | (−42%, $p < 0.05$) |
| P45 | (−53%, $p < 0.05$) |
| P102 | (−52%, $p < 0.05$) |
| P210 | (−49%, $p = 0.06$) |

Example 4

Cholera Toxin B Subunit Gene Fusions for Immunization

The gene fusions used in the present disclosure were constructed using a CTB expression vector essentially as described previously (Sadeghi H, Bregenholt S, Wegmann D, Petersen J S, Holmgren J, and Lebens M. Genetic fusion of human insulin B-chain to the B-subunit of cholera toxin enhances in vitro antigen presentation and induction of bystander suppression in vivo. *Immunology*. 2002; 106:237-245). Synthetic oligonucleotides from Innovagen (Lund, Sweden) were used to make double stranded DNA fragments encoding the peptide sequence of interest that could be inserted into the vector such that the added peptide formed a carboxyl extension of mature CTB. The unmodified peptide p210 corresponding to amino acids 3136-3155 of human apoB-100 (KTTKQSFDLSVKAQYKKKNKH-SEQ ID NO:210) was encoded by the DNA sequence:

(SEQ ID NO: 303)
5'CAAAACGACCAAGCAAAGCTTTGATCTGAGCGTGAAAGCGCAGTATAA

GAAAAACAAACACTA3'

(SEQ ID NO: 304)
3'CATGGTTTTGCTGGTTCGTTTCGAAACTAGACTCGCACTTTCGCGTCA

TATTCTTTTTGTTTGTGATTCGA5'

(SEQ ID NO: 210)
K T T K Q S F D L S V K A Q Y K K N K H ***

This sequence is 90.9% identical to amino acids 3157-3185 of the murine apoB100 sequence, the exception being the insertion of a Serine (S) and an Asp (D) residue between N and KH in the C-terminal portion of the peptide:

Human     KTTKQSFDLSVKAQYKKN--KH (SEQ ID NO: 210)

Murine     KTTKQSFDLSVKAQYKKNSDKH (SEQ ID NO: 305)

Oligonucleotides were synthesized that encoded the p210 peptide corresponding to amino acids 3136-3155 of human apoB-100. The coding regions are flanked by sticky ends compatible with restriction enzymes KpnI and HindIII. Insertion into the expression vector leads to an in-frame extension to the carboxyl terminus of mature CTB.

The synthetic sequence was optimized for expression in *E. coli*. The single strands were annealed and ligated into the pML-CTB vector digested with KpnI and HindIII. Ligated DNA was used to transform *E. coli* B strain BL21. Transformants were selected initially on the basis of ampicillin resistance and plasmids were then screened using restriction analysis. Finally the sequence of the insert in selected clones was confirmed by DNA sequencing. Protein expression was induced by addition of IPTG to the growth medium. This resulted in the production of insoluble inclusion bodies containing the recombinant protein. The cells were disrupted by sonication following treatment with lysozyme and DNase. The inclusion bodies could be separated from the soluble cell protein and other insoluble cell debris by low speed centrifugation. LPS was removed by washing the inclusion bodies in three times in 0.1% triton X114 in PBS at 4° C. and subsequent extensive washing in PBS in order to remove the detergent. The inclusion bodies were dissolved in 6.5 M urea and reassembled into the biologically active pentameric form by removal of the urea by dialysis against 50 mM sodium carbonate buffer pH 9.0. The assembly and purity of the protein was assessed by SDS-PAGE. Receptor binding activity was confirmed by GM1 ELISA (Svennerholm A M, Holmgren J. Identification of *Escherichia coli* heat-labile enterotoxin by means of a ganglioside immunosorbent assay (GM1-ELISA) procedure. *Curr Microbiol.* 1978; 1:19-23). The protein was further partially purified by FPLC gel filtration using a sephadex 200 16/60 column. The OVA-CTB protein used as a control; also a fusion to the carboxyl terminus of mature CTB, was constructed and purified as previously described (George-Chandy A, Eriksson K, Lebens M, Nordström I, Schön E, Holmgren J. Cholera toxin B subunit as a carrier molecule promotes antigen presentation and increases CD40 and CD86 expression on antigen presenting cells. *Infect Immun.* 2001; 69:5716-5725).

Example 5

Mice and Immunization Protocols

Female apoe$^{-/-}$ mice were obtained from Taconic Europe (Ry, Denmark) and Apoe$^{-/-}$ CD4dnTGFβRIItg mice were previously generated in our laboratory (ref. 19). Starting at 8 weeks of age, mice were immunized intranasally twice per week for 12 weeks with either p210-CTB or OVA-CTB, both at 15 μg/dose (15 μl volume), or left untreated (PBS). Mice were fed a normal laboratory diet and sacrificed by $CO_2$ asphyxiation. All experiments were approved by the regional board for animal ethics.

Example 6

Tissue Processing and Immunohistochemistry

Lesion area per cross-section and fractional area of the lesion in the aortic root were quantified and the results expressed as the mean of 5 sections per mouse (ref. 22). In brief, fractional lesion area is calculated for each section as F %= (100×L/A) where L is lesion area (μm$^2$) and A is area inside external elastic lamina (μm$^2$). F % is averaged over all levels analyzed (200-600 μm$^2$ above aortic cusps) and the mean calculated for each treatment group. This method eliminates artifacts caused by oblique sections.

Primary antibodies (CD4, CD68, VCAM-1, I-A$^b$; all rat anti-mouse from BD Biosciences (Franklin Lakes, N.J., U.S.A.) and FoxP3 by eBioscience (San Diego, Calif., U.S.A.) titrated to optimum performance on spleen sections were applied to acetone-fixed cryosections from the aortic root, followed by detection with the ABC alkaline phosphatase kit from Vector Laboratories (Burlingame, Calif., USA). A thresholding technique was implemented using computerized ImagePro analysis (Media Cybernetics, Bethesda, Md., U.S.A.) of immunostained sections. For RNA isolation the thoracic aortic arch distal of the aortic root was dissected and snap-frozen.

Example 7

Flow Cytometry and Intracellular Cytokine Staining

Flow cytometry was performed on a CyAn™ (Dako, Glostrup, Denmark) after staining with the appropriate antibodies; data were analyzed using Summit v4.3 software (Dako). Primary labeled antibodies used were from BD Biosciences (anti-CD4) or from eBioscience (anti-FoxP3). To characterize the cytokine expression profiles of CD4$^+$ T cells from lung and spleen of nasally vaccinated mice, cell suspensions were prepared as described before and evaluated by intracellular cytokine staining and FACS analysis. Briefly, lung mononuclear cells were isolated by collagenase Type I digestion (324 U/ml; Sigma) for 1 h on a shaker and splenocytes were prepared by mechanical disruption followed by incubation in erythrocyte lysis buffer (Qiagen, USA) and extensively washed. CD4$^+$ T cells were purified using MACS magnetic cell separation as described above. 2×10$^5$ spleen or lung cells previously stimulated with 10 ug/ml of human apoB-100 for 24 hours, were restimulated for 4 h at 37° C. in 7.5% $CO_2$ with PMA (phorbol 12-myristate 13-acetate; 50 ng/ml), ionomycin (1 ug/ml; Sigma) and GolgiPlug (1 ul per 1 ml; BD Bioscience).

Alternatively, 2×10$^5$ CD4$^+$ T cells previously stimulated with plate bound anti-CD3 (5 ug/ml) and anti-CD28 (2 ug/ml) for 3 days in culture together with recombinant mouse IL-2 (10 ng/ml; Peprotech) and IL-4 (1 ng/ml; Peprotech) followed by a 3 day incubation with only IL-2 and IL-4, were restimulated with plate bound anti-CD3 (5 ug/ml) and anti-CD28 (2 ug/ml) for 5 h in the presence of GolgiPlug. All cells were incubated with FcγR block (BD Bioscience) followed by surface (anti-CD4) and intracellular staining of IFNγ, IL-4, IL-17 or IL-10 (BD Bioscience) and FoxP3 (eBioscience) according to the manufacturer's instructions. Cells were analyzed on a CyAn™ flow cytometer (Dako).

Example 8

Functional Immunoassays

A first group of apoe$^{-/-}$ mice were immunized subcutaneously with HPLC-purified human apoB-100 in complete Freund's adjuvant (CFA) from Pierce (Rockford, Ill., U.S.A.) and boosted 4 weeks later with apoB-100 in incomplete Freund's adjuvant (IFA) from Pierce to generate spleen T cells sensitized to human apoB-100, which were harvested one week later. A second group of mice received the nasal vaccine over 2 weeks (4 doses total/mouse) and CD4$^+$ T cells were harvested from the spleen 3 days after the last nasal administration of the vaccine. Spleen CD4$^+$ T cells (>95% purity) were isolated by negative selection over a magnetic column using MACS microbeads (CD4+ negative selection kit, Miltenyi Biotec GmbH, Bergisch Gladbach, Germany) according to the manufacturer's protocol. Splenocytes from apoB100-vaccinated apoe$^{-/-}$ mice were cocultured at varying dilution ratios with purified CD4$^+$ T cells from spleens of mice that had received nasal p210-CTB, OVA-CTB or PBS. To exclude contaminating apoB-100 in cell culture media, FCS-free IMDM from Gibco (Invitrogen, Carlsbad, Calif., U.S.A.) was supplemented with ITS™ from BD Biosciences. Cells were incubated for 72 hours in the absence or presence of purified human apoB-100 (20 μg/mL) with incorporation of $^3$H-thymidine during the last 18 hours. Data are presented as stimulation index (ratio of apoB-100-challenged to unchallenged coculture assay). In a second approach splenocytes and purified CD4$^+$ T cells were separated in transwell plates from Corning (Corning, N.Y., U.S.A.) to analyze whether cell-cell contact inhibition abrogated the suppressive effect of tolerized CD4+ T cells.

Example 9

Antibody Assays

ELISA methods were used to quantitate serum Ig isotypes specific for the apoB-100 peptide as well as total IgG and IgM as previously described (ref. 19). Sera from immunized mice were tested for antibodies to mouse LDL by incubation (1/50, 1/150 and 1/450 dilutions) in plates coated with mouse LDL (10 μg/ml) and using alkaline phosphatase-conjugated anti-mouse-IgG as detector antibody. Sera from C57BL/6 mice immunized with OVA-CTB were assayed for reactivity to mouse or human LDL, or to apoB100, at dilutions of 1/25, 1/250 and 1/2500.

Example 10

Real-Time Polymerase Chain Reaction

RNA was isolated from the aortic arch using the RNeasy kit from Qiagen (Hilden, Germany). Total RNA was analyzed by BioAnalyzer from Agilent Technologies (Waldbronn, Germany). Reverse transcription was performed with Superscript-II and random hexamers (both from Invitrogen) and cDNA amplified by real-time PCR using primers and probes for FoxP3, IL-10, TGF-β, IFN-γ and hypoxanthine guanidine ribonucleosyltransferase (HPRT) in an ABI 7700 Sequence Detector from Applied Biosystems. All primers and probes were obtained as "assays on demand" from Applied Biosystems (Foster City, Calif., U.S.A.) Data were analyzed on the basis of the relative expression method with the formula $2^{-\Delta\Delta C_T}$, where $\Delta\Delta C_T = \Delta C_T$ (sample)$-\Delta C_T$ (calibrator=average $C_T$ values of all samples within each group), and $\Delta C_T$ is the $C_T$ of the housekeeping gene (HPRT) subtracted from the $C_T$ of the target gene.

Example 11

Serum Analyses

Total serum triglycerides were determined with an enzymatic assay from Roche Diagnostics (Mannheim, Germany) using a TECAN InfiniTE M200 plate reader (TECAN Nordic, Täby Sweden). Total serum cholesterol and lipoprotein profiles were determined by FPLC separation of 2 μL serum of all individuals using a micro-FPLC column from GE Healthcare coupled to a system for online separation and subsequent detection of cholesterol as described, using human serum as reference (Parini P et al., Lipoprotein profiles in plasma and interstitial fluid analyzed with an automated gel-filtration system. Eur J Clin Invest 2006; 36:98-104). IL-10 ELISA from Mabtech (Nacka Strand, Sweden) and TGF-β ELISA from R&D Systems (Minneapolis, Minn., U.S.A.) was used to measure cytokine levels in supernatants.

Example 12

Statistical Analysis

Values are expressed as mean±standard error of the mean (SEM) unless otherwise indicated., Non-parametric Kruskal-Wallis test was used for multiple comparisons, Mann-Whitney U test was used for pairwise comparisons. A p-value of <0.05 was considered significant.

Example 13

Nasal Administration of p210-CTB Inhibits Atherosclerosis

Figure 6:
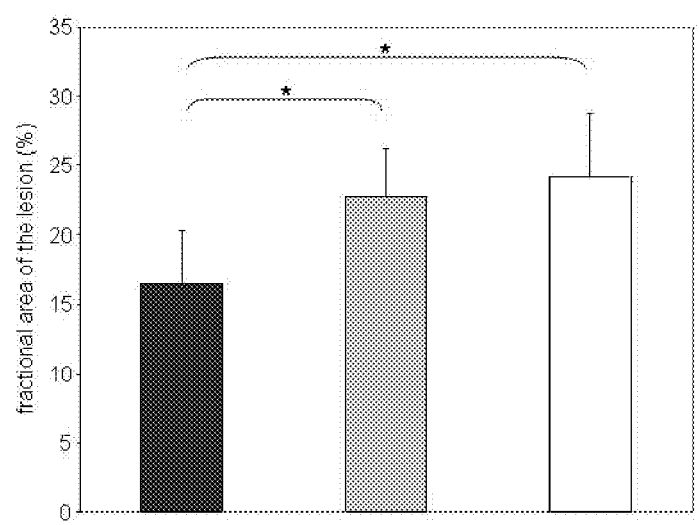
FIG. 6 shows data concerning lesion size in immunized mice. Fractional area of lesions in aortic root of apoe$^{-/-}$ mice treated nasally with p210-CTB (black bar), OVA-CTB (grey bar) and untreated controls (white bar). Mean±SD values are shown. * indicates p<0.05.

Nasal immunization with p210-CTB caused a significant 35% reduction in atherosclerotic lesion size (p=0.015; p=0.039) and fractional lesion area (p=0.012; p=0.007) in the aortic root as compared with OVA-CTB or untreated controls, respectively (FIG. 1A,B and FIG. 6). Atherosclerosis was not attenuated by administration of OVA-CTB compared with untreated controls indicating an apoB-100 peptide-specific effect (FIG. 1). The composition of the lesions was not significantly altered by p210-CTB immunization, as indicated by quantitative immunohistochemical analysis of markers for CD4$^+$ T cells, macrophages (CD68), or the inducible surface proteins I-A$^b$ (major histocompatibility complex class II protein) and the vascular cell adhesion molecule-1 (Table 5).

TABLE 4

Weight, cholesterol and triglyceride levels in plasma

| group | | weight (g) | cholesterol (mg/dL) | triglycerides (mg/dL) |
|---|---|---|---|---|
| apoe$^{-/-}$ | p210-CTB | 21 ± 1.3 | 281 ± 102 | 46 ± 9.1 |
| | OVA-CTB | 21.5 ± 0.6 | 257 ± 51 | 36 ± 3.9 |
| | control | 20.5 ± 1.0 | 313 ± 59 | 52 ± 7.9 |
| apoe$^{-/-}$x CD4dn TbRIItg | p210-CTB | 19.1 ± 2.9 | 254 + 84 | 40 ± 8.3 |
| | OVA-CTB | 20.8 ± 1.2 | 250 ± 94 | 40 ± 6.2 |
| | p value | n.s. | n.s. | n.s. |

Mean values and standard deviations are shown. Non-parametric group comparisons were performed using the Kruskal-Wallis test.

Example 14

Nasal Administration of p210-CTB does not Affect Plasma Lipids

Figure 7:
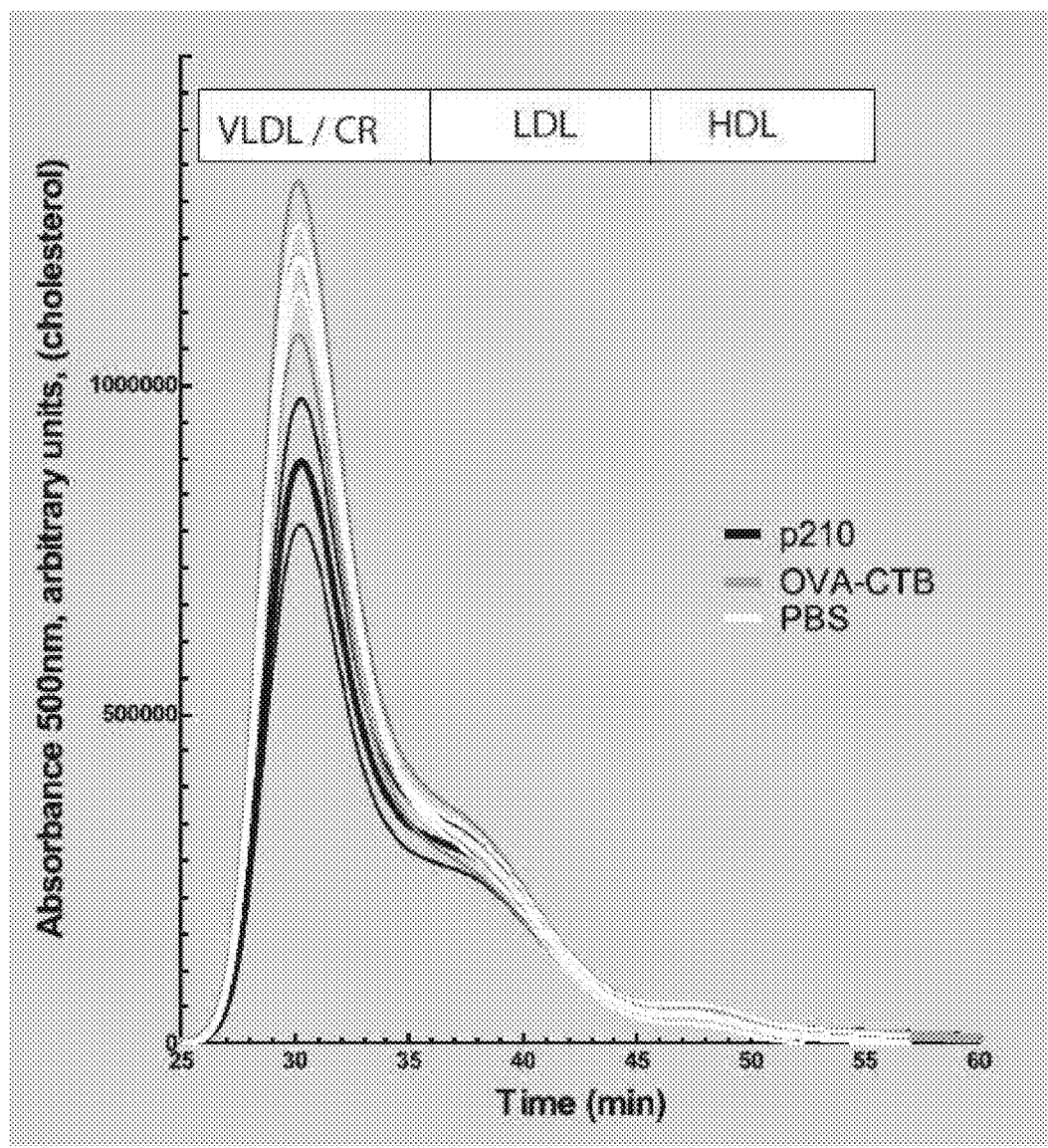
FIG. 7 shows data concerning plasma lipoprotein profiles analyzed by FPLC. Thick lines represent immunized groups: black=p210-CTB, grey=OVA-CTB and white shows the control group. Thin lines represent SEM. CR/VLDL=chylomicrons/very low density lipoproteins; LDL=low density lipoproteins; HDL=high density lipoproteins.

Immunization did not significantly affect body weight, serum cholesterol or triglycerides (Table 4). Plasma lipoprotein profiles were similar in mice immunized with p210-CTB or OVA-CTB, respectively (FIG. 7).

TABLE 5

Cellular composition and inflammatory markers in
aortas of 20 weeks old apoe$^{-/-}$ mice

|  | P210-CTB (A) | OVA-CTB (B) | control | p value |
|---|---|---|---|---|
| CD4 (cells/mm$^2$) | 176 ± 31 | 151 ± 35 | 124 ± 21 | n.s. |
| I-A$^b$ (cells/mm$^2$) | 87 ± 25 | 62 ± 17 | 112 ± 34 | n.s. |
| CD68 (% lesion) | 15.9 ± 3.6 | 22.6 ± 7.4 | 12.6 ± 2.3 | n.s. |
| VCAM-1 (% lesion) | 12.7 ± 4.6 | 22.3 ± 11.3 | 10.9 ± 1.0 | n.s. |
| FoxP3 (cells/mm$^2$) | 4.1 ± 0.8 | 4.2 ± 1.0 | 6.5 ± 2.6 | n.s. |

Positive cells are calculated per mm$^2$ lesion area except for FoxP3 cells, which are presented as cells per total vessel surface area as they were also found in the adventitia. Statistics were performed using the non-parametric Kruskall Wallis test.

Example 15

CTB Fusion Protein Immunization Increases Aortic FoxP3 and IL-10 mRNA Levels

Figure 8:
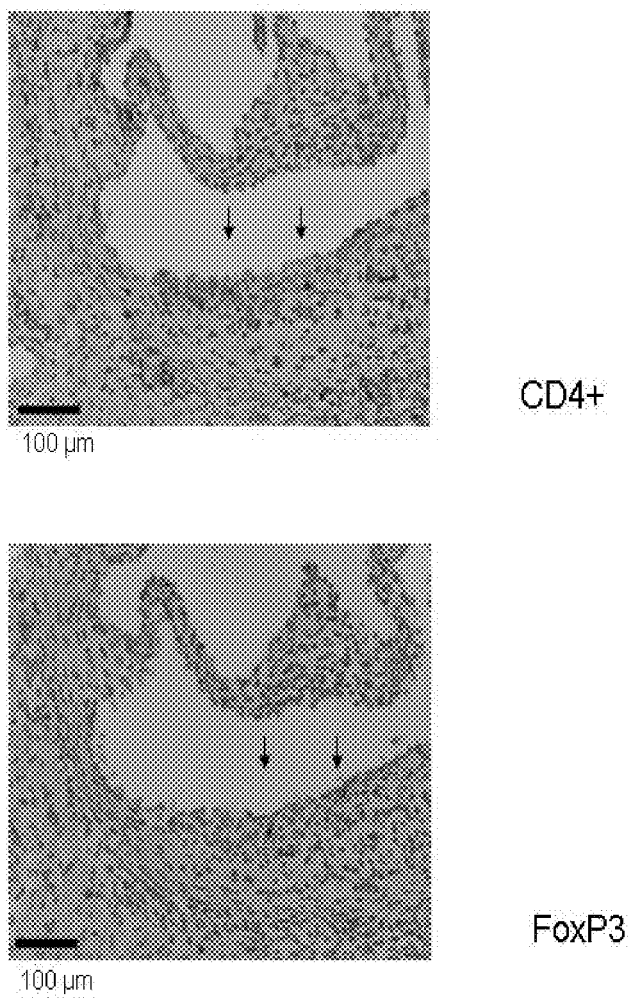
FIG. 8 shows data concerning T cells in lesions in immunized mice, and in particular representative immunohistochemical stains of atherosclerotic lesion in the aortic root of apoe$^{-/-}$ mice. Arrows indicate FoxP3+ cells; they were CD4+ in directly adjacent sections.

Real-time reverse transcription-PCR analysis of the thoracic aorta of apoe$^{-/-}$ mice showed significant increases in FoxP3 and IL-10 mRNA levels in both CTB vaccine groups (p210-CTB and OVA-CTB) (FIG. 1C). No statistically relevant differences in FoxP3 or IL-10 mRNA were detected when comparing mice that had received p210-CTB or OVA-CTB, respectively. Furthermore, FoxP3$^+$ cell numbers did not differ between groups; a representative example of FoxP3$^+$ cells in aortic lesions is shown in FIG. 8. IL-10 was elevated to the same extent in p210-CTB and OVA-CTB groups, pointing to a possible adjuvant effect of CTB. Trends towards increased TGF-β and decreased IFN-γ mRNA in vaccinated mice were not significant.

Example 16

Figure 2:
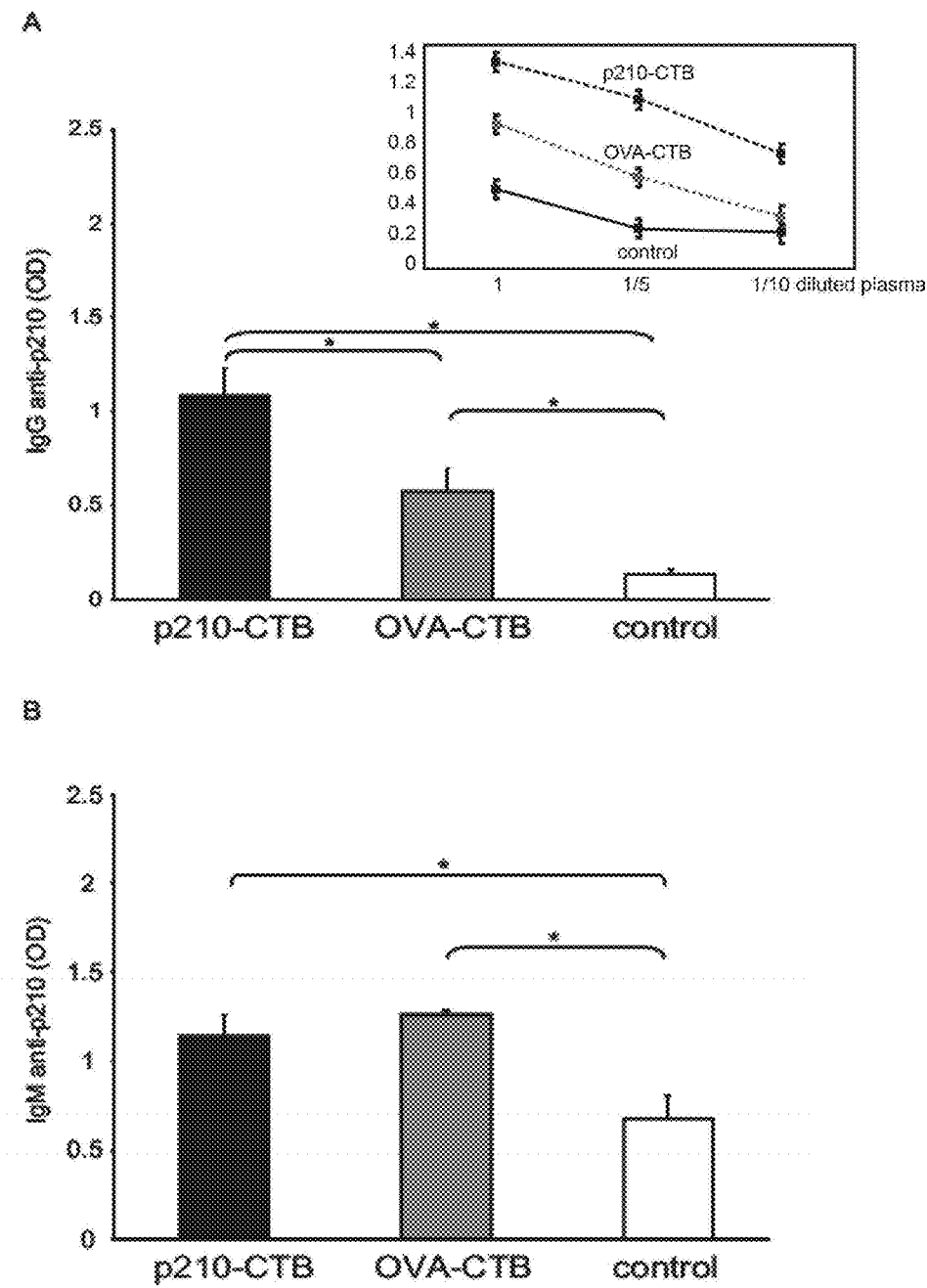
FIG. 2 shows data concerning nasal immunization induced a systemic humoral immune response in apoe$^{-/-}$ mice. (A) IgG-anti-p210 titers in mouse plasma; titration curves are shown in the inset. (B) p210-specific IgM titers in plasma from the same mice. * indicates p<0.05.
Figure 9:
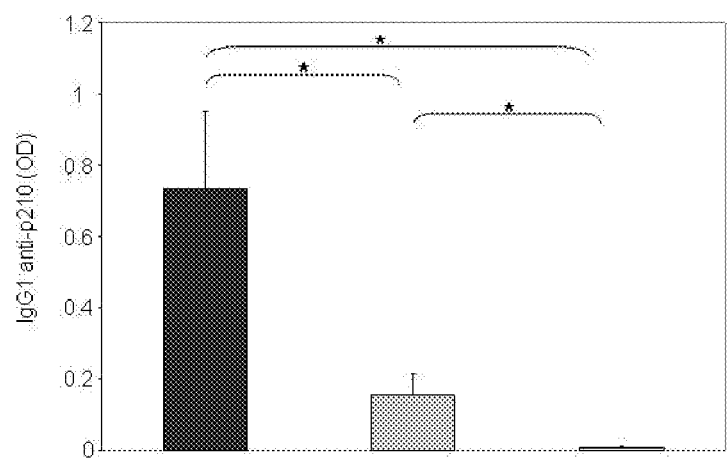
FIG. 9 shows data concerning serum IgG1 antibody titers to apoB-100 peptide. ELISA analysis of sera from apoe$^{-/-}$ mice treated with p210-CTB (black bar), OVA-CTB (grey bar) or controls (white bar). * indicates p<0.05.
Figure 10:
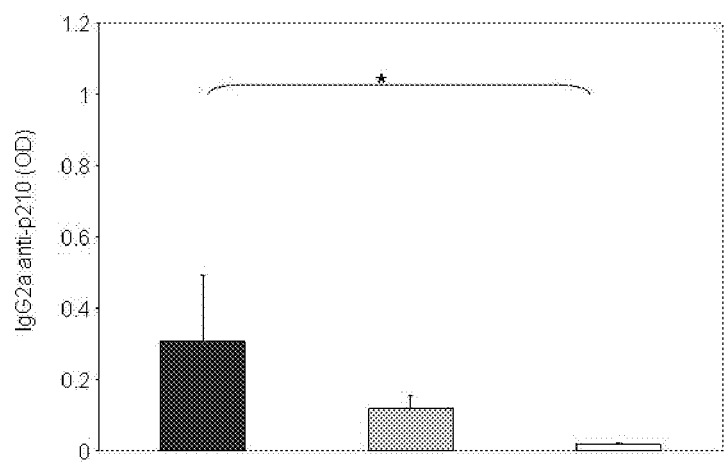
FIG. 10 shows data concerning serum IgG2a antibody titers to apoB-100 peptide. Apoe$^{-/-}$ mice treated with p210-CTB (black bar), OVA-CTB (grey bar) or controls (white bar). * indicates p<0.05.
Figure 11:
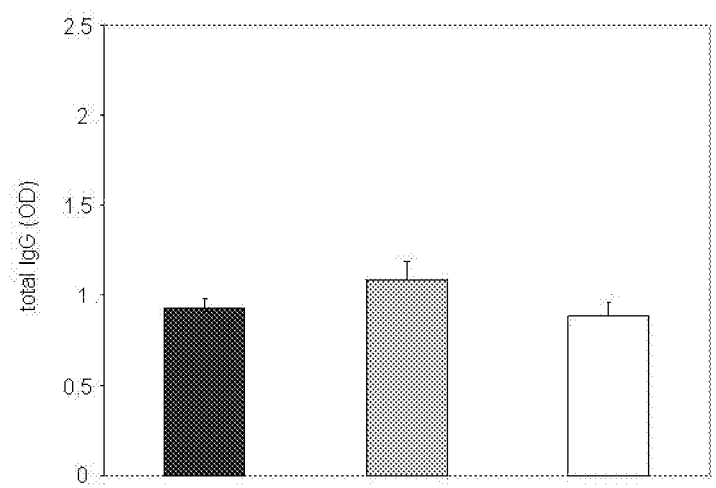
FIG. 11 shows data concerning total IgG in sera of immunized mice. Apoe$^{-/-}$ mice treated with p210-CTB (black bar), OVA-CTB (grey bar) or controls (white bar).
Figure 12:
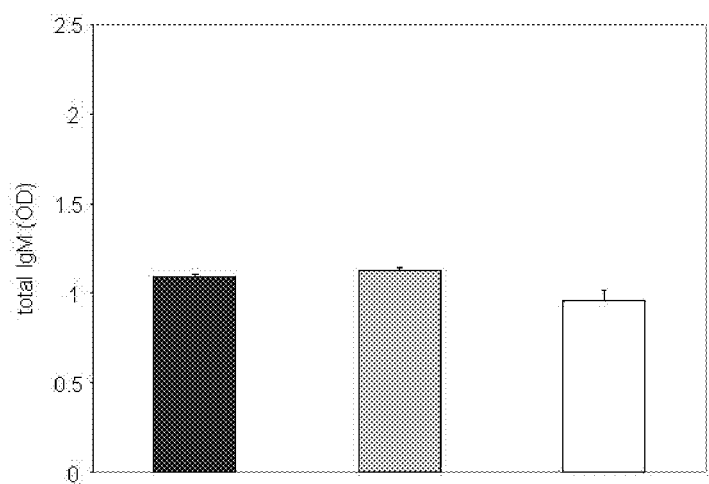
FIG. 12 shows data concerning total IgM in sera of immunized mice. Apoe$^{-/-}$ mice treated with p210-CTB (black bar), OVA-CTB (grey bar) or controls (white bar).

Nasal Vaccination Induces Mucosal and Systemic Humoral and Cellular Immune Responses P210-CTB immunization induced significantly elevated titers of IgG antibodies to the p210 peptide of apoB-100 (FIG. 2A). Modestly increased IgG anti-p210 was observed in OVA-CTB immunized apoe$^{-/-}$ mice. The IgG1/IgG2a ratio of anti-p210 antibodies did not change, implying that there was no Th1/Th2 shift in T helper activity to B cell activation (FIG. 9 and FIG. 10). Total IgG levels were not influenced by either treatment (FIG. 11). p210-specific IgM titers were significantly elevated both in p210-CTB and OVA-CTB treated groups; however, no difference was detected between p210-CTB and OVA-CTB treated animals (FIG. 2B). Total IgM was not influenced by either treatment (FIG. 12). Sera of immunized mice were tested for antibodies to mouse LDL particles, however, ELISA did not show any such titers (data not shown). Therefore, antibodies induced to human p210 did not recognize intact, endogenous LDL particles in the immunized mice. Apoe$^{-/-}$ mice immunized with OVA-CTB showed modestly increased titers to p210 (FIG. 2). However, parenteral immunization with OVA did not lead to induction of significant IgG antibody responses to mouse LDL (data not shown), thus ruling out serological crossreactivity between OVA and LDL protein.

Figure 3:
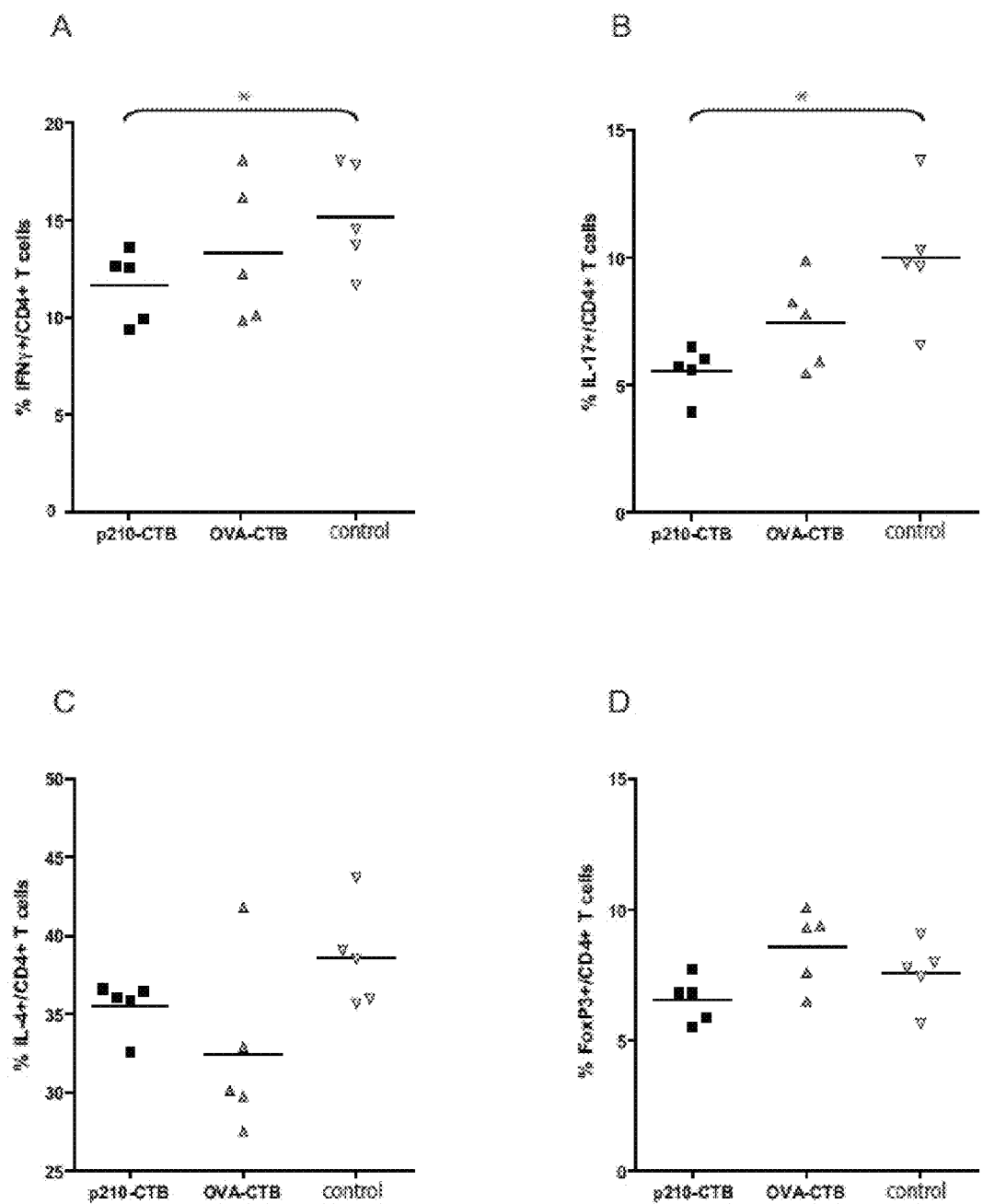
FIG. 3 shows data concerning nasal immunization altered T cell subset composition in lung mucosa. Flow cytometric analysis of intracellular subset markers, with cytokine-producing CD4$^+$ T cells as percentage of total CD4$^+$ T cells for each of the three groups. (A) Interferon-γ; (B) IL-17; (C) IL-4; (D) FoxP3. * indicates p<0.05.

Analysis of the cellular immune response in the lung, the major organ targeted after nasal vaccination, showed a significant decrease in CD4$^+$ T cells expressing interferon-γ (characteristic of Th1 cells) and IL-17 (characteristic of Th17 cells), respectively, in mice treated with p210-CTB (FIG. 3 A,B). In contrast, no such change was recorded for IL-4$^+$ CD4$^+$ T cells or for FoxP3$^+$ CD4$^+$ T cells (FIG. 3 C,D). This indicates a shift of the T helper cell balance in the respiratory mucosa, away from the proinflammatory Th1 and Th17 subtypes after nasal immunization with p210-CTB.

Figure 4:
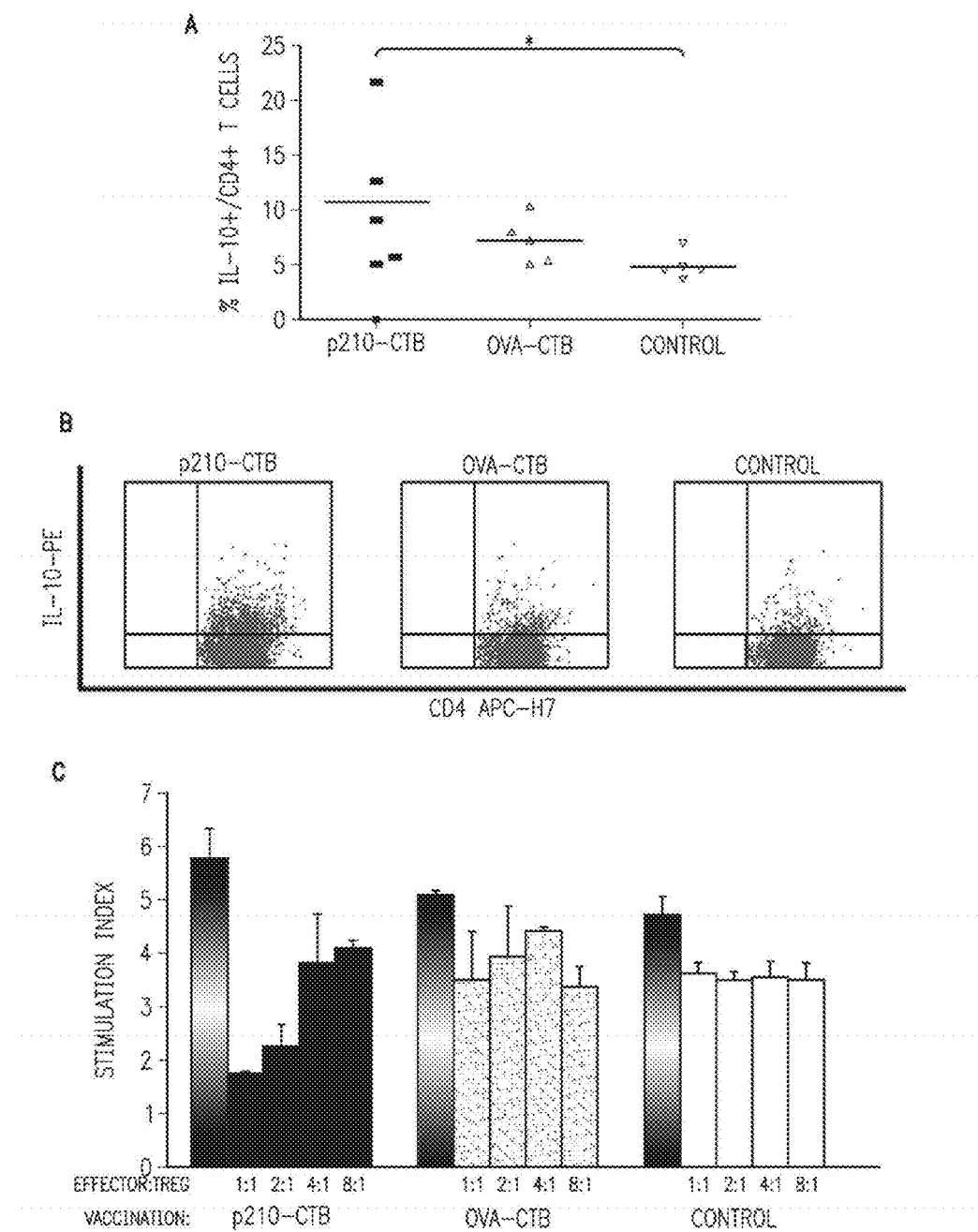
FIG. 4 shows data concerning nasal p210-CTB immunization induced IL-10-producing CD4$^+$ T cells and apoB-100-specific Treg activity in spleen. A) Flow cytometric analysis of cultured spleen cells stained for intracellular IL-10. (B) Representative flow cytometric plots. (C) Splenic effector cells at 2.5×10$^5$ cells/well were generated from apoe$^{-/-}$ mice that had been immunized with human apoB100. The stimulation index represents the ratio of $^3$H thymidine uptake upon stimulation with human apoB 100 (20 μg/mL) relative to unstimulated cells. Proliferation of effector cells alone is indicated in the leftmost bar of each group. Addition of purified CD4$^+$ T cells from nasally immunized animals is indicated at different ratios to effector cells. * p<0.05.
Figure 13:
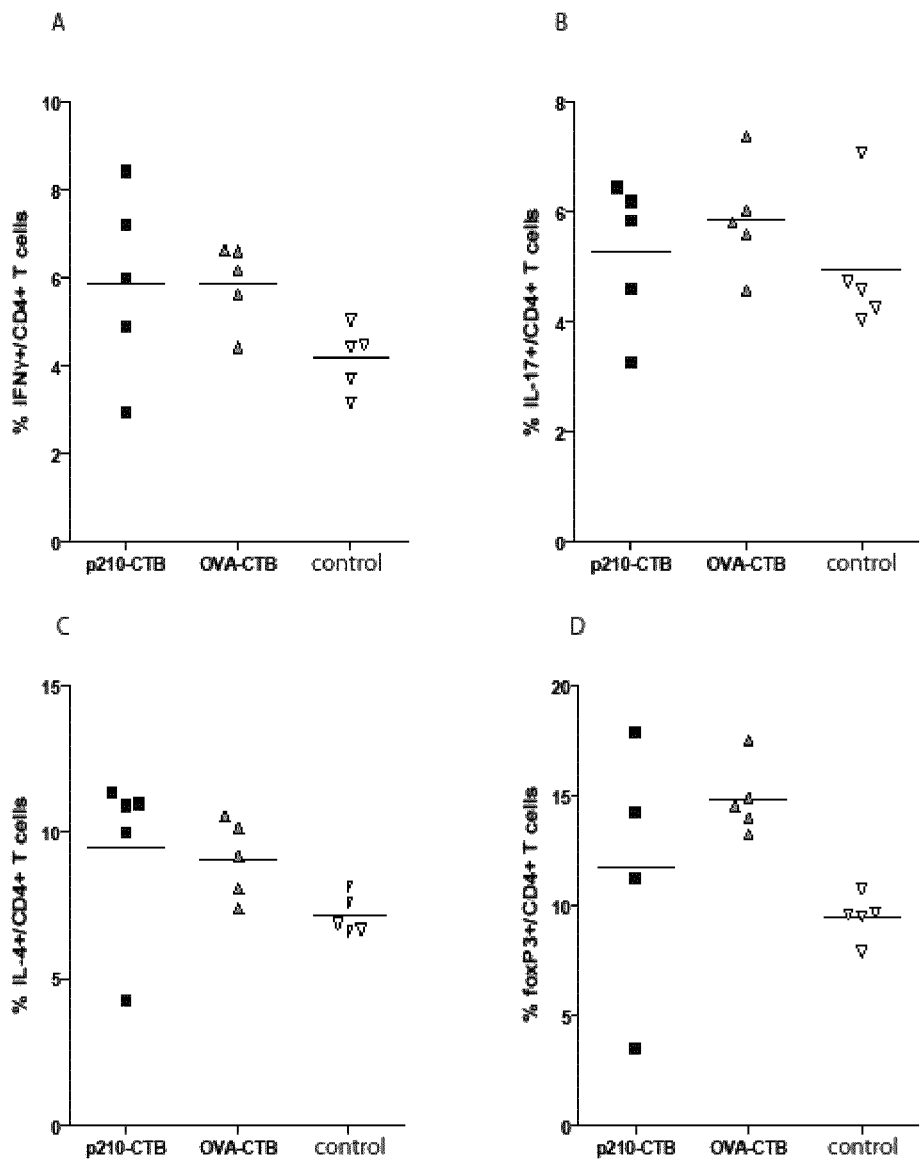
FIG. 13 shows data concerning T cell subsets in spleen after immunization. Flow cytometric analysis of intracellular cytokine expression is shown as percentage of cytokine-producing cells per CD4$^+$ T cells for each of the three groups. (A) Interferon-γ; (B) IL-17; (C) IL-4; (D) FoxP3.

Systemic cellular immune responses were monitored in spleen cell preparations. Nasal immunization with p210-CTB significantly increased the proportion of spleen CD4$^+$ T cells expressing the anti-inflammatory cytokine IL-10 (FIGS. 4 A and B). Unlike the situation in the lung, no significant differences were detected in the distribution of the remaining CD4$^+$ T cell subsets in the spleen, as characterized by intracellular staining for interferon-γ, IL-17, IL-4 and FoxP3 (FIG. 13).

Example 17

P210-CTB Treatment Induces ApoB100-Specific Treg Activity

Figure 14:
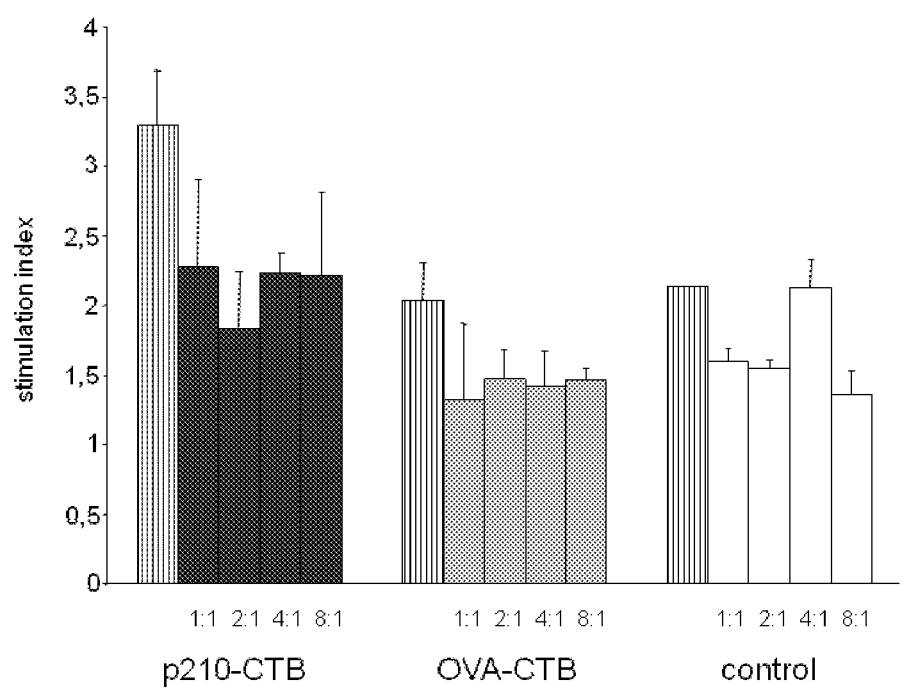
FIG. 14 shows data concerning abrogation of Treg suppressor effect upon separation of cells. Cocultures of effector cells and CD4$^+$ T cells from nasally immunized mice are indicated by plain bars (generated from black=p210-CTB, grey=OVA-CTB and white=control group animals). Abrogated effect of CD4+ T cell-mediated inhibition of proliferation when effector cells and CD4$^+$ T cells are cultured separate from each other in a transwell plate (contact inhibition assay).
Figure 15:
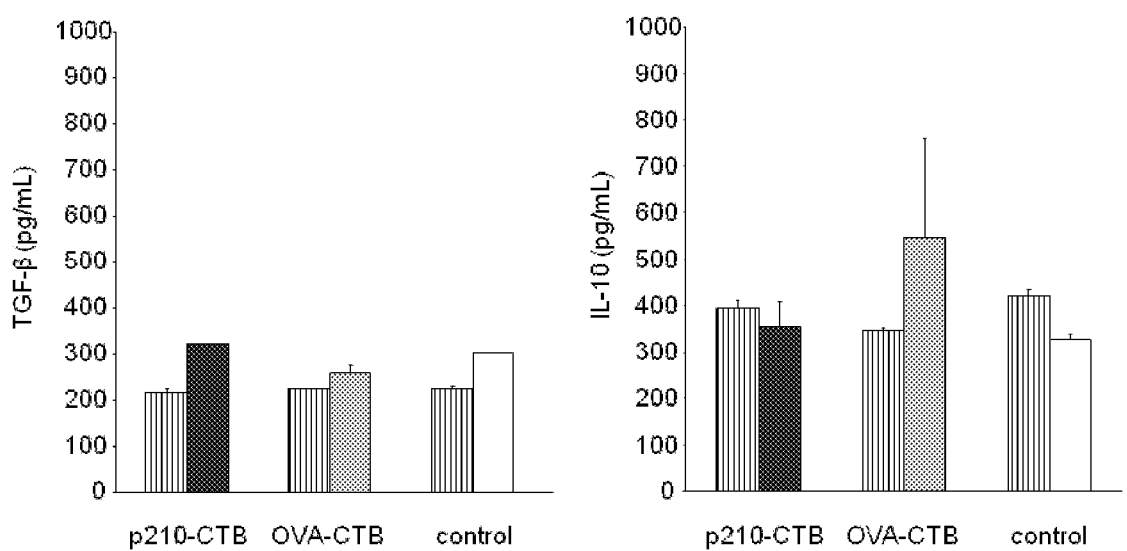
FIG. 15 shows data concerning cytokine levels for TGF-β and IL-10 in the supernatants from the coculture assay. Striped bars represent effector cells alone. Cocultures of effector cells and CD4$^+$ T cells from nasally immunized mice are indicated by plain bars (generated from black=p210-CTB, grey=OVA-CTB and white=control group animals).

To assess whether functional Treg were induced by immunization, we exposed spleen CD4$^+$ T cells from apoe$^{-/-}$ mice immunized subcutaneously with human apoB-100 (effector T cells), to CD4$^+$ T cells from mice immunized nasally with either p210-CTB, OVA-CTB, or no antigen (FIG. 4C). A marked dose-dependent inhibition of effector T cell proliferation was observed in the presence of CD4$^+$ T cells from p210-CTB immunized mice. No such inhibition was observed when T cells from OVA-CTB or non-immunized mice were added. The inhibitory effect of T cells from p210-CTB immunized mice was abolished when these cells were separated from effector T cells by a membrane, indicating that suppression required cell-cell contact (FIG. 14). Levels of IL-10 and TGF-β in culture supernatants did not differ between groups (FIG. 15).

Example 18

Figure 5:
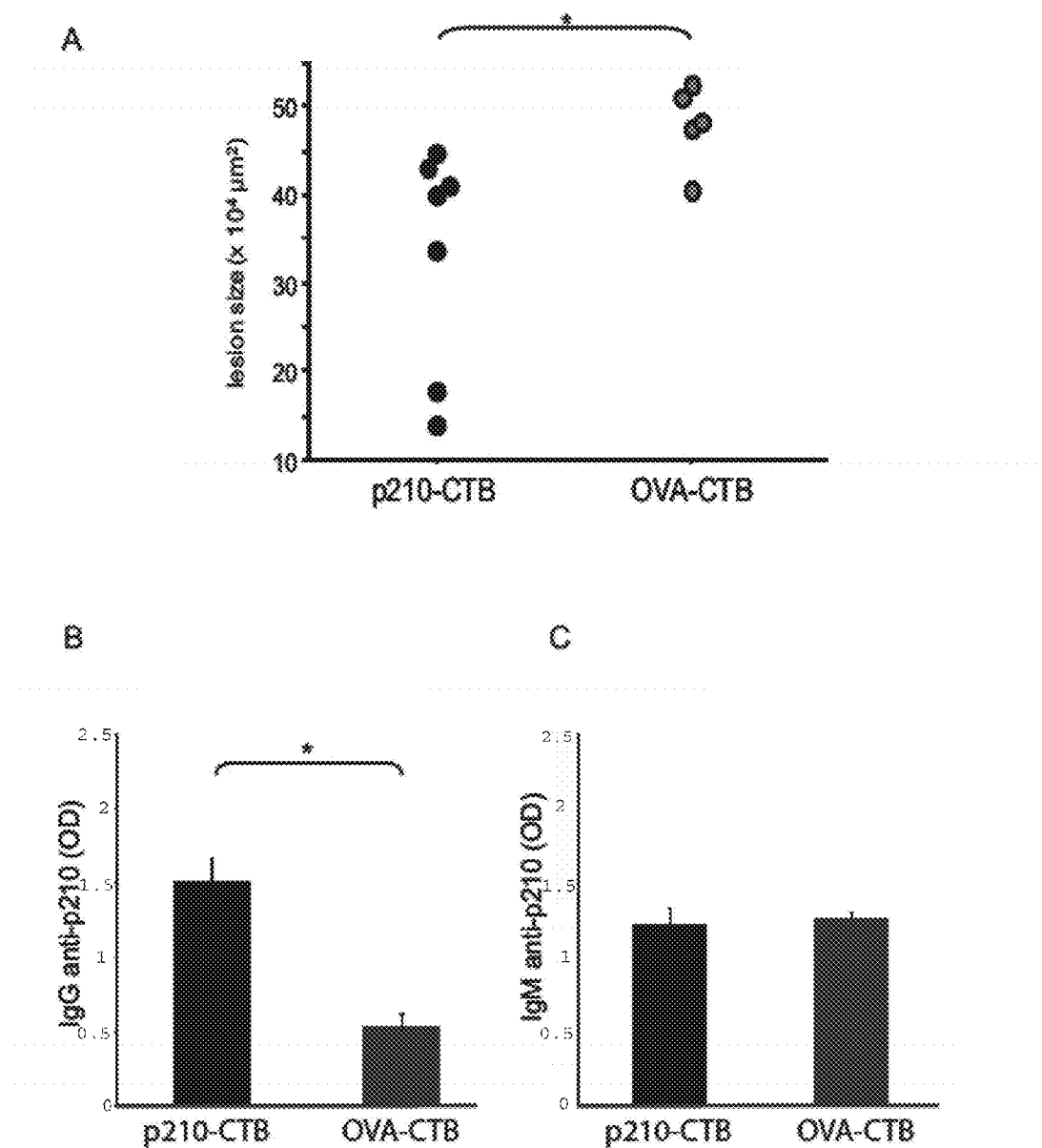
FIG. 5 shows data concerning a protective effect of nasal p210-CTB immunization on atherosclerotic lesion size does not depend on TGF-β signaling in T cells. A) Lesion size in the aortic root of apoe$^{-/-}$×CD4dnTGFβRIItg mice immunized with p210-CTB (black dots) or OVA-CTB (grey dots). Effect of immunization on p210-specific antibody titers of IgG class (B) and IgM (C). * p<0.05.
Figure 16:
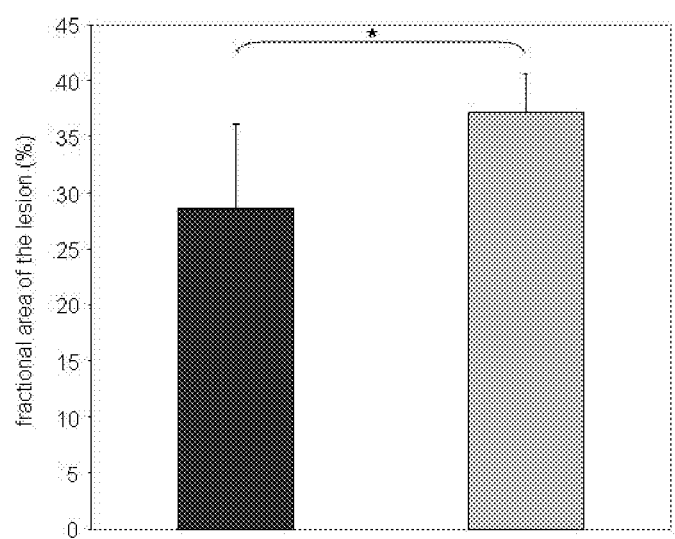
FIG. 16 shows data concerning lesion size in immunized mice with defective TGFβ receptors on T cells. Fractional area of the lesion in the aortic root of apoe$^{-/-}$×CD4dnTGFβRIItg mice treated nasally with p210-CTB (black bar) or OVA-CTB (grey bar). Mean±SD values are shown. * indicates p<0.05.
Figure 17:
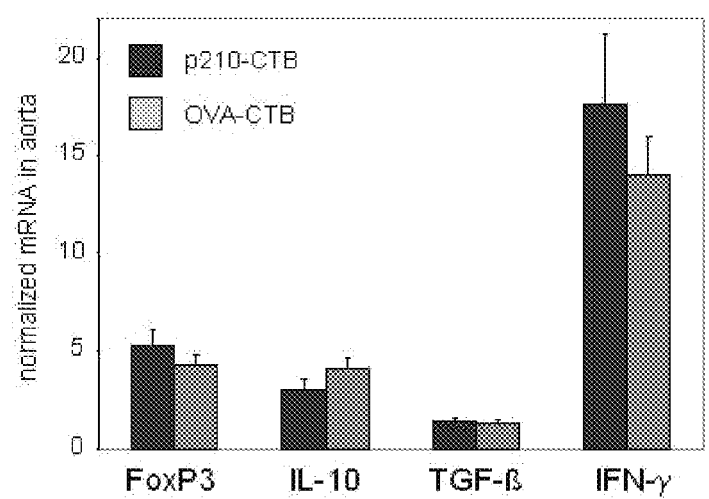
FIG. 17 shows data concerning mRNA levels in aorta of mice with defective TGFβ receptors on T cells. Real-time reverse-transcription PCR normalized to HPRT in thoracic aorta of apoe$^{-/-}$×CD4dnTGFβRIItg mice. Of note, the development of functional Foxp3$^+$ Treg cells depends on TGFβ. Therefore, detailed information concerning the relevance of FoxP3-expressing cells in apoe$^{-/-}$×CD4dnTGFβRIItg mice require further investigation.
Figure 18:
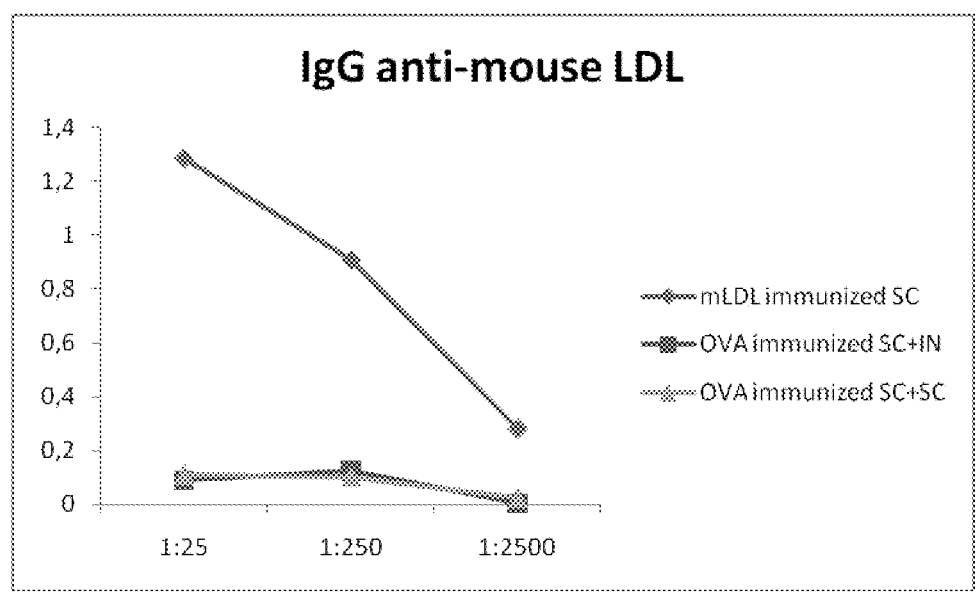
FIG. 18 shows data concerning IgG antibodies to mouse LDL in mice immunized with LDL or OVA. C57BL/6J mice were immunized with mouse LDL (mLDL) or ovalbumin (OVA). ELISA was performed with serum dilutions in wells coated with mouse LDL, followed by alkaline phosphatase-labeled anti-mouse-IgG. SC, subcutaneous administration, IN, intranasal administration.

The Atheroprotective Effect of Nasal p210-CTB Vaccination is Independent of TGF-β Signaling in T Cells To determine whether the atheroprotective effect of nasal vaccination with p210-CTB depended on TGF-β signaling in T cells, we immunized apoe$^{-/-}$ mice lacking functional TGF-β receptors on T cells (CD4dnTGFβRIIxapoe$^{-/-}$ mice). Nasal immunization with p210-CTB significantly reduced atherosclerotic lesion size by 30% in CD4dnTGFβRIIx apoe$^{-/-}$ mice, as compared with littermates immunized with OVA-CTB (FIG. 5A and FIG. 16). This indicates that TGFβR signaling in T cells is not required for the atheroprotective effect of nasal p210-CTB vaccination. It also argues against a decisive role for FoxP3+ Treg, as these cells are thought to require TGFβ for their function. IgG but not IgM antibodies directed against the apoB100-peptide were significantly elevated in all groups of mice immunized with p210-CTB, irrespective of whether signaling via TGF-β was blocked during immunization (FIG. 5B,C). Analysis of mRNA expression in aortas showed no differences in mRNA for, IL-10, TGF-β or interferon-γ between p210-CTB- and OVA-CTB-vaccinated mice (FIG. 17). Surprisingly, FoxP3 mRNA was not reduced in CD4dnTGFβRIIxapoe$^{-/-}$ mice, possibly reflecting the presence of immature Treg (FIG. 17). Furthermore, quantitative immunohistochemistry showed no differences in cellular composition of lesions between treatment groups (Table 6).

TABLE 6

Cellular composition and inflammatory markers in aortas of 20 weeks old apoe$^{-/-}$ CD4dnTGFβRIItg mice

| | p210-CTB (C) | OVA-CTB (D) | p value |
|---|---|---|---|
| CD4 (cells/mm$^2$) | 120 ± 43 | 173 ± 55 | n.s. |
| I-A$^b$ (cells/mm$^2$) | 94 ± 16 | 238 ± 102 | n.s. |
| CD68 (% lesion) | 9.9 ± 2.8 | 14.5 ± 2.6 | n.s. |
| VCAM-1 (% lesion) | 7.6 ± 2.6 | 19.3 ± 2.2 | n.s. |
| FoxP3 (cells/mm$^2$) | 19.7 ± 5.2 | 25.6 ± 3.4 | n.s. |

Positive cells are calculated per mm$^2$ lesion area except for FoxP3 cells, which are presented as cells per total vessel surface area as they were also found in the adventitia. Statistics were performed using the non-parametric Kruskall Wallis test.

In the above exemplary procedures, a peptide comprising amino acids 3136-3155 of apolipoprotein B-100 (p210) was fused to the B subunit of cholera toxin (CTB), which binds to a ganglioside on mucosal epithelia. The effect of nasal administration of the p210-CTB fusion protein on atherogenesis was compared with that of an ovalbumin peptide fused to CTB and with untreated controls. Immunization with p210-CTB for 12 weeks caused a 35% reduction in aortic lesion size of apoe$^{-/-}$ mice. This effect was accompanied by induction regulatory T cells that markedly suppressed effector T cells rechallenged with apoB-100 and increased numbers of IL-10$^+$ CD4$^+$ T cells. Furthermore, a peptide-specific antibody response was observed. Atheroprotection was also documented in apoe$^{-/-}$ mice lacking functional transforming growth factor-beta receptors on T cells.

The above results confirm and extend previous reports on atheroprotective effects of immunization with LDL or its components[5-8, 12, 15, 16]. The use of complete LDL particles as immunogens is not attractive for clinical vaccination strategies since these particles may contain multiple pro-inflammatory and even potentially toxic molecules such as modified lipids and endotoxins. Recent studies have identified a set of apoB-100-derived peptides with significant atheroprotective effects[15, 16], enabling development of a structurally defined vaccine candidate. Among them, specific native peptides were immunogenic in humans and mice and correlated with the extent of atherosclerotic disease (33-34). By combining a limited number of peptides in the vaccine, overcoming MHC restriction is expected. Combining peptide sequences with immunomodulatory components (adjuvants) such as CTB is an attractive approach to selectively induce protective immunity while avoiding side effects caused by non-peptide components in LDL particles. Unlike LDL, the vaccine formulation can be manufactured in a reproducible way and under Good Manufacturing Practice (GMP) conditions. The possibility to induce atheroprotective immunity by nasal administration of an LDL component is also attractive for clinical medicine.

In summary, the present disclosure provides fusion products and related compositions methods and systems that in several embodiments allow performing a strategy for atheroprotective immunization. A peptide sequence from apolipoprotein B-100 of low-density lipoprotein fused with a carrier such as the B subunit of cholera toxin is described and used for immunization of mices and in particular for intranasal immunization of Apoe$^{-/-}$ mice. Methods and systems herein described led to antigen-specific regulatory T cells and a 35% reduction of atherosclerosis.

The examples set forth above are provided to give those of ordinary skill in the art a complete disclosure and description of how to make and use the embodiments of the fusion proteins, compositions, systems and methods of the disclosure, and are not intended to limit the scope of what the inventors regard as their disclosure. Modifications of the above-described modes for carrying out the disclosure that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

The entire disclosure of each document cited (including patents, patent applications, journal articles, abstracts, laboratory manuals, books, or other disclosures) in the Background, Summary, Detailed Description, and Examples is hereby incorporated herein by reference.

Further, the hard copy of the sequence listing submitted herewith and the corresponding computer readable form are both incorporated herein by reference in their entireties.

It is to be understood that the disclosures are not limited to particular compositions or biological systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified can be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein can be excluded from a claim of this disclosure. The disclosure illustratively described herein suitably can be practiced in the absence of any element or elements, limitation or limitations which is not specifically disclosed herein.

A number of embodiments of the disclosure have been described. The specific embodiments provided herein are examples of useful embodiments of the disclosure and it will be apparent to one skilled in the art that the disclosure can be carried out using a large number of variations of the fusion proteins, fusion protein components, compositions, methods steps, and systems set forth in the present description. As will be obvious to one of skill in the art, methods and devices useful for the present methods can include a large number of optional composition and processing elements and steps.

In particular, it will be understood that various modifications may be made without departing from the spirit and scope of the present disclosure. Accordingly, other embodiments are within the scope of the following claims.

References

1. Baigent C, Keech A, Kearney P M, Blackwell L, Buck G, Pollicino C, et al. Efficacy and safety of cholesterol-lowering treatment: prospective meta-analysis of data from 90,056 participants in 14 randomised trials of statins. Lancet. 2005 Oct. 8; 366(9493):1267-78.
2. Tabas I, Williams K J, Boren J. Subendothelial lipoprotein retention as the initiating process in atherosclerosis: update and therapeutic implications. Circulation. 2007 Oct. 16; 116(16):1832-44.
3. Hansson G K. Inflammation, atherosclerosis, and coronary artery disease. N Engl J Med. 2005 Apr. 21; 352(16):1685-95.
4. Hansson G K, Libby P. The immune response in atherosclerosis: a double-edged sword. Nat Rev Immunol. 2006 July; 6(7):508-19.
5. Buono C, Binder O, Stavrakis G, Witztum J L, Glimcher L H, Lichtman A H. T-bet deficiency reduces atherosclerosis and alters plaque antigen-specific immune responses. Proceedings of the National Academy of Sciences of the United States of America. 2005 Jan. 21.
6. Gotsman I, Sharpe A H, Lichtman A H. T-cell costimulation and coinhibition in atherosclerosis. Circ Res. 2008 Nov. 21; 103(11):1220-31.
7. Palinski W, Miller E, Witztum J L. Immunization of low density lipoprotein (LDL) receptor-deficient rabbits with homologous malondialdehyde-modified LDL reduces atherogenesis. Proc Natl Acad Sci USA. 1995 Jan. 31; 92(3):821-5.
8. Ameli S, Hultgardh-Nilsson A, Regnstrom J, Calara F, Yano J, Cercek B, et al. Effect of immunization with homologous LDL and oxidized LDL on early atherosclerosis in hypercholesterolemic rabbits. Arterioscler Thromb Vasc Biol. 1996 August; 16(8):1074-9.
9. George J, Afek A, Gilburd B, Levkovitz H, Shaish A, Goldberg I, et al. Hyperimmunization of apo-E-deficient mice with homologous malondialdehyde low-density lipoprotein suppresses early atherogenesis. Atherosclerosis. 1998 May; 138(1):147-52.
10. Zhou X, Caligiuri G, Hamsten A, Lefvert A K, Hansson G K. LDL immunization induces T-cell-dependent antibody formation and protection against atherosclerosis. Arterioscler Thromb Vasc Biol. 2001 January; 21(1):108-14.
11. George J, Yacov N, Breitbart E, Bangio L, Shaish A, Gilburd B, et al. Suppression of early atherosclerosis in LDL-receptor deficient mice by oral tolerance with beta 2-glycoprotein I. Cardiovasc Res. 2004 Jun. 1; 62(3):603-9.
12. Maron R, Sukhova G, Faria A M, Hoffmann E, Mach F, Libby P, et al. Mucosal administration of heat shock protein-65 decreases atherosclerosis and inflammation in aortic arch of low-density lipoprotein receptor-deficient mice. Circulation. 2002 Sep. 24; 106(13):1708-15.
13. Harats D, Yacov N, Gilburd B, Shoenfeld Y, George J. Oral tolerance with heat shock protein 65 attenuates *Mycobacterium tuberculosis*-induced and high-fat-diet-driven atherosclerotic lesions. J Am Coll Cardiol. 2002 Oct. 2; 40(7):1333-8.
14. van Puijvelde G H, Hauer A D, de Vos P, van den Heuvel R, van Herwijnen M J, van der Zee R, et al. Induction of oral tolerance to oxidized low-density lipoprotein ameliorates atherosclerosis. Circulation. 2006 Oct. 31; 114(18):1968-76.
15. Shevach E M. From vanilla to 28 flavors: multiple varieties of T regulatory cells. Immunity. 2006 August; 25(2):195-201.
16. Sakaguchi S, Yamaguchi T, Nomura T, Ono M. Regulatoty T cells and immune tolerance. Cell. 2008 May 30; 133(5):775-87.
17. Fredrikson G N, Hedblad B, Berglund G, Alm R, Ares M, Cercek B, et al. Identification of immune responses against aldehyde-modified peptide sequences in apoB associated with cardiovascular disease. Arterioscler Thromb Vasc Biol. 2003 May 1; 23(5):872-8.
18. Fredrikson G N, Soderberg I, Lindholm M, Dimayuga P, Chyu K Y, Shah P K, et al. Inhibition of atherosclerosis in apoE-null mice by immunization with apoB-100 peptide sequences. Arterioscler Thromb Vasc Biol. 2003 May 1; 23(5):879-84.
19. Holmgren J, Czerkinsky C. Mucosal immunity and vaccines. Nature medicine. 2005 April; 11(4 Suppl):S45-53.
20. Kunisawa J, Nochi T, Kiyono H. Immunological commonalities and distinctions between airway and digestive immunity. Trends Immunol. 2008 November; 29(11):505-13.
21. Sun J B, Raghavan S, Sjoling A, Lundin S, Holmgren J. Oral tolerance induction with antigen conjugated to cholera toxin B subunit generates both Foxp3+CD25+ and Foxp3-CD25-CD4+ regulatory T cells. J Immunol. 2006 Dec. 1; 177(11):7634-44.
22. Stanford M, Whittall T, Bergmeier L A, Lindblad M, Lundin S, Shinnick T, et al. Oral tolerization with peptide 336-351 linked to cholera toxin B subunit in preventing relapses of uveitis in Behcet's disease. Clin Exp Immunol. 2004 July; 137(1):201-8.
23. Robertson A K, Rudling M, Zhou X, Gorelik L, Flavell R A, Hansson G K. Disruption of TGF-beta signaling in T cells accelerates atherosclerosis. J Clin Invest. 2003 November; 112(9):1342-50.
24. Nicoletti A, Kaveri S, Caligiuri G, Bariety J, Hansson G K. Immunoglobulin treatment reduces atherosclerosis in apo E knockout mice. J Clin Invest. 1998 Sep. 1; 102(5):910-8.
25. Shevach E M. Mechanisms of foxp3+ T regulatory cell-mediated suppression. Immunity. 2009 May; 30(5):636-45.
26. Roncarolo M G, Gregori S, Battaglia M, Bacchetta R, Fleischhauer K, Levings M K. Interleukin-10-secreting type 1 regulatory T cells in rodents and humans. Immunol Rev. 2006 August; 212:28-50.
27. Weiner H L. The mucosal milieu creates tolerogenic dendritic cells and T(R)1 and T(H)3 regulatory cells. Nat Immunol. 2001 August; 2(8):671-2.
28. Vieira P L, Christensen J R, Minaee S, O'Neill E J, Barrat F J, Boonstra A, et al. IL-10-secreting regulatory T cells do not express Foxp3 but have comparable regulatory function to naturally occurring CD4+CD25+ regulatory T cells. J Immunol. 2004 May 15; 172(10):5986-93.
29. Pulendran B, Ahmed R. Translating innate immunity into immunological memory: implications for vaccine development. Cell. 2006 Feb. 24; 124(4):849-63.
30. Binder C J, Horkko S, Dewan A, Chang M K, Kieu E P, Goodyear C S, et al. Pneumococcal vaccination decreases atherosclerotic lesion formation: molecular mimicry between *Streptococcus pneumoniae* and oxidized LDL. Nat Med. 2003 June; 9(6):736-43.
31. Khallou-Laschet J, Tupin E, Caligiuri G, Poirier B, Thieblemont N, Gaston A T, et al. Atheroprotective effect of adjuvants in apolipoprotein E knockout mice. Atherosclerosis. 2006 February; 184(2):330-41.

32. Wigren M, Bengtsson D, Duner P, Olofsson K, Bjorkbacka H, Bengtsson E, et al. Atheroprotective effects of Alum are associated with capture of oxidized LDL antigens and activation of regulatory T cells. Circ Res. 2009 Jun. 19; 104(12):e62-70.
33. Sjogren P, Fredrikson G N, Samnegard A, Ericsson C G, Ohrvik J, Fisher R M, et al. High plasma concentrations of autoantibodies against native peptide 210 of apoB-100 are related to less coronary atherosclerosis and lower risk of myocardial infarction. Eur Heart J. 2008 September; 29(18):2218-26.
34. Fredrikson G N, Bjorkbacka H, Soderberg I, Ljungcrantz I, Nilsson J. Treatment with apo B peptide vaccines inhibits atherosclerosis in human apo B-100 transgenic mice without inducing an increase in peptide-specific antibodies. J Intern Med. 2008 December; 264(6):563-70.
35. Hu Xiangbing, Zhang Yankai, Lin Ming, Lu Yong, Zhang Yu, Zhang Huiyong, Chen Yingying, Hou Jing, Xing Yun, Jin Liang, Cao Rongyue, Liu Jingjing The fusion protein of HSP65 with tandem repeats of β-hCG acting as a potent tumor vaccine in suppressing hepatocarcinoma in International Immunopharmacology 10 (2010) 230-238

What is claimed is:

1. A fusion protein comprising
   (a) an antigenic fragment of apoB-100 protein, wherein the fragment is P2, P11, P25, P32, P45, P74, P102, P129, P143, P148, P154, P162, P210, P219, or P240 ; and
   (b) a protein carrier comprising subunit B of cholera toxin, wherein the antigenic fragment and the protein carrier are comprised in the fusion protein in a 1:1 fragment:carrier molar ratio; and
   wherein the fusion protein is capable of inducing antigen specific regulatory T cells, the antigen specific regulatory T cells being specific for the antigenic fragment of apoB-100.

2. The fusion protein of claim 1, wherein the antigenic fragment is one or more of P2, P45, P102 or P210.

3. The fusion protein of claim 1, wherein the antigenic fragment comprises P210.

4. An immunogenic composition comprising the fusion protein of claim 1 together with an adjuvant and/or an excipient.

5. The immunogenic composition of claim 4, wherein the adjuvant and/or excipients are pharmaceutically acceptable and the composition is a pharmaceutical composition.

6. A method to treat atherosclerosis in an individual, the method comprising:
   administering to the individual an effective amount of the fusion protein of claim 1,
   the effective amount eliciting an antigen specific Treg immunomodulatory response in the individual, the antigen specific Treg immunomodulatory response being specific for the antigenic fragments of apoB-100.

7. The method of claim 6, wherein the administering is performed via an oral or nasal or nasal route of administration.

8. The method of claim 6, wherein the administering is performed via a subcutaneous route of administration.

9. The method of claim 6, wherein the administering is performed via an intramuscular route of administration.

10. A method to produce a fusion protein, the method comprising
    attaching an antigenic fragment of apoB-100, wherein the fragment is P2, P11, P25, P32, P45, P74, P102, P129, P143, P148, P154, P162, P210, P219, or P240 with a suitable protein carrier comprising subunit B of cholera toxin in a 1:1 fragment:carrier molar ratio to provide a fusion protein capable of inducing antigen specific regulatory T cells,
    the antigen specific regulatory T cells being specific for the fragment of apoB-100.

11. The method of claim 10, wherein the attaching is performed by biological genetic engineering.

12. The method of claim 10, wherein the attaching is performed by chemical covalent conjugation.

13. A method to induce an antigen specific Tregulatory cell, the method comprising:
    contacting a Tregulatory cell with the fusion protein of claim 1, the contacting performed for a time and under condition to allow induction of a Tregulatory response,
    wherein the contacting results in an antigen-specific induction of a Tregulatory cell specific for the fragment of apoB-100 comprised in the fusion protein.

* * * * *